US010428151B2

(12) United States Patent
Kuhne et al.

(10) Patent No.: US 10,428,151 B2
(45) Date of Patent: Oct. 1, 2019

(54) TREATMENT OF HEMATOLOGIC MALIGNANCIES WITH AN ANTI-CXCR4 ANTIBODY

(71) Applicant: BRISTOL-MYERS SQUIBB COMPANY, Princeton, NJ (US)

(72) Inventors: Michelle R. Kuhne, Redwood City, CA (US); Chin Pan, Redwood City, CA (US); Josephine M. Cardarelli, Redwood City, CA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 400 days.

(21) Appl. No.: 14/356,996

(22) PCT Filed: Nov. 9, 2012

(86) PCT No.: PCT/US2012/064395
§ 371 (c)(1),
(2) Date: May 8, 2014

(87) PCT Pub. No.: WO2013/071068
PCT Pub. Date: May 16, 2013

(65) Prior Publication Data
US 2014/0322208 A1    Oct. 30, 2014

Related U.S. Application Data

(60) Provisional application No. 61/557,815, filed on Nov. 9, 2011, provisional application No. 61/569,113, filed on Dec. 9, 2011.

(51) Int. Cl.
| | | |
|---|---|---|
| *C07K 16/28* | (2006.01) | |
| *A61K 31/454* | (2006.01) | |
| *A61K 31/69* | (2006.01) | |
| *A61K 31/136* | (2006.01) | |
| *A61K 31/4184* | (2006.01) | |
| *A61K 31/555* | (2006.01) | |
| *A61K 31/573* | (2006.01) | |
| *A61K 31/675* | (2006.01) | |
| *A61K 31/7048* | (2006.01) | |
| *A61K 31/7068* | (2006.01) | |
| *A61K 39/395* | (2006.01) | |
| *A61K 39/00* | (2006.01) | |
| *A61K 45/06* | (2006.01) | |

(52) U.S. Cl.
CPC ........ *C07K 16/2866* (2013.01); *A61K 31/136* (2013.01); *A61K 31/4184* (2013.01); *A61K 31/454* (2013.01); *A61K 31/555* (2013.01); *A61K 31/573* (2013.01); *A61K 31/675* (2013.01); *A61K 31/69* (2013.01); *A61K 31/7048* (2013.01); *A61K 31/7068* (2013.01); *A61K 39/39558* (2013.01); *A61K 45/06* (2013.01); *A61K 2039/505* (2013.01); *C07K 2317/21* (2013.01); *C07K 2317/73* (2013.01); *C07K 2317/76* (2013.01)

(58) Field of Classification Search
CPC ............ C07K 16/2866; C07K 2317/73; C07K 2317/76; A61K 39/39558; A61K 2039/505
See application file for complete search history.

(56) References Cited

U.S. PATENT DOCUMENTS

| | | | | |
|---|---|---|---|---|
| 8,450,464 | B2 * | 5/2013 | Kuhne | ............ A61K 47/48384 424/130.1 |
| 8,569,280 | B2 * | 10/2013 | von Andrian | ........ A61K 39/395 514/183 |
| 2011/0070244 | A1 | 3/2011 | von Andrian et al. | |

FOREIGN PATENT DOCUMENTS

| | | |
|---|---|---|
| WO | WO 2006/089141 A2 | 8/2006 |
| WO | WO 2007/101235 | 9/2007 |
| WO | WO 2008/060367 A2 | 5/2008 |
| WO | WO 2008/142303 A2 | 11/2008 |
| WO | WO 2009/140124 A1 | 11/2009 |
| WO | WO 2010/105008 | 9/2010 |
| WO | WO 2010/135468 | 11/2010 |

OTHER PUBLICATIONS

Zhang, Xi et al., "Advances in the research of SDF-1/CXCR4 axis in the pathogenesis and treatment of multiple myeloma," Journal of Diagnostics Concepts & Practice, vol. 7, No. 4, pp. 463-466 (Dec. 31, 2008).
Office Action, dated Feb. 15, 2016, in Chinese Application No. 201280066551.7.
Beider, K. et al., "CXCR4 antagonist 4F-benzoyl-TN14003 inhibits leukemia and multiple myeloma tumor growth", Experimental Hematology, vol. 39, No. 3, pp. 282-292 (2011).
Kashyap, M.K. et al., "BMS-936564 (MDX1338): A Fully Human Anti-CXCR4 Antibody Induces Apoptosis in an In Vitro Model of Stromal-Leukemia Cell Interaction for Chronic Lymphocytic Leukemia", Abstract No. 2887, American Society of Hematology (ASH) 54th Annual Meeting, Dec. 8-11, 2012, Atlanta, GA (2012).
Kuhne, M.R. et al., "BMS-936564/MDX-1338: A Fully Human Anti-CXCR4 Antibody Induces Apoptosis In Vitro and Shows Antitumor Activity In Vivo in Hematologic Malignancies", Clinical Cancer Research, vol. 19, No. 2, pp. 357-366 (2012).
Li, C.-X. et al., "The Role of SDF-1alpha/CXCR4 in Promoting the Growth of Myeloma Cells", Abstract No. 5207, American Society of Hematology (ASH) 44th Annual Meeting, Dec. 6-10, 2002, Philadelphia, PA (2002).

(Continued)

*Primary Examiner* — Ruixiang Li
(74) *Attorney, Agent, or Firm* — Ashton J. Delauney

(57) ABSTRACT

The present disclosure provides human monoclonal antibodies that bind specifically to CXCR4 with high affinity. This disclosure also provides a method for treating a subject afflicted with a CXCR4-expressing cancer, in particular a hematological malignancy such as multiple myeloma, acute myeloid leukemia, or non-Hodgkin's lymphoma, comprising administering to the subject a therapeutically effective amount of a pharmaceutical composition comprising an anti-CXCR4 antibody of the disclosure. The disclosure further provides a kit for treating a cancer in a subject comprising a dose of an anti-CXCR4 antibody and instructions for using the anti-CXCR4 antibody in the therapeutic methods of the disclosure.

25 Claims, 40 Drawing Sheets
Specification includes a Sequence Listing.

(56) References Cited

OTHER PUBLICATIONS

Nervi, B. et al., "Chemosensitization of acute myeloid leukemia (AML) following mobilization by the CXCR4 antagonist AMD3100", Blood, vol. 113, pp. 6206-6214 (2009).

Roccaro, A.M. et al., "CXCR4 Monoclonal Antibody, BMS-936564 (MDX-1338), Modulates Epithelial to Mesenchymal Transition (EMT) in Multiple Myeloma Cells", Abstract No. 4009, American Society of Hematology (ASH) 54th Annual Meeting, Dec. 8-11, 2012, Atlanta, GA (2012).

Vaday, G.G. et al., "CXCR4 and CXCL12 (SDF-1) in Prostate Cancer: Inhibitory Effects of Human Single Chain Fv Antibodies", Clinical Cancer Research, vol. 10, No. 16, pp. 5630-5639 (2004).

Wemeau, M. et al., "Majoration de la sensibilité au bortézomib dans le myélome multiple en favorisant la migration des cellules tumorales dans le sang par un inhibiteur de CXCR4, l'AMD3100", Hématologie, vol. 15, No. 3, pp. 194-196 (2009).

Written Opinion for PCT Publication No. WO 2013/071068, dated May 9, 2014.

Zeng, Z. et al., "Targeting the leukemia microenvironment by CXCR4 inhibition overcomes resistance to kinase inhibitors and chemotherapy in AML", Blood, vol. 113, No. 24, pp. 6215-6224 (2009).

Sison, E.A.R., et al., "The bone marrow microenvironment and leukemia: biology and therapeutic targeting," Expert Rev. Hematol., vol. 4, No. 3, pp. 271-283 (Jun. 2011).

Kuhne, Michelle R., et al., "In Hematologic Malignancies Induces Apoptosis In Vitro and Shows Antitumor Activity In Vivo BMS-936564/MDX-1338: A Fully Human Anti-CXCR4 Antibody," Clin Cancer Res (2013), 19, pp. 357-366.

Möller, C., et al. "Expression and function of chemokine receptors in human multiple myeloma" Leukemia (2003) 17, pp. 203-210.

Peng, Sheng-Bin, et al., "Inhibition of CXCR4 by LY2624587, a Fully Humanized Anti-CXCR4 Antibody Induces Apoptosis of Hematologic Malignancies." PLOS ONE | DOI:10.1371/journal.pone.0150585, (Mar. 8, 2016), pp. 1-19.

Sanz-Rodríguez, Francisco, et al. "Chemokine stromal cell-derived factor-la modulates VLA-4 integrin-mediated multiple myeloma cell adhesion to CS-1/fibronectin and VCAM-1", Blood, (Jan. 15, 2001), vol. 97, No. 2, pp. 346-351.

Van De Broek, Isabelle, et al. "Clinical significance of chemokine receptor (CCR1,CCR2 and CXCR4) expression in human myeloma cells: the association with disease activity and survival," Haematologica, (2006), 91, pp. 200-206.

* cited by examiner

FIG. 1A

Anti-CXCR4 Fab BMS-936564/F7/MDX-1338 VH

```
V segment:    3-48
D segment:    4-23
J segment:    JH6b
```

```
        Q    V    Q    L    V    Q    S    G    G    G    L    V    Q    P    G    G    S    L
  1   CAG  GTG  CAG  CTG  GTG  CAG  TCT  GGG  GGA  GGC  TTG  GTA  CAG  CCT  GGG  GGG  TCC  CTG
                                                                          CDR1
                                                                  ~~~~~~~~~~~~~~~~~~~
        R    L    S    C    A    A    A    G    F    T    F    S    S    Y    S    M    N    W
 55   AGA  CTC  TCC  TGT  GCA  GCC  GCT  GGA  TTC  ACC  TTC  AGT  AGC  TAT  AGC  ATG  AAC  TGG
                                                                          CDR2
                                                                  ~~~~~~~~~~~~~~~~~~~
        V    R    Q    A    P    G    K    G    L    E    W    V    S    Y    I    S    S    R
109   GTC  CGC  CAG  GCT  CCA  GGG  AAG  GGG  CTG  GAG  TGG  GTT  TCA  TAC  ATT  AGT  AGT  AGA

CDR2
  ~~~~~~~~~~~~~~~~~~~~~~~~~~~~~~~~~~~~~~~~~~~~~
        S    R    T    I    Y    Y    A    D    S    V    K    G    R    F    T    I    S    R
163   AGT  AGA  ACC  ATA  TAC  TAC  GCA  GAC  TCT  GTG  AAG  GGC  CGA  TTC  ACC  ATC  TCC  AGA

D    N    A    K    N    S    L    Y    L    Q    M    N    S    L    R    D    E    D
217   GAC  AAT  GCC  AAG  AAC  TCA  CTG  TAT  CTG  CAA  ATG  AAC  AGC  CTG  AGA  GAC  GAG  GAC
                                                       CDR3
                                     ~~~~~~~~~~~~~~~~~~~~~~~~~~~~~~~~~~~~~~~~~~~~~~~~~~~~~
        T    A    V    Y    Y    C    A    R    D    Y    G    G    Q    P    P    Y    Y    Y
271   ACG  GCT  GTG  TAT  TAC  TGT  GCG  AGA  GAT  TAC  GGT  GGT  CAA  CCC  CCT  TAC  TAC  TAC

CDR3
  ~~~~~~~~~~~~~~~~~~~~~~~~~
        Y    Y    G    M    D    V    W    G    Q    G    T    T    V    T    V    S    S
325   TAC  TAC  GGT  ATG  GAC  GTC  TGG  GGC  CAA  GGG  ACC  ACG  GTC  ACC  GTC  TCC  TCA
```

FIG. 1B

Anti-CXCR4 Fab BMS-936564/F7/MDX-1338 VK

```
V segment:      L15
J segment:      JK1

A   I   R   M   T   Q   S   P   S   S   L   S   A   S   V   G   D   R
  1 GCC ATC CGG ATG ACC CAG TCT CCA TCC TCA CTG TCT GCA TCT GTA GGA GAC AGA

CDR1
                      ~~~~~~~~~~~~~~~~~~~~~~~~~~~~~~~~~~~~~~~~~
      V   T   I   T   C   R   A   S   Q   G   I   S   S   W   L   A   W   Y
 55 GTC ACC ATC ACT TGT CGG GCG AGT CAG GGT ATT AGC AGC TGG TTA GCC TGG TAT

CDR2
                                              ~~~~~~~~~~~~~~~~~~~~~~
      Q   Q   K   P   E   K   A   P   K   S   L   I   Y   A   A   S   S   L
109 CAG CAG AAA CCA GAG AAA GCC CCT AAG TCC CTG ATC TAT GCT GCA TCC AGT TTG

CDR2
      ~~~~~~~
      Q   S   G   V   P   S   R   F   S   G   S   G   S   G   T   D   F   T
163 CAA AGT GGG GTC CCA TCA AGG TTC AGC GGC AGT GGA TCT GGG ACA GAT TTC ACT

CDR3
                                                              ~~~~~~~
      L   T   I   S   S   L   Q   P   E   D   F   V   T   Y   Y   C   Q   Q
217 CTC ACC ATC AGC AGC CTG CAG CCT GAA GAT TTT GTA ACT TAT TAC TGC CAA CAG

CDR3
      ~~~~~~~~~~~~~~~~~~~~~~~~~~~
      Y   N   S   Y   P   R   T   F   G   Q   G   T   K   V   E   I   K
271 TAT AAT AGT TAC CCT CGG ACG TTC GGC CAA GGG ACC AAG GTG GAA ATC AAA
```

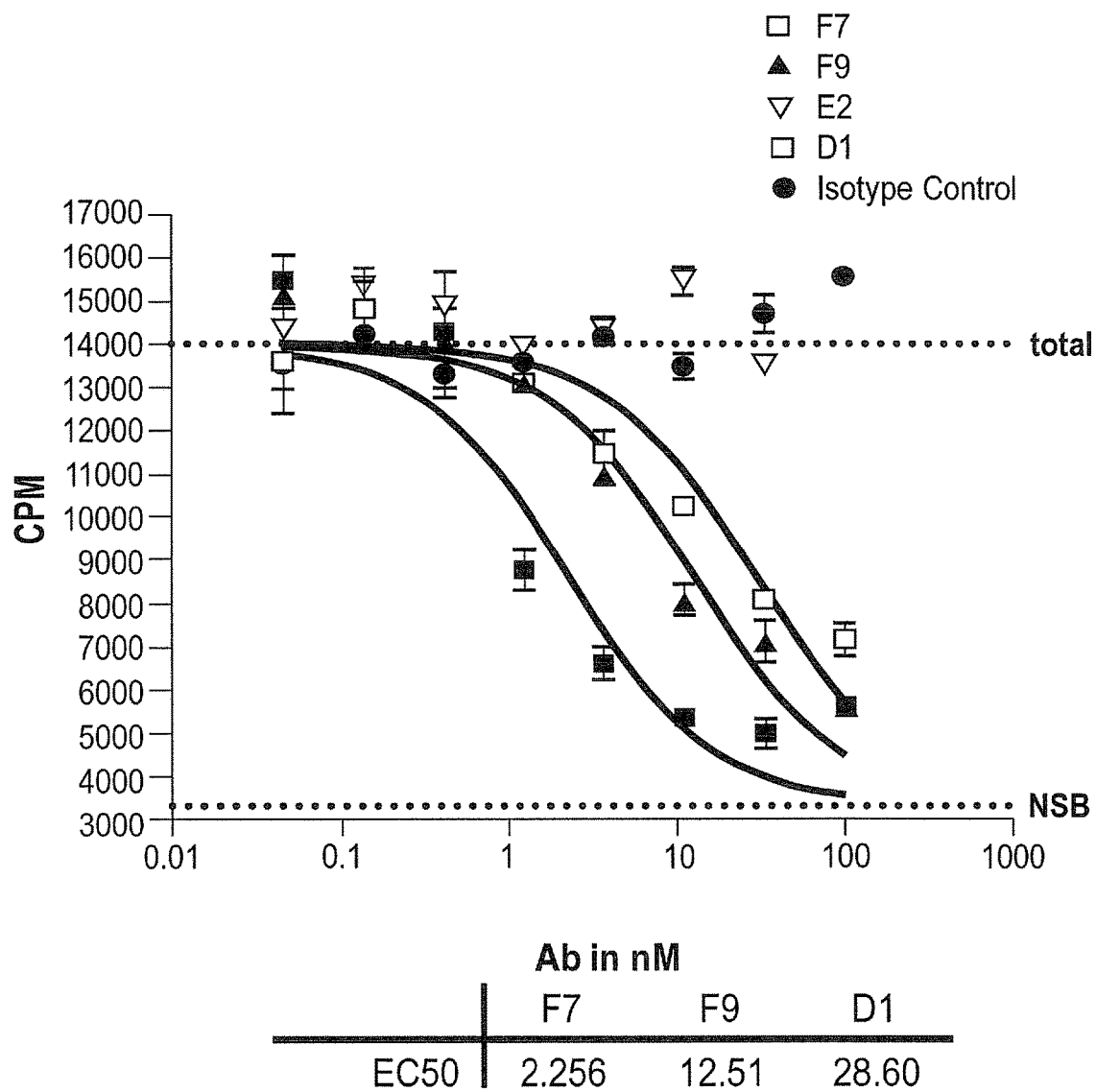

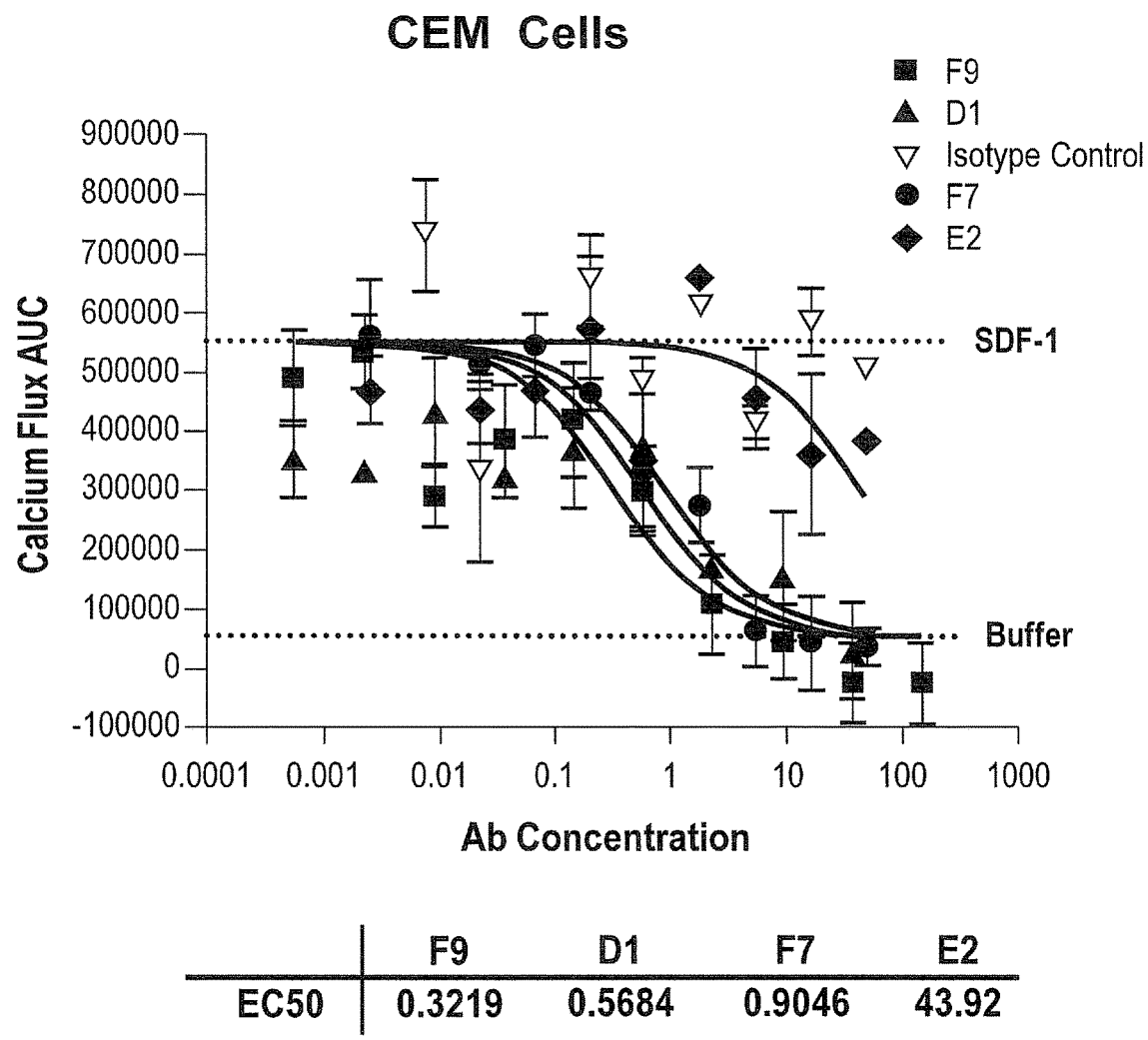

Proliferation of Ramos Cells
Abs: 41.25nM
Peptides: 100uM
CPT: 10uM

R1610-CXCR4 Cells

R1610 Cells

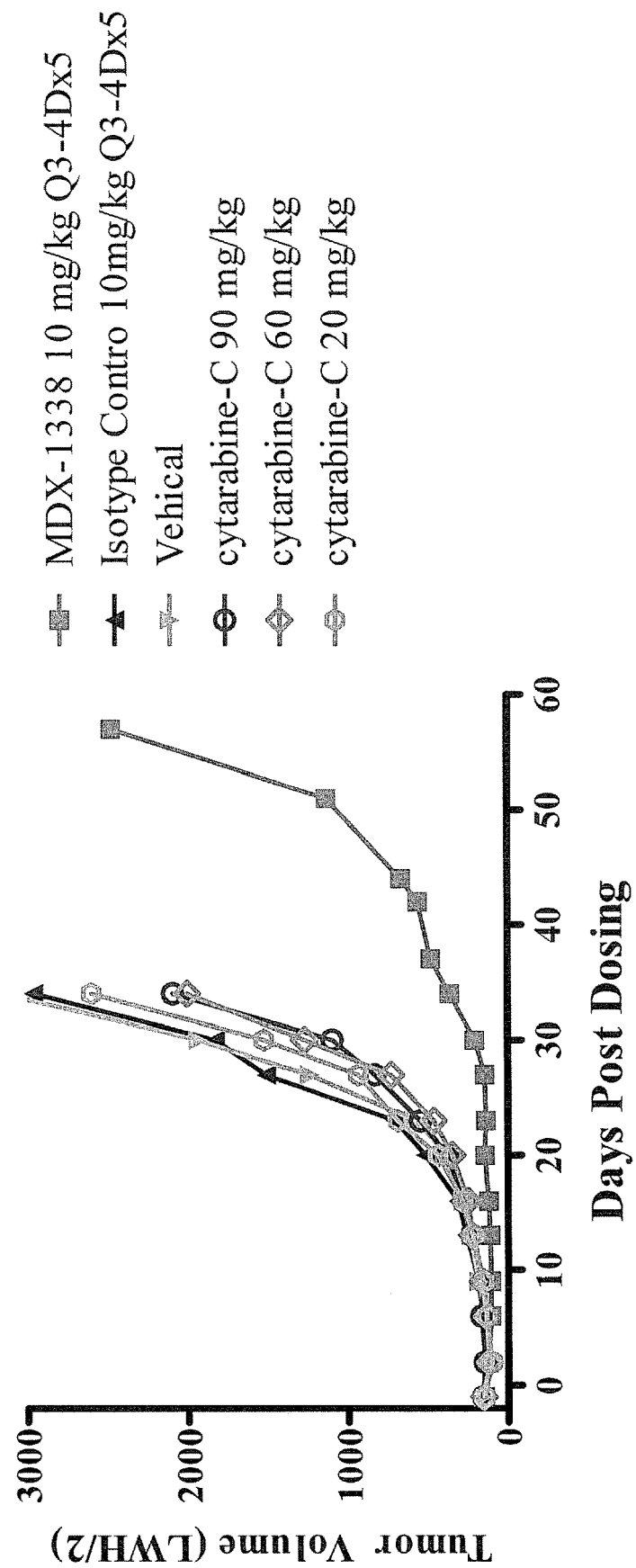

TREATMENT OF HEMATOLOGIC MALIGNANCIES WITH AN ANTI-CXCR4 ANTIBODY

This application is a 35 U.S.C. § 371 national stage application of International Application No. PCT/US2012/064395, filed Nov. 9, 2012, which claims the benefit of U.S. Provisional Patent Application Nos. 61/557,815, filed Nov. 9, 2011, and 61/569,113, filed Dec. 9, 2011, the contents of each of which are hereby incorporated herein in their entirety by reference.

Throughout this application, various publications are referenced in parentheses by author name and date, or by Patent No. or Publication No. Full citations for these publications may be found at the end of the specification immediately preceding the claims. The disclosures of these publications in their entireties are hereby incorporated by reference into this application in order to more fully describe the state of the art as known to those skilled therein as of the date of the invention described and claimed herein. However, the citation of a reference herein should not be construed as an acknowledgement that such reference is prior art to the present invention.

FIELD OF THE INVENTION

The present disclosure relates to human monoclonal antibodies that bind specifically to native human CXCR4 expressed on a cell surface, and the use of these antibodies in methods of treating cancer, particularly hematologic malignancy, including acute myeloid leukemia (AML), multiple myeloma (MM), and non-Hodgkin's lymphomas (NHLs) such as chronic lymphoid leukemia (CLL), follicular lymphoma (FL), and diffuse large B-cell lymphoma (DLBCL).

BACKGROUND OF THE INVENTION

Chemokines are a family of about 50 small proteins that modulate cell trafficking and angiogenesis and also play a significant role in the tumor microenvironment (Vicari et al., 2002). Depending on their structure, chemokines are classified as C-C chemokines (containing a cysteine-cysteine motif) or C-X-C chemokines (containing a cysteine-X-cysteine motif). Receptors that bind such chemokines thus are classified as members of the CCR family or CXCR family, respectively.

One member of the CXCR family is the CXCR4 receptor (CXCR4), also known as CD184, a seven-transmembrane domain G-protein coupled receptor consisting of an extra-cellular N-terminal tail and three extra-cellular loops. The intracellular carboxy terminus of CXCR4 is coupled to a heterotrimeric G-protein consisting of β and γ subunits and a pertussis toxin-sensitive Gi α subunit (Loetscher et al., 1994). To date, only one ligand for CXCR4, a chemokine known as CXCL12 (also known, and used interchangeably herein, as stromal cell-derived factor-1 or SDF-1) has been identified (Bleul et al., 1996; Oberlin et al., 1996). CXCL12 binding to CXCR4 stimulates activation of phospholipase C and subsequently results in an elevation of cytosolic free calcium. Ligation of CXCR4 ultimately leads to induction of chemotaxis and migration (Tachibana et al., 1998; Zou et al., 1998). CXCR4 also plays a role in embryogenesis, homeostasis and inflammation. Studies with mice engineered to be deficient in CXCR4 or CXCL12 implicate the CXCR4/CXCL12 pathway in organ vascularization, as well as in the immune and hematopoietic systems (Tachibana et al., 1998). Further, CXCR4 has been shown to function as a coreceptor for T lymphotrophic HIV-1 isolates (Feng et al., 1996).

In healthy adults, CXCR4 is predominantly expressed on hematopoietic lineage cells including B and T cells, monocytes, macrophages, NK, and dendritic cells, as well as $CD34^+$ bone marrow (BM) progenitor cells (Lee et al., 1999). Low levels of CXCR4 are also expressed on endothelial and epithelial cells, astrocytes, and neurons (Gupta et al., 1998; Hesselgesser et al., 1997). CXCL12 has been shown to induce endothelial cell migration and proliferation and, together with VEGF, has been shown to enhance neoangiogenesis (Guleng et al., 2005). Over-expression of CXCR4 has also been found in 75% of cancers including leukemias, lymphomas, pancreatic, breast, ovarian, lung, prostate and colorectal tumors, and the interaction between CXCL12 and is essential for homing and maintaining hematopoietic stem cells within the BM microenvironment (Mohle et al., 1998). Plerixafor (AMD3100; Mozobil), a bicyclam antagonist of CXCR4, has been shown to mobilize stem cells into the bloodstream (Dar et al., 2011). AMD3100 and AMD3465, another CXCR4 antagonist bicyclam, increase chemosensitization of AML tumor cells by blocking CXCR4/CXCL12 signaling (Nervi et al., 2009; Zeng et al., 2009).

AML is a fast-growing cancer of the myeloid line of blood cells, characterized by the rapid growth of abnormal white blood cells that accumulate in the BM and interfere with the production of normal blood cells. In AML, CXCR4 is highly expressed on the $CD34^+$ fraction of BM cells. Lower levels of CXCR4 on AML cells correlate with a better prognosis resulting in a longer relapse free and overall survival. The lower CXCR4 receptor expression attenuates migration of primary AML cells toward CXCL12 expressed in the chemo-protected environment of the BM (Tavor et al., 2004).

Multiple myeloma (MM) is a form of cancer that results from the malignant proliferation of plasma cells. After non-Hodgkin's lymphoma, it is the second most frequent hematological cancer, with approximately 80,000 new cases worldwide (20,000 in the United States), and approximately 62,000 deaths per year (10,500 deaths/year in the U.S.) (Jemal et al., 2008; 2009). MM cells grow preferentially in the BM where they interfere with the production of normal blood cells and normal antibodies, resulting in immunodeficiency, skeletal destruction, hypocalcemia, BM and renal failure. In addition to AML, serum levels of CXCL12 are elevated in patients with MM, and CXCR4 expression increases in extramedullary plasmacytoma, a manifestation of an advanced stage of MM. Furthermore, blockade of the CXCL12/CXCR4 axis attenuates migration of MM cells and homing of these cells to the BM (Alsayed et al., 2007).

Non-Hodgkin lymphomas include any of a diverse group of cancers of lymphocytes other than Hodgkin's lymphomas. NHLs can occur at any age and are often marked by lymph nodes that are larger than normal, fever, and weight loss. The many different types of NHL vary significantly in their severity, from very aggressive (fast-growing) to indolent (slow-growing) types, and they can be formed from either B-cells or T-cells. B-cell NHLs include Burkitt's lymphoma, chronic lymphocytic leukemia/small lymphoid lymphoma (CLL/SLL), diffuse large B-cell lymphoma (DLBCL), follicular lymphoma (FL), immunoblastic large cell lymphoma, precursor B-lymphoblastic lymphoma, and mantle cell lymphoma. T-cell NHLs include mycosis fungoides, anaplastic large cell lymphoma, and precursor T-lymphoblastic lymphoma. It is estimated that there will be approximately 70,000 new cases of NHLs in the United States in 2012, which will result in about 19,000 deaths.

High-level CXCR4 expression has been demonstrated in 18 out of 19 primary NHL cell lines tested (Bertolini et al., 2002). It has also been shown that CXCL12 enhances migration of follicular NHL cells (Corcione et al., 2000), and the CXCR4-CXCL12 circuitry appears to be crucial for migration of CLL cells (Burger et al., 1999).

Human anti-CXCR4 monoclonal antibodies that exhibit numerous desirable properties have previously been described in PCT International Publication No. WO 2008/060367 (Application No. PCT/US2007/021152), claiming priority to U.S. Provisional Application No. 60/827,851, filed Oct. 2, 2006. The disclosures of both these applications are hereby incorporated in their entireties by reference into this application. As disclosed in WO 2008/060367, in vitro studies demonstrate that these monoclonal antibodies bind to CXCR4-expressing cells with low nanomolar affinity, block CXCL12 binding to CXCR4-expressing cells, and inhibit CXCL12-induced migration and calcium flux with low nanomolar $EC_{50}$ values. One of the fully human monoclonal antibodies, BMS-936564, (designated F7 in WO 2008/060367, previously designated MDX-1338, and also assigned the non-proprietary name, ulocuplumab, by the United States Adopted Names (USAN) Council, all four designations being used interchangeably herein), which exhibited unexpectedly advantageous anti-solid tumor properties in preclinical studies, has been selected for further investigation to determine its activity against hematologic cancers in vivo and to further elucidate the mechanisms underlying its anti-cancer activity. Ulocuplumab (BMS-936564) has also entered Phase I clinical studies in patients with relapsed/refractory AML, MM, and NHLs.

SUMMARY OF THE INVENTION

The present disclosure provides isolated monoclonal antibodies, in particular human monoclonal antibodies, that bind to human CXCR4 and that exhibit numerous properties that are desirable in a therapeutic antibody. These properties include the ability to bind with low nM affinity to native human CXCR4 expressed on a cell surface, inhibit SDF-1 binding to human CXCR4 with an $EC_{50}$ for inhibition of 50 nM or less, inhibit SDF-1-induced calcium flux in cells expressing CXCR4 with an $EC_{50}$ for inhibition of 3 nM or less, inhibit SDF-1-induced migration of cells expressing CXCR4 with an $EC_{50}$ for inhibition of 50 nM or less, inhibit capillary tube formation by human umbilical vein endothelial cells (HuVECs), induce apoptosis in a wide variety of cells expressing CXCR4, inhibit tumor cell proliferation in vitro, inhibit tumor growth in vivo, inhibit metastases of $CXCR4^+$ tumor cells and/or increase survival time of a $CXCR4^+$ tumor-bearing subject.

In a preferred aspect, this disclosure pertains to isolated monoclonal antibody, preferably a human monoclonal antibody, or an antigen-binding portion thereof, wherein the monoclonal antibody:
  (a) binds to native human CXCR4 expressed on a cell surface;
  (b) inhibits binding of SDF-1 (CXCL12) to human CXCR4;
  (c) inhibits SDF-1-induced calcium flux in cells expressing human CXCR4;
  (d) inhibits SDF-1-induced migration of cells expressing human CXCR4; and
  (e) inhibits capillary tube formation by human umbilical vein endothelial cells.

Even more preferably, the antibody also induces apoptosis of cells expressing human CXCR4, induces tumor cell apoptosis in vivo, and/or inhibits growth of $CXCR4^+$ tumor cells.

This disclosure also provides a method for treating a subject afflicted with a CXCR4-expressing cancer, including a hematologic malignancy, comprising administering to the subject a therapeutically effective amount of an anti-CXCR4 antibody that specifically binds to human CXCR4 expressed on a cell surface. In certain embodiments, the anti-CXCR4 antibody inhibits the activity of CXCR4. In preferred embodiments, the anti-CXCR4 antibody induces apoptosis of CXCR4-expressing target cells. Accordingly, the anti-CXCR4 antibody is used in certain embodiments as monotherapy. In other embodiments, the anti-CXCR4 antibody is used in combination with other anti-cancer agents. In preferred embodiments, the hematologic malignancy is MM, AML, or NHLs. In preferred embodiments, the antibody is a human antibody. More preferably, the antibody is BMS-936564.

The disclosure further provides a use of a CXCR4 antibody for the preparation of a pharmaceutical composition for treating a subject afflicted with a cancer, including a hematologic malignancy.

This disclosure also provides a kit for treating a cancer in a subject, the kit comprising: (a) a dose of an anti-CXCR4 antibody; and (b) instructions for using the anti-CXCR4 antibody in any of the methods described herein. In a preferred embodiment, the anti-CXCR4 antibody is BMS-936564.

Other features and advantages of the instant disclosure will be apparent from the following detailed description and examples, which should not be construed as limiting. The contents of all references, GENBANK® entries, patents and published patent applications cited throughout this application are expressly incorporated herein by reference.

BRIEF DESCRIPTION OF THE FIGURES

FIG. 1 shows the nucleotide sequence (SEQ ID NO: 33) and amino acid sequence (SEQ ID NO: 25) of the heavy chain variable region (A) of the F7 (BMS-936564) human monoclonal antibody. The CDR1 (SEQ ID NO: 1), CDR2 (SEQ ID NO: 5) and CDR3 (SEQ ID NO: 9) regions are delineated and the V, D and J germline derivations are indicated. The nucleotide sequence (SEQ ID NO: 37) and amino acid sequence (SEQ ID NO: 29) of the light chain variable region (B) of F7 is also shown. The CDR1 (SEQ ID NO: 13), CDR2 (SEQ ID NO: 17) and CDR3 (SEQ ID NO: 21) regions are delineated and the V and J germline derivations are indicated.

FIG. 5 shows inhibition of binding of $^{125}$I-labeled CXCL12 to CXCR4 expressed on CEM cells by anti-CXCR4 human antibodies F7 (BMS-936564), F9 and D1. The E2 antibody does not inhibit binding of CXCL12 to CEM cells.

FIG. 7 shows inhibition of CXCL12 (SDF-1)-induced calcium flux in CEM cells by anti-CXCR4 human antibodies F7 (BMS-936564), F9 and D1. E2 does not significantly inhibit CXCL12-induced calcium flux.

FIG. 12 shows inhibition of Ramos tumor cell proliferation in vivo in a subcutaneous tumor model by anti-CXCR4 human antibodies F7 (BMS-936564) and F9.

DETAILED DESCRIPTION OF THE INVENTION

Figure 2:
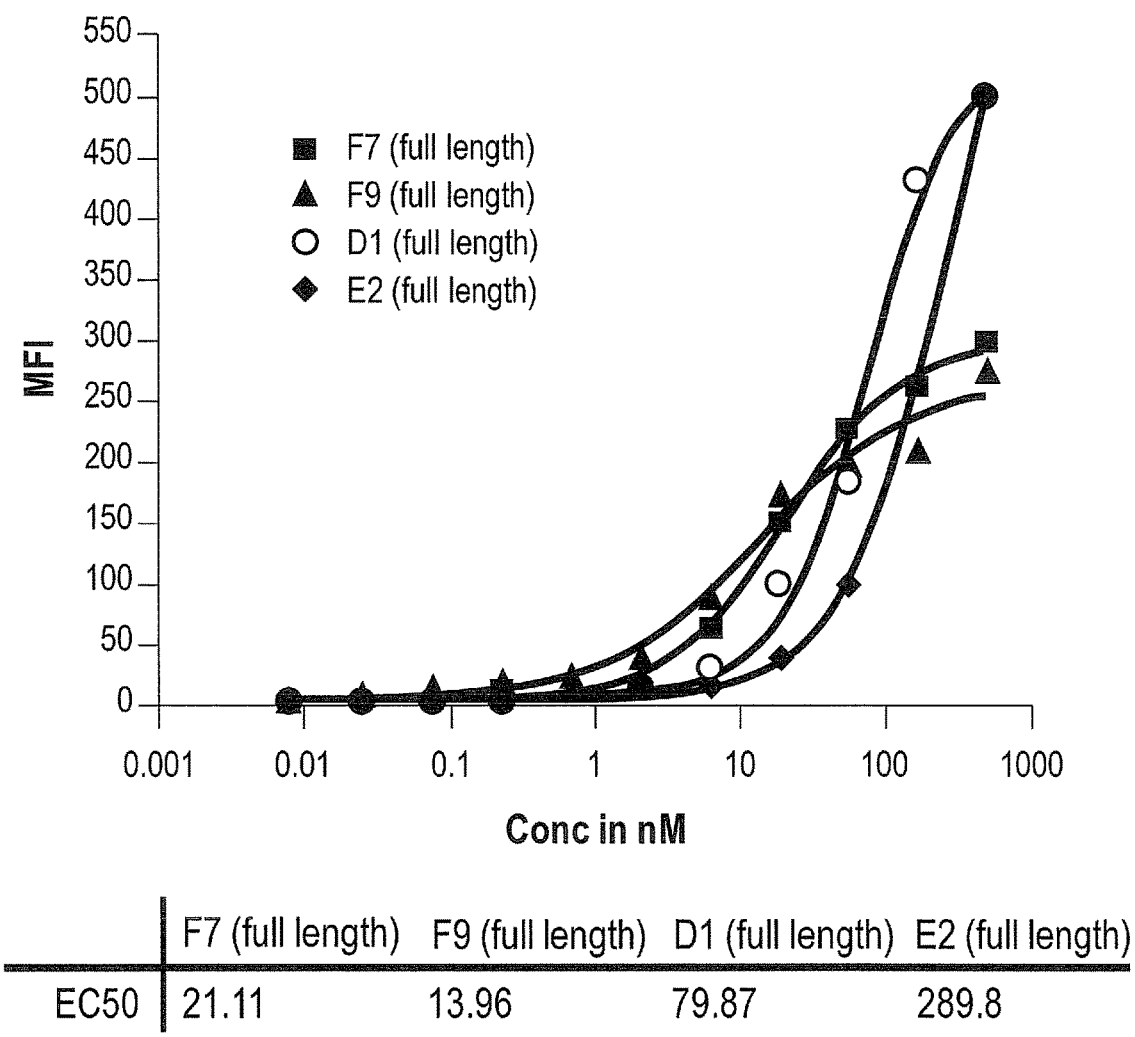
FIG. 2 shows the binding of human anti-CXCR4 antibodies F7, F9, D1 and E2 to CEM cells that express native human CXCR4 on the cell surface.

The present disclosure relates to isolated monoclonal antibodies, particularly human monoclonal antibodies, which bind specifically to native human CXCR4 expressed on a cell surface. In certain embodiments, the antibodies of this disclosure are derived from particular heavy and light chain germline sequences and/or comprise particular structural features such as variable regions or CDRs comprising particular amino acid sequences. This disclosure also relates to methods of using the antibodies to modulate CXCR4 activity in, or otherwise treat, diseases or disorders associated with expression of CXCR4 or involving the CXCR4/CXCL12 pathway, such as cancers, particularly hematological malignancies, tumor metastasis, HIV infection, inflammation and angiogenesis.

Terms

In order that the present disclosure may be more readily understood, certain terms are first defined. As used in this application, except as otherwise expressly provided herein, each of the following terms shall have the meaning set forth below. Additional definitions are set forth throughout the application.

"Administering" refers to the physical introduction of a composition comprising a therapeutic agent to a subject, using any of the various methods and delivery systems known to those skilled in the art. Preferred routes of administration for antibodies of the invention include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. Alternatively, an antibody of the invention can be administered via a non-parenteral route, such as a topical, epidermal or mucosal route of administration, for example, intranasally, orally, vaginally, rectally, sublingually or topically. Administering can also be performed, for example, once, a plurality of times, and/or over one or more extended periods.

An "antibody" (Ab) shall include, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three domains, $C_{H1}$, $C_{H2}$ and $C_{H3}$. Each light chain is comprised of a light chain variable region (abbreviated herein as $V_L$) and a light chain constant region. The light chain constant region is comprised of one domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies may mediate the binding of the immunoglobulin to host tissues or factors, including various cells of the immune system (e.g., effector cells) and the first component (C1q) of the classical complement system.

Antibodies typically bind specifically to their cognate antigen with high affinity, reflected by a dissociation constant ($K_D$) of $10^{-5}$ to $10^{-11}$ $M^{-1}$ or less. Any $K_D$ greater than about $10^{-4}$ $M^{-1}$ is generally considered to indicate nonspecific binding. As used herein, an antibody that "binds specifically" to an antigen refers to an antibody that binds to the antigen and substantially identical antigens with high affinity, which means having a $K_D$ of $10^{-7}$ M or less, preferably $10^{-8}$ M or less, even more preferably $5\times10^{-9}$ M or less, and most preferably between $10^{-8}$ M and $10^{-10}$ M or less, but does not bind with high affinity to unrelated antigens. An antigen is "substantially identical" to a given antigen if it exhibits a high degree of sequence identity to the given antigen, for example, if it exhibits at least 80%, at least 90%, preferably at least 95%, more preferably at least 97%, or even more preferably at least 99 sequence identity to the sequence of the given antigen. By way of example, an antibody that binds specifically to human CXCR4 may also have cross-reactivity with CXCR4 antigens from certain primate species but may not cross-react with CXCR4 antigens from certain rodent species or with an antigen other than CXCR4, e.g., a human PD-L1 antigen.

The immunoglobulin may derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers to the antibody class (e.g., IgM or IgG1) that is encoded by the heavy chain constant region genes. "Antibody" includes, by way of example, both naturally occurring and non-naturally occurring antibodies; monoclonal and polyclonal antibodies; chimeric and humanized antibodies; human or nonhuman antibodies; wholly synthetic antibodies; and single chain antibodies. A nonhuman antibody may be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

An "isolated antibody" refers to an antibody that is substantially free of other antibodies having different antigenic specificities (e.g., an isolated antibody that binds specifically to CXCR4 is substantially free of antibodies that bind specifically to antigens other than CXCR4). An isolated antibody that binds specifically to CXCR4 may, however, have cross-reactivity to other antigens, such as CXCR4 molecules from different species. Moreover, an isolated antibody may be substantially free of other cellular material and/or chemicals.

The phrases "an anti-antigen antibody", "an antibody recognizing an antigen", and "an antibody specific for an antigen" are used interchangeably herein with the term "an antibody which binds specifically to an antigen."

The term "monoclonal antibody" ("mAb") refers to a preparation of antibody molecules of single molecular composition, i.e., antibody molecules whose primary sequences are essentially identical, and which exhibits a single binding specificity and affinity for a particular epitope. Monoclonal antibodies may be produced by hybridoma, recombinant, transgenic or other techniques known to those skilled in the art.

A "human" antibody (HuMAb) refers to an antibody having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized" antibody refers to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

A "chimeric antibody" refers to an antibody in which the variable regions are derived from one species and the constant regions are derived from another species, such as an antibody in which the variable regions are derived from a mouse antibody and the constant regions are derived from a human antibody.

An "antigen-binding portion" of an antibody (also called an "antigen-binding fragment") refers to one or more fragments of an antibody that retain the ability to bind specifically to the antigen bound by the whole antibody.

A "cancer" refers a broad group of various diseases characterized by the uncontrolled growth of abnormal cells in the body. Unregulated cell division and growth divide and grow results in the formation of malignant tumors that invade neighboring tissues and may also metastasize to distant parts of the body through the lymphatic system or bloodstream.

The term "CXCR4" ("C-X-C chemokine receptor 4") includes variants, isoforms, homologs, orthologs and paralogs. For example, antibodies specific for CXCR4 may, in certain cases, cross-react with CXCR4 from species other than human. In other embodiments, the antibodies specific for human CXCR4 may be completely specific for human CXCR4 and may not exhibit species or other types of cross-reactivity. The term "human CXCR4" refers to human sequence CXCR4, such as the complete amino acid sequence of human CXCR4 having GENBANK® accession number P61073 (SEQ ID NO: 51). CXCR4 is also known in the art as, for example, LESTR, Fusin or CD184. The human CXCR4 sequence may differ from human CXCR4 of SEQ ID NO: 51 by having, for example, conserved mutations or mutations in non-conserved regions, and the CXCR4 has substantially the same biological function as the human CXCR4 of SEQ ID NO: 51. For example, a biological function of human CXCR4 is having an epitope in the extracellular domain of CXCR4 that is specifically bound by an antibody of the instant disclosure or the biological function of human CXCR4 is chemokine binding or involvement in the metastatic process.

A particular human CXCR4 sequence will generally be at least 90% identical in amino acids sequence to human CXCR4 of SEQ ID NO: 51 and contains amino acid residues that identify the amino acid sequence as being human when compared to CXCR4 amino acid sequences of other species (e.g., murine). In certain cases, a human CXCR4 may be at least 95%, or even at least 96%, 97%, 98%, or 99% identical in amino acid sequence to CXCR4 of SEQ ID NO: 51. In certain embodiments, a human CXCR4 sequence will display no more than 10 amino acid differences from the CXCR4 of SEQ ID NO: 51. In certain embodiments, the human CXCR4 may display no more than 5, or even no more than 4, 3, 2, or 1 amino acid difference from the CXCR4 of SEQ ID NO: 51. Percent identity can be determined as described herein.

A "CXCR4-expressing cancer" or "CXCR4$^+$ cancer" is a cancer wherein the malignant cells that characterize this cancer express CXCR4 on the cell surface, preferably expressing a high level of CXCR4.

The term "hematological malignancy" herein includes a lymphoma, leukemia, myeloma or a lymphoid malignancy, as well as a cancer of the spleen and the lymph nodes. Exemplary lymphomas that are amenable to treatment with the disclosed anti-CXCR4 antibodies of this invention include both B cell lymphomas and T cell lymphomas. B-cell lymphomas include both Hodgkin's lymphomas and most non-Hodgkins lymphomas. Non-limiting examples of B cell lymphomas include diffuse large B-cell lymphoma (DLBCL), follicular lymphoma (FL), mucosa-associated lymphatic tissue lymphoma (MALT), small cell lymphocytic lymphoma (overlaps with chronic lymphocytic leukemia), mantle cell lymphoma (MCL), Burkitt's lymphoma, mediastinal large B cell lymphoma, Waldenström macroglobulinemia, nodal marginal zone B cell lymphoma (NMZL), splenic marginal zone lymphoma (SMZL), intravascular large B-cell lymphoma, primary effusion lymphoma, lymphomatoid granulomatosis. Non-limiting examples of T cell lymphomas include extranodal T cell lymphoma, cutaneous T cell lymphomas, anaplastic large cell lymphoma, and angioimmunoblastic T cell lymphoma. Hematological malignancies also include leukemia, such as, but not limited to, secondary leukemia, chronic lymphocytic leukemia (CLL; also called chronic lymphoid leukemia), acute myelogenous leukemia (AML; also called acute lymphoid leukemia), chronic myelogenous leukemia (CML), B-cell prolymphocytic leukemia (B-PLL), acute lymphoblastic leukemia (ALL) and myelodysplasia (MDS). Hematological malignancies further include myelomas, such as, but not limited to, multiple myeloma (MM) and smoldering multiple myeloma (SMM). Other hematological and/or B cell- or T-cell-associated cancers are encompassed by the term hematological malignancy. For example, hematological malignancies also include cancers of additional hematopoietic cells, including dendritic cells, platelets, erythrocytes, natural killer cells, and polymorphonuclear leukocytes, e.g., basophils, eosinophils, neutrophils and monocytes. It should be clear to those of skill in the art that these pre-malignancies and malignancies will often have different names due to changing systems of classification, and that patients having lymphomas classified under different names may also benefit from the therapeutic regimens of the present invention.

The term "SDF-1" refers to stromal cell-derived factor 1, which is a ligand for CXCR4. The term "SDF-1" encompasses different isoforms of SDF-1, such as SDF-1α and SDF-1β. The amino acid sequence of human SDF-1α has GENBANK® accession number NP_954637. The amino acid sequence of human SDF-1β has GENBANK® accession number NP_000600. Human SDF-1 is also described in U.S. Pat. No. 5,756,084. SDF-1 is also known as CXCL12. The amino acid sequence of human SDF-1 can differ from the SDF-1 of NP_954637 or NP_000600, as described herein for CXCR4.

A "signal transduction pathway" refers to the biochemical relationship between a variety of signal transduction molecules that play a role in the transmission of a signal from one portion of a cell to another portion of a cell. As used herein, the phrase "cell surface receptor" includes, for example, molecules and complexes of molecules capable of receiving a signal and the transmission of such a signal across the plasma membrane of a cell. An example of a cell surface receptor of the present disclosure is the CXCR4 receptor.

A "subject" includes any human or nonhuman animal. The term "nonhuman animal" includes, but is not limited to, vertebrates such as nonhuman primates, sheep, dogs, cats, rabbits, ferrets, rodents such as mice, rats and guinea pigs, avian species such as chickens, amphibians, and reptiles. In preferred embodiments, the subject is a mammal such as a nonhuman primate, sheep, dog, cat, rabbit, ferret or rodent. In more preferred embodiments, the subject is a human. The terms, "subject", "patient" and "individual" are used interchangeably herein.

A "therapeutically effective amount" or "therapeutically effective dosage" of a drug or therapeutic agent, such as an antibody of the invention, is any amount of the drug that, when used alone or in combination with another therapeutic agent, promotes disease regression evidenced by a decrease in severity of disease symptoms, an increase in frequency and duration of disease symptom-free periods, or a prevention of impairment or disability due to the disease affliction. A therapeutically effective amount or dosage of a drug includes a "prophylactically effective amount" or a "prophylactically effective dosage", which is any amount of the drug that, when administered alone or in combination with another therapeutic agent to a subject at risk of developing a disease or of suffering a recurrence of disease, inhibits the development or recurrence of the disease. The ability of a therapeutic agent to promote disease regression can be evaluated using a variety of methods known to the skilled practitioner, such as in human subjects during clinical trials, in animal model systems predictive of efficacy in humans, or by assaying the activity of the agent in in vitro assays.

By way of example, an anti-cancer agent promotes cancer regression in a subject. In preferred embodiments, a therapeutically effective amount of the drug promotes cancer regression to the point of eliminating the cancer. "Promoting cancer regression" means that administering an effective amount of the drug, alone or in combination with an anti-neoplastic agent, results in a reduction in tumor growth or size, necrosis of the tumor, a decrease in severity of at least one disease symptom, an increase in frequency and duration of disease symptom-free periods, a prevention of impairment or disability due to the disease affliction, or otherwise amelioration of disease symptoms in the patient. In addition, the terms "effective" and "effectiveness" with regard to a treatment includes both pharmacological effectiveness and physiological safety. Pharmacological effectiveness refers to the ability of the drug to promote cancer regression in the patient. Physiological safety refers to the level of toxicity, or other adverse physiological effects at the cellular, organ and/or organism level (adverse effects) resulting from administration of the drug.

By way of example for the treatment of tumors, a therapeutically effective amount or dosage of the drug preferably inhibits cell growth or tumor growth by at least about 20%, more preferably by at least about 40%, even more preferably by at least about 60%, and still more preferably by at least about 80% relative to untreated subjects. In the most preferred embodiments, a therapeutically effective amount or dosage of the drug completely inhibits cell growth or tumor growth, i.e., preferably inhibits cell growth or tumor growth by 100%. The ability of a compound to inhibit tumor growth can be evaluated in an animal model system predictive of efficacy in human tumors. Alternatively, this property of a composition can be evaluated by examining the ability of the compound to inhibit cell growth, such inhibition can be measured in vitro by assays known to the skilled practitioner. In other preferred embodiments of the invention, tumor regression may be observed and continue for a period of at least about 20 days, more preferably at least about 40 days, or even more preferably at least about 60 days.

"Treatment" or "therapy" of a subject refers to any type of intervention or process performed on, or administering an active agent to, the subject with the objective of reversing, alleviating, ameliorating, inhibiting, slowing down or prevent the onset, progression, development, severity or recurrence of a symptom, complication, condition or biochemical indicia associated with a disease.

Various aspects of this disclosure are described in further detail in the following subsections.

Anti-CXCR4 Antibodies

Human monoclonal anti-CXCR4 antibodies of this disclosure can be generated using transgenic or transchromosomic mice carrying parts of the human immune system rather than the mouse system. These transgenic and transchromosomic mice include mice referred to herein as the HUMAB MOUSE® (Lonberg et al., 1994) and KM MOUSE® (WO 02/43478), respectively. The production of exemplary anti-CXCR4 antibodies of this invention is described in detail in WO 2008/060367. The antibodies of this disclosure are characterized by particular functional features or properties. For example, the antibodies bind to native human CXCR4 expressed on a cell surface. Preferably, an antibody of this disclosure binds to CXCR4 with high affinity, for example with a $K_D$ of $1 \times 10^{-7}$ M or less. The anti-CXCR4 antibodies of this disclosure preferably exhibit one or more of the following characteristics:

(a) binding to native human CXCR4 expressed on a cell surface;
(b) inhibiting binding of SDF-1 to CXCR4;
(c) inhibiting SDF-1-induced calcium flux in cells expressing CXCR4;
(d) inhibiting SDF-1-induced migration of cells expressing CXCR4;
(e) inhibiting capillary tube formation by human umbilical vein endothelial cells;
(f) binding to human CXCR4 with a KD of $1 \times 10^{-7}$ M or less;
(g) inducing apoptosis in cells expressing CXCR4;
(h) inhibiting proliferation of CXCR4$^+$ tumor cells in vitro;
(i) inhibiting CXCR4$^+$ tumor cell proliferation and/or inducing CXCR4$^+$ tumor cell apoptosis in vivo;
(j) inhibiting metastases of CXCR4$^+$ tumor cells; and/or
(k) increasing survival time of a CXCR4$^+$ tumor-bearing subject.

Preferably, an antibody of this disclosure binds to human CXCR4 with a $K_D$ of $5 \times 10^{-8}$ M or less, binds to human CXCR4 with a $K_D$ of $2 \times 10^{-8}$ M or less, binds to human CXCR4 with a $K_D$ of $5 \times 10^{-9}$ M or less, binds to human CXCR4 with a $K_D$ of $4 \times 10^{-9}$ M or less, binds to human CXCR4 with a $K_D$ of $3 \times 10^{-9}$ M or less, or binds to human CXCR4 with a $K_D$ of $2 \times 10^{-9}$ M or less.

Preferably, an antibody of the inhibits binding of SDF-1 to human CXCR4 with an $EC_{50}$ for inhibition of 50 nM or less, more preferably 30 nM or less, or 15 nM or less, or 10 nM or less, or 5 nM or less, or 3 nM or less (e.g., an $EC_{50}$ for inhibition of 28.60 nM or less, or 12.51 nM or less, or 2.256 nM or less)

Preferably, an antibody of this disclosure inhibits SDF-1-induced calcium flux in cells expressing human CXCR4 with an $EC_{50}$ for inhibition of 3 nM or less, more preferably 2 nM or less, or 1 nM or less, or 0.9 nM or less, or 0.8 nM or less, or 0.7 nM or less, or 0.6 nM or less, or 0.5 nM or less, or 0.4 nM or less (e.g., 0.9046 nM or less, 0.5684 or less, or 0.3219 nM or less).

Preferably, an antibody of this disclosure inhibits SDF-1-induced migration of cells expressing human CXCR4 with an $EC_{50}$ for inhibition of 50 nM or less, more preferably 30 nM or less, or 20 nM or less, or 15 nM or less (e.g., 18.99 nM or less, or 12.44 or less).

Standard assays to evaluate the binding ability of the antibodies toward native human CXCR4 expressed on a cell surface are known in the art, including for example, flow cytometry analysis using a cell line that naturally expresses native CXCR4 or that has been transfected to express native CXCR4. Suitable assays are described in detail in the Examples. A preferred cell line that expresses native CXCR4 is the CEM T cell line. Suitable assays for evaluating inhibition of binding of SDF-1, inhibition of SDF-1 induced calcium flux, inhibition of SDF-1 induced cell migration, inhibition of capillary tube formation by HuVECs, induction of apoptosis in cells expressing CXCR4 in vitro and/or in vivo, inhibition of growth of CXCR4$^+$ tumor cells in vitro and/or in vivo, and/or inhibition of metastases of CXCR4$^+$ tumor cells are also described in detail in the Examples. Binding affinity of the antibodies also can be determined by standard methods, such as by Scatchard analysis.

Anti-CXCR4 antibodies of the invention also include antigen-binding portions of the above antibodies. It has been amply demonstrated that the antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab')$_2$ fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an antibody.

These fragments, obtained initially through proteolysis with enzymes such as papain and pepsin, have been subsequently engineered into monovalent and multivalent antigen-binding fragments. For example, although the two domains of the Fv fragment, $V_L$ and $V_H$, are coded for by separate genes, they can be joined, using recombinant methods, by a synthetic linker peptide that enables them to be made as a single protein chain in which the $V_L$ and $V_H$ regions pair to form monovalent molecules known as single chain variable fragments (scFv). Divalent or bivalent scFvs (di-scFvs or bi-scFvs) can be engineered by linking two scFvs in within a single peptide chain known as a tandem scFv which contains two $V_H$ and two $V_L$ regions. ScFv dimers and higher multimers can also be created using linker peptides of fewer than 10 amino acids that are too short for the two variable regions to fold together, which forces the scFvs to dimerize and produce diabodies or form other multimers. Diabodies have been shown to bind to their cognate antigen with much higher affinity than the corresponding scFvs, having dissociation constants up to 40-fold lower than the $K_D$ values for the scFvs. Very short linkers (<3 amino acids) lead to the formation of trivalent triabodies or tetravalent tetrabodies that exhibit even higher affinities for to their antigens than diabodies. Other variants include minibodies, which are scFv-$C_{H3}$ dimers, and larger scFv-Fc fragments (scFv-$C_{H2}$-$C_{H3}$ dimers), and even an isolated CDR may exhibit antigen-binding function. These antibody fragments are engineered using conventional recombinant techniques known to those of skill in the art, and the fragments are screened for utility in the same manner as are intact antibodies. All of the above proteolytic and engineered fragments of antibodies and related variants (see Hollinger et al., 2005; Olafsen et al., 2010, for further details) are intended to be encompassed within the term "antigen-binding portion" of an antibody.

Monoclonal Antibodies F7, F9, D1 and E2

Preferred antibodies of this disclosure are the human monoclonal antibodies F7 (BMS-936564), F9, D1 and E2, isolated and structurally characterized as described in Examples 1 and 2. The $V_H$ amino acid sequences of F7, F9, D1 and E2 are shown in SEQ ID NOs. 25, 26, 27 and 28, respectively. The $V_L$ amino acid sequences of F7, F9, D1 and E2 are shown in SEQ ID NOs. 29, 30, 31 and 32, respectively. Additionally, alternative forms of F7, F9, D1 and E2, in which certain framework residues were substituted with a germline residue, were created and are referred to herein as F7GL, F9GL, D1GL and E2GL. The $V_H$ amino acid sequences of F7GL, F9GL, D1GL and E2GL are shown in SEQ ID NOs. 41, 42, 43 and 44, respectively. The $V_L$ amino acid sequences of F7GL, F9GL, D1GL and E2GL are shown in SEQ ID NOs. 45, 46, 47 and 48, respectively. Other anti-CXCR4 antibodies of this disclosure include antibodies result from "mixing and matching" different $V_H$ and $V_L$ regions, or different CDRs, to create antibodies that bind specifically to CXCR4 as described in WO 2008/060367.

Accordingly, in one aspect, this disclosure provides antibodies that comprise the heavy chain and light chain CDR1's, CDR2's and CDR3's of F7, F9, D1 or E2, or combinations thereof. The amino acid sequences of the $V_H$ CDR1's of F7, F9, D1 and E2 are shown in SEQ ID NOs. 1-4, respectively. The amino acid sequences of the $V_H$ CDR2's of F7, F9, D1 and E2 are shown in SEQ ID NOs. 5-8, respectively. The amino acid sequences of the $V_H$ CDR3's of F7, F9, D1 and E2 are shown in SEQ ID NOs. 9-12, respectively. The amino acid sequences of the $V_k$ CDR1's of F7, F9, D1 and E2 are shown in SEQ ID NOs. 13-16, respectively. The amino acid sequences of the $V_k$ CDR2's of F7, F9, D1 and E2 are shown in SEQ ID NOs. 17-20, respectively. The amino acid sequences of the $V_k$ CDR3's of F7, F9, D1 and E2 are shown in SEQ ID NOs. 21-24, respectively. The CDR regions identified above were delineated using the Kabat system (Kabat et al., 1991).

In one aspect, this disclosure provides a monoclonal antibody or antigen-binding portion thereof which binds specifically to CXCR4, preferably human CXCR4, and comprises a combination of $V_H$ and $V_L$ regions, each comprising three complementarity-determining regions (CDRs). In preferred embodiments, the monoclonal antibody or antigen-binding portion thereof comprises:

(a) the CDR1, CDR2 and CDR3 domains in a heavy chain variable region having the sequence set forth in SEQ ID NO: 25 or 41, and the CDR1, CDR2 and CDR3 domains in a light chain variable region having the sequence set forth in SEQ ID NO: 29 or 45;

(b) the CDR1, CDR2 and CDR3 domains in a heavy chain variable region having the sequence set forth in SEQ ID NO: 26 or 42, and the CDR1, CDR2 and CDR3 domains in a light chain variable region having the sequence set forth in SEQ ID NO: 30 or 46;

(c) the CDR1, CDR2 and CDR3 domains in a heavy chain variable region having the sequence set forth in SEQ ID NO: 27 or 43, and the CDR1, CDR2 and CDR3 domains in a light chain variable region having the sequence set forth in SEQ ID NO: 31 or 47; or (d) the CDR1, CDR2 and CDR3 domains in a heavy chain variable region having the sequence set forth in SEQ ID NO: 28 or 44, and the CDR1, CDR2 and CDR3 domains in a light chain variable region having the sequence set forth in SEQ ID NO: 32 or 48.

In other preferred embodiments, the monoclonal antibody or antigen-binding portion thereof of the invention comprises:

(a) a heavy chain variable region CDR1 comprising consecutively linked amino acids having the sequence set forth in SEQ ID NO: 1 or conservative modifications thereof; a heavy chain variable region CDR2 comprising consecutively linked amino acids having the sequence set forth in SEQ ID NO: 5 or conservative modifications thereof; a heavy chain variable region CDR3 comprising consecutively linked amino acids having the sequence set forth in SEQ ID NO: 9 or conservative modifications thereof; a light chain variable region CDR1 comprising consecutively linked amino acids having the sequence set forth in SEQ ID NO: 13 or conservative modifications thereof; a light chain variable region CDR2 comprising consecutively linked amino acids having the sequence set forth in SEQ ID NO: 17 or conservative modifications thereof; and a light chain variable region CDR3 comprising consecutively linked amino acids having the sequence set forth in SEQ ID NO: 21;

(b) a heavy chain variable region CDR1 comprising consecutively linked amino acids having the sequence set forth in SEQ ID NO: 2 or conservative modifications thereof; a heavy chain variable region CDR2 comprising consecutively linked amino acids having the sequence set forth in SEQ ID NO: 6 or conservative modifications thereof; a heavy chain variable region CDR3 comprising consecutively linked amino acids having the sequence set forth in SEQ ID NO: 10 or conservative modifications thereof; a light chain variable region CDR1 comprising consecutively linked amino acids having the sequence set forth in SEQ ID NO: 14 or conservative modifications thereof; a light chain variable region CDR2 comprising consecutively linked amino acids having the sequence set forth in SEQ ID NO: 18 or conservative modifications thereof; and a light chain variable region CDR3 comprising consecutively linked amino acids having the sequence set forth in SEQ ID NO: 22;

(c) a heavy chain variable region CDR1 comprising consecutively linked amino acids having the sequence set forth in SEQ ID NO: 3 or conservative modifications thereof; a heavy chain variable region CDR2 comprising consecutively linked amino acids having the sequence set forth in SEQ ID NO: 7 or conservative modifications thereof; a heavy chain variable region CDR3 comprising consecutively linked amino acids having the sequence set forth in SEQ ID NO: 11 or conservative modifications thereof; a light chain variable region CDR1 comprising consecutively linked amino acids having the sequence set forth in SEQ ID NO: 15 or conservative modifications thereof; a light chain variable region CDR2 comprising consecutively linked amino acids having the sequence set forth in SEQ ID NO: 19 or conservative modifications thereof; and a light chain variable region CDR3 comprising consecutively linked amino acids having the sequence set forth in SEQ ID NO: 23; or (d) a heavy chain variable region CDR1 comprising consecutively linked amino acids having the sequence set forth in SEQ ID NO: 4 or conservative modifications thereof; a heavy chain variable region CDR2 comprising consecutively linked amino acids having the sequence set forth in SEQ ID NO: 8 or conservative modifications thereof; a heavy chain variable region CDR3 comprising consecutively linked amino acids having the sequence set forth in SEQ ID NO: 12 or conservative modifications thereof; a light chain variable region CDR1 comprising consecutively linked amino acids having the sequence set forth in SEQ ID NO: 16 or conservative modifications thereof; a light chain variable region CDR2 comprising consecutively linked amino acids having the sequence set forth in SEQ ID NO: 20 or conservative modifications thereof; and a light chain variable region CDR3 comprising consecutively linked amino acids having the sequence set forth in SEQ ID NO: 24.

In further embodiments, the monoclonal antibody or antigen-binding portion thereof of the invention comprises:

(a) a heavy chain variable region comprising consecutively linked amino acids having the sequence set forth in SEQ ID NO: 25 or 41 or conservative modifications thereof, and a light chain variable region comprising consecutively linked amino acids having the sequence set forth in SEQ ID NO: 29 or 45 or conservative modifications thereof;

(b) a heavy chain variable region comprising consecutively linked amino acids having the sequence set forth in SEQ ID NO: 26 or 42 or conservative modifications thereof, and a light chain variable region comprising consecutively linked amino acids having the sequence set forth in SEQ ID NO: 30 or 46 or conservative modifications thereof;

(c) a heavy chain variable region comprising consecutively linked amino acids having the sequence set forth in SEQ ID NO: 27 or 43 or conservative modifications thereof, and a light chain variable region comprising consecutively linked amino acids having the sequence set forth in SEQ ID NO: 31 or 47 or conservative modifications thereof; or (d) a heavy chain variable region comprising consecutively linked amino acids having the sequence set forth in SEQ ID NO: 28 or 44 or conservative modifications thereof, and a light chain variable region comprising consecutively linked amino acids having the sequence set forth in SEQ ID NO: 32 or 48 or conservative modifications thereof.

In a preferred embodiment, the anti-CXCR4 antibody or antigen-binding portion thereof comprises:

(a) a heavy chain variable region CDR1 comprising consecutively linked amino acids having the sequence set forth in SEQ ID NO: 1;

(b) a heavy chain variable region CDR2 comprising consecutively linked amino acids having the sequence set forth in SEQ ID NO: 5;

(c) a heavy chain variable region CDR3 comprising consecutively linked amino acids having the sequence set forth in SEQ ID NO: 9;

(d) a light chain variable region CDR1 comprising consecutively linked amino acids having the sequence set forth in SEQ ID NO: 13;

(e) a light chain variable region CDR2 comprising consecutively linked amino acids having the sequence set forth in SEQ ID NO: 17; and (f) a light chain variable region CDR3 comprising consecutively linked amino acids having the sequence set forth in SEQ ID NO: 21.

In another preferred embodiment, the anti-CXCR4 antibody or antigen-binding portion thereof comprises:

(a) a heavy chain variable region CDR1 comprising consecutively linked amino acids having the sequence set forth in SEQ ID NO: 2;

(b) a heavy chain variable region CDR2 comprising consecutively linked amino acids having the sequence set forth in SEQ ID NO: 6;

(c) a heavy chain variable region CDR3 comprising consecutively linked amino acids having the sequence set forth in SEQ ID NO: 10;

(d) a light chain variable region CDR1 comprising consecutively linked amino acids having the sequence set forth in SEQ ID NO: 14;

(e) a light chain variable region CDR2 comprising consecutively linked amino acids having the sequence set forth in SEQ ID NO: 18; and (f) a light chain variable region CDR3 comprising consecutively linked amino acids having the sequence set forth in SEQ ID NO: 22.

Antibodies that Bind to the Same Epitope as Anti-CXCR4 Antibodies

In another embodiment, this disclosure provides antibodies or antigen-binding portions thereof that bind to the same epitope region (i.e., the same or an overlapping epitope) on human CXCR4 as any of the anti-CXCR4 monoclonal antibodies of this disclosure (i.e., antibodies that have the ability to cross-compete for binding to CXCR4 with any of the monoclonal antibodies of this disclosure). In preferred embodiments, the reference antibody for cross-competition studies can be the monoclonal antibody F7 (BMS-936564) (having $V_H$ and $V_L$ sequences as shown in SEQ ID NOs: 25 and 29, respectively), or the monoclonal antibody F9 (having $V_H$ and $V_L$ sequences as shown in SEQ ID NOs: 26 and 30, respectively) or the monoclonal antibody D1 (having $V_H$ and $V_L$ sequences as shown in SEQ ID NOs: 27 and 31, respectively) or the monoclonal antibody E2 (having $V_H$ and $V_L$ sequences as shown in SEQ ID NOs: 28 and 32, respectively). Accordingly, this disclosure provides a human monoclonal antibody, or an antigen-binding portion thereof, which cross-competes for binding to human CXCR4 with a reference antibody or reference antigen-binding portion thereof, wherein the reference antibody or portion thereof comprises:

(a) a heavy chain variable region comprising consecutively linked amino acids having the sequence set forth in SEQ ID NO: 25 and a light chain variable region comprising consecutively linked amino acids having the sequence set forth in SEQ ID NO: 29;

(b) a heavy chain variable region comprising consecutively linked amino acids having the sequence set forth in SEQ ID NO: 26 and a light chain variable region comprising consecutively linked amino acids having the sequence set forth in SEQ ID NO: 30;

(c) a heavy chain variable region comprising consecutively linked amino acids having the sequence set forth in SEQ ID NO: 27 and a light chain variable region comprising consecutively linked amino acids having the sequence set forth in SEQ ID NO: 31; or (d) a heavy chain variable region comprising consecutively linked amino acids having the sequence set forth in SEQ ID NO: 28 and a light chain variable region comprising consecutively linked amino acids having the sequence set forth in SEQ ID NO: 32.

In a preferred aspect, the cross-competing anti-CXCR4 monoclonal antibody of the invention comprises a $V_H$ region comprising consecutively linked amino acids having a sequence derived from a human $V_H$ 3-48 germline sequence as set forth in SEQ ID NO: 49 and/or a $V_L$ region comprising consecutively linked amino acids having a sequence derived from a human $V_K$ L15 germline sequence as set forth in SEQ ID NO: 50.

The cross-competing antibodies can be identified based on their ability to cross-compete with F7, F9, D1, E2 or any other reference anti-CXCR4 antibody of the invention in a standard CXCR4 binding assay, for example, flow cytometry with CEM cells, wherein the reference antibody is labeled with FITC and the ability of a test antibody to inhibit the binding of the FITC-labeled reference antibody to CEM cells is evaluated.

Pharmaceutical Compositions

In another aspect, the present disclosure provides a composition, e.g., a pharmaceutical composition, containing one or a combination of monoclonal antibodies, or antigen-binding portion(s) thereof, of the present disclosure, formulated together with a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. Preferably, the carrier is suitable for intravenous, intramuscular, subcutaneous, parenteral, spinal or epidermal administration (e.g., by injection or infusion). A pharmaceutical composition of the invention may include one or more pharmaceutically acceptable salts, anti-oxidant, aqueous and nonaqueous carriers, and/or adjuvants such as preservatives, wetting agents, emulsifying agents and dispersing agents.

Dosage regimens are adjusted to provide the optimum desired response, e.g., a therapeutic response or minimal adverse effects.

For administration of a human anti-CXCR4 antibody, the dosage ranges from about 0.0001 to 100 mg/kg, preferably from about 0.01 to about 20 mg/kg, and more preferably 0.1 to 10 mg/kg, of the subject's body weight. For example, dosages can be 0.1, 0.3, 1, 3, 5 or 10 mg/kg body weight, and more preferably, 0.3, 1, 3, or 10 mg/kg body weight. The dosing schedule is typically designed to achieve exposures that result in sustained receptor occupancy based on typical pharmacokinetic properties of an antibody. An exemplary treatment regime entails administration once per week, once every two weeks, once every three weeks, once every four weeks, once a month, once every 3 months or once every three to 6 months. Considering that an IgG4 antibody typically has a half-life of 2-3 weeks, a preferred dosage regimen for an anti-CXCR4 antibody of the disclosure comprises 0.3-20 mg/kg body weight, preferably 1-10 mg/kg body weight, via intravenous administration, with the antibody being given every 7 or 14 days in up to 6-week, 8-week or 12-week cycles until complete response or confirmed progressive disease.

The dosage and scheduling may change during a course of treatment. For example, dosage regimens for an anti-CXCR4 antibody of this disclosure include 1, 3 or 10 mg/kg body weight via intravenous (IV) administration, with the antibody being given using one of the following dosing schedules: (i) every 7 days in up to 6-week cycles; (ii) every two weeks for up to six dosages, then every three months; (iii) every three weeks; (iv) 1-10 mg/kg body weight once followed by 1 mg/kg body weight every 2-3 weeks.

In some methods, two or more monoclonal antibodies with different binding specificities are administered simultaneously, in which case the dosage of each antibody administered falls within the ranges indicated. Antibody is usually administered on multiple occasions. Intervals between single dosages can be, for example, weekly, monthly, every three months or yearly. Intervals can also be irregular as indicated by measuring blood levels of antibody to the target antigen in the patient. In some methods, dosage is adjusted to achieve a plasma antibody concentration of about 1-1000 µg/ml and in some methods about 25-300 µg/ml.

Alternatively, antibody can be administered as a sustained release formulation, in which case less frequent administration is required. Dosage and frequency vary depending on the half-life of the antibody in the patient. In general, human antibodies show the longest half life, followed by humanized antibodies, chimeric antibodies, and nonhuman antibodies. The dosage and frequency of administration can vary depending on whether the treatment is prophylactic or therapeutic. In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patient can be administered a prophylactic regime.

Actual dosage levels of the active ingredients in the pharmaceutical compositions of the present disclosure may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present disclosure employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present invention can be administered via one or more routes of administration using one or more of a variety of methods well known in the art. As will be appreciated by the skilled artisan, the route and/or mode of administration will vary depending upon the desired results.

The active compounds can be prepared with carriers that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., Robinson (1978).

Therapeutic compositions can be administered with medical devices known in the art. For example, in a preferred embodiment, a therapeutic composition of this disclosure can be administered with a needleless hypodermic injection device, such as the devices disclosed in U.S. Pat. Nos. 5,399,163, 5,383,851, or 4,941,880. The subject matter of these patents is incorporated herein by reference. Many other such implants, delivery systems, and modules are known to those skilled in the art.

Uses and Methods of the Invention

The antibodies, antibody compositions and methods of the present disclosure have numerous in vitro and in vivo diagnostic and therapeutic utilities involving the diagnosis and treatment of CXCR4-associated disorders including, for example, methods for treating a subject afflicted with a CXCR4-expressing cancer comprising administering to the subject a therapeutically effective amount of an antibody or a fragment thereof that specifically binds to CXCR4 expressed on a cell surface. Preferred subjects include human patients having disorders such as hematological malignancies that are associated with, mediated or modulated by, CXCR4 activity or involve the CXCR4/CXCL12 pathway. In certain embodiments of these methods for treating a cancer patient, the anti-CXCR4 antibody or fragment thereof is administered as monotherapy, whereas in other embodiments, it is administered in combination with another agent, such as an anti-neoplastic chemotherapeutic agent. When antibodies to CXCR4 are administered in combination with another agent, the two can be administered in either order or simultaneously.

CXCR4 is known to be expressed on a wide variety of tumor cells types and also is known to be involved in tumor metastasis. Moreover, as a coreceptor for HIV entry into T cells, CXCR4 is known to be involved in HIV infection. Additionally, the CXCR4/CXCL12 pathway has been shown to be involved in inflammatory conditions. Still further, the CXCR4/CXCL12 pathway has been shown to be involved in angiogenesis or neovascularization. Accordingly, the anti-CXCR4 antibodies (and immunoconjugates and bispecific molecules) of this disclosure can be used in a variety of clinical situations, including the following:

A. Cancer

Over-expression of CXCR4 has also been demonstrated in about 75% of cancers, and in certain situations an inverse correlation has been established between CXCR4 expression and patient prognosis or survival. Non-limiting examples of cancer types associated with CXCR4 expression or the CXCR4/CXCL12 pathway include solid tumors such as breast (Muller et al., 2001), ovarian (Scotton et al., 2001), prostate (Taichman et al., 2002), non-small cell lung (Spano et al., 2004), pancreatic (Koshiba et al., 2000), colorectal (Zeelenberg et al., 2003), kidney (Schrader et al., 2002), and thyroid cancer (Hwang et al., 2003), nasopharyngeal carcinoma (Wang et al., 2005), melanoma (Scala et al., 2005), renal cell carcinoma (Staller et al., 2003), neuroblastoma (Geminder et al., 2001), glioblastoma (Rempel et al., 2000), rhabdomyosarcoma (Libura et al., 2002), and osteosarcoma (Laverdiere et al., 2005), as well as hematological malignancies such as acute lymphoblastic leukemia (Crazzolara et al., 2001), acute myeloid leukemia (Mohle et al., 1998; Rombouts et al., 2004), multiple myeloma (Alsayed et al., 2007; Azab et al., 2009), chronic lymphoid leukemia (Mohle et al., 1999; Burger et al., 1999), chronic myeloid leukemia (Jin et al., 2008), and non-Hodgkin's lymphoma (Bertolini et al., 2002; Weng et al., 2003).

Additionally, this pathway is implicated in stimulating the metastatic process in multiple neoplasms (Murphy, 2001). In clinical studies, CXCR4 has been associated with increased propensity for metastasis and decreased survival and has been identified as a prognostic indicator for acute myeloid leukemia, breast, colorectal, non-small-cell lung, ovarian and pancreatic carcinoma in which greater expression of CXCR4 correlates with disease severity (Spoo et al., 2007; Hiller et al., 2011; Ottaiano et al., 2006; Spano et al., 2004; Jiang et al., 2006; Marechal et al., 2009).

Bone marrow stromal cells (BMSCs) secrete CXCL12 and the interaction with CXCR4 is essential for homing and maintaining hematopoietic stem cells within the BM microenvironment (Mohle et al., 1998). Leukemic cells express high levels of CXCR4, and the pathway plays a critical role in leukemic cell migration into the BM which in turn, supports their growth and survival. CXCR4 is essential for metastatic spread to organs such as BM where CXCL12 is expressed. Collectively, CXCR4 plays an important role in both homing and retention of hematopoietic stem cells in the BM and an antagonist of CXCR4 mobilizes stem cells into the bloodstream, as demonstrated with the small-molecule CXCR4 antagonist, AMD3100 (plerixafor; Mozobil) which was approved by the FDA for use in combination with granulocyte-colony stimulating factor for autologous transplants in NHL and MM patients (Dar et al., 2011). Another CXCR4 inhibitor, AMD3465, was shown to antagonize CXCL12- and stroma-induced chemotaxis and inhibited CXCL12-induced activation of prosurvival signaling pathways in leukemic cells (Zeng et al., 2009). Further, it was demonstrated that AMD3465, alone or in combination with granulocyte colony-stimulating factor, induced mobilization of AML cells and progenitor cells into circulation and enhanced antileukemic effects of chemotherapy and sorafenib, resulting in markedly reduced leukemia burden and prolonged survival of the animals (Zeng et al., 2009). Such findings suggest that disruption of CXCR4/CXCL12 interactions may be used to sensitize leukemic cells to chemotherapy by targeting their protective bone marrow microenvironment.

As described in the Examples, novel first-in-class human therapeutic monoclonal antibodies directed to CXCR4 have been developed. These monoclonal antibodies bind to CXCR4-expressing cells with low nanomolar affinity, block CXCL12 binding to CXCR4-expressing cells and inhibit CXCL12-induced migration and calcium flux with low nanomolar $EC_{50}$ values. Significantly, in addition to blocking CXCL12-induced calcium flux and migration, data provided in the Examples also indicate that antibody-dependent induction of apoptosis of CXCR4-expressing tumor cells is a mechanism of action of these human anti-CXCR4 antibodies. Antibody-induced apoptosis resulted in robust in vivo efficacy across multiple hematopoietic tumor xenograft models. Based on the action of small-molecule CXCR4 antagonists in increasing mobilization of $CXCR4^+$ tumor cells from the BM and thereby increasing chemosensitization, but in not directly killing such tumor cells, the efficacy of the present anti-CXCR4 antibodies in killing cancer cells was surprising and unexpected.

Because CXCR4 plays a role in multiple fundamental aspects of cancer including proliferation, migration/invasion and angiogenesis, an antagonist has potentially multiple means to intervene in malignancies where CXCR4 is expressed. To begin to dissect the pathway, fully human monoclonal antibodies directed against CXCR4 and CXCL12, respectively, were developed. Both the anti-CXCR4 and anti-CXCL12 antibodies inhibit ligand binding to CXCR4 resulting in inhibition of ligand-induced cellular responses such as calcium flux and migration (Examples 4-6). In addition to these functions, the CXCR4/CXCL12 axis has been implicated in promoting angiogenesis (Guleng et al., 2005); Ping et al., 2011). Both anti-CXCR4 (Example 7) and anti-CXCL12 (data not shown) antibodies also inhibited endothelial tube formation, an in vitro demonstration of angiogenesis.

To investigate the effects of the disruption of CXCR4/CXCL12 interactions, the efficacy of the antibodies in attenuating tumor growth was tested in diverse in vivo xenograft models. In a model for NHL (Burkitt's lymphoma), Ramos cells were engrafted into SCID mice and rituximab was used as a positive control. Surprisingly, anti-CXCL12 antibody did not control tumor growth and appeared indistinguishable from vehicle and isotype control. In contrast, anti-CXCR4 antibody BMS-936564 demonstrated nearly complete tumor growth control with similar activity as rituximab (Example 14). Because in vitro blockade of chemotaxis was similar between the two antibodies (Example 6), it is unlikely that anti-tumor control is dependent on blockade of the CXCL12/CXCR4 axis. Consequently, a direct cytotoxic effect of BMS-936564 was tested in a Ramos cell proliferation assay. CXCL12 has been implicated as an autocrine factor promoting cell growth and in a separate study CXCL12 siRNA inhibited BR5-1 growth (Liu et al., 2011; Righi et al., 2011). Though the inhibition of growth was partial, a dose-dependent inhibition of proliferation with anti-CXCR4 was observed, whereas AMD3100 and anti-CXCL12 antibody had no effect (Example 8). Recently, a 14-residue polypeptide reported to be a specific CXCR4 antagonist (BKT140) was shown to inhibit proliferation of multiple myeloma cells (Beider et al., 2011). It has been suggested that AMD3100 is a weak partial agonist while BKT140 acts as an inverse agonist (Zhang et al., 2002).

In view of the foregoing, the anti-CXCR4 antibodies of this disclosure can be used in a method for treating a subject afflicted with a CXCR4-expressing cancer comprising administering to the subject a therapeutically effective amount of an antibody or a fragment thereof that specifically binds to a CXCR4 receptor expressed on the surface of a cancer cell. In certain embodiments, the treatment method is used prophylactically on a subject who was previously afflicted with, or a subject who is at risk of contracting, a cancer. In preferred embodiments, the subject is a human and the antibody or fragment thereof binds to a human CXCR4 receptor. In other preferred embodiments, the antibody or a fragment thereof that binds to the CXCR4 receptor inhibits the activity of the receptor. Accordingly, the antibody or fragment thereof disrupts the homing and maintenance of hematopoietic stem cells within the BM microenvironment and/or increases mobilization of cells from the BM to the periphery, and thereby increases the sensitivity of hematopoietic cancer cells to chemotherapeutic agents. In other preferred embodiments, the anti-CXCR4 antibody or fragment thereof induces apoptosis of a CXCR4-expressing cell. Apoptosis of target cancer cells permits use of the antibody as monotherapy.

In certain embodiments, the antibody or fragment thereof is a chimeric, humanized, or human antibody or a fragment thereof. In preferred embodiments, the antibody or fragment thereof is a human antibody or a fragment thereof. In other preferred embodiments, the antibody or fragment thereof comprises the CDR1, CDR2 and CDR3 domains in a heavy chain variable region comprising consecutively linked amino acids, the sequence of which is set forth in SEQ ID NO: 25, and the CDR1, CDR2 and CDR3 domains in a light chain variable region comprising consecutively linked amino acids, the sequence of which is set forth in SEQ ID NO: 29.

In certain embodiments, according to an delineation of CDR sequences by the Kabat system, the anti-CXCR4 antibody or fragment thereof comprises a heavy chain variable region CDR1 comprising consecutively linked amino acids, the sequence of which is set forth in SEQ ID NO: 1, a heavy chain variable region CDR2 comprising consecutively linked amino acids, the sequence of which is set forth in SEQ ID NO: 5, a heavy chain variable region CDR3 comprising consecutively linked amino acids, the sequence of which is set forth in SEQ ID NO: 9, a light chain variable region CDR1 comprising consecutively linked amino acids, the sequence of which is set forth in SEQ ID NO: 13, a light chain variable region CDR2 comprising consecutively linked amino acids, the sequence of which is set forth in SEQ ID NO: 17, and a light chain variable region CDR3 comprising consecutively linked amino acids, the sequence of which is set forth in SEQ ID NO: 21.

In other embodiments of the present methods, the anti-CXCR4 antibody or fragment thereof comprises a heavy chain variable region comprising consecutively linked amino acids having the sequence set forth in SEQ ID NO: 25 and a light chain variable region comprising consecutively linked amino acids having the sequence set forth in SEQ ID NO: 29. In preferred embodiments, the anti-CXCR4 antibody or fragment thereof is an IgG1 or IgG4 antibody or a fragment thereof. In more preferred embodiments, the antibody or fragment thereof is BMS-936564 or a CXCR4-binding fragment thereof.

Cancers amenable to the methods of treatment described herein include solid tumors and hematological malignancies. In certain embodiments, the solid tumor is selected from breast, ovarian, prostate, non-small cell lung, pancreatic, thyroid, colorectal, and kidney cancer, nasopharyngeal carcinoma, melanoma, renal cell carcinoma, neuroblastoma, glioblastoma, rhabdomyosarcoma, and osteosarcoma. In other embodiments, the hematologic malignancy is selected from multiple myeloma, acute myeloid lymphoma, non-Hodgkin's lymphomas, chronic lymphoid leukemia, follicular lymphoma, diffuse large B-cell lymphoma, Burkitt's lymphoma, immunoblastic large cell lymphoma, precursor B-lymphoblastic lymphoma, mantle cell lymphoma, acute lymphoblastic leukemia, mycosis fungoides, anaplastic large cell lymphoma, and precursor T-lymphoblastic lymphoma. In preferred embodiments, the hematologic malignancy is multiple myeloma, non-Hodgkin's lymphoma, diffuse large B-cell lymphoma, follicular lymphoma, acute myeloid lymphoma, acute lymphoblastic leukemia, or chronic lymphoid leukemia.

Multiple myeloma (MM) is a plasma cell malignancy characterized by the accumulation of malignant, immunoglobulin secreting, plasma cells within the bone marrow, which can lead to bone destruction, marrow failure, renal impairment, and peripheral neuropathy. The median survival after conventional treatments is 3-4 years and can be extended to 5-7 years with high-dose treatment followed by autologous hematopoietic stem-cell transplantation (HSCT) (Raab et al., 2009).

Currently approved regimens commonly used for MM include melphalan-based regimens for induction, and bortezomib (VELCADE®) or immunomodulatory drugs (IMiDs) including thalidomide or lenalidomide (REVLIMID®)-based regimens for induction and for subjects in relapse. For subjects with relapsed or refractory MM, treatment options include HSCT, repeat of previous chemotherapy treatment regimen, or a new regimen. HSCT is associated with a higher risk of treatment related morbidity. Furthermore, some subjects are not eligible for HSCT, due to poor performance status or comorbidities. There is currently no cure, and current therapies can only slow disease progression, prolong survival, and minimize symptoms. Nearly all MM subjects who survive their initial therapy relapse or become refractory, regardless of the line of therapy, and require further therapy (Jemal et al., 2005). Therefore, there is significant unmet medical need for subjects with MM. In a preferred embodiment of the present treatment methods, the hematologic malignancy is multiple myeloma, including relapsed or refractory MM.

Acute myeloid leukemia (AML) is the most common acute leukemia in adults, accounting for 80% of cases. Over 13,000 patients in the U.S. are diagnosed with AML per year, with over 8,820 deaths (*Cancer Facts* and Figures, 2008). Treatment for adult AML includes induction chemotherapy to achieve remission and post-remission chemotherapy (with or without stem cell transplantation) to avoid relapse. Remission induction rates range from 50% to 85%. Disease recurs in a majority of subjects. Treatment of relapsed AML is associated with relatively low remission rates with few patients deriving durable benefit (Breems et al., 2005).

Current options for treating adults with relapsed or refractory AML include chemotherapy and HSCT. Allogeneic HSCT is considered the treatment of choice for primary induction failure or beyond first complete remission (CR) and results in long term disease-free survival in only about 20% of patients. However, HSCT is not appropriate or available to a large number of patients for various reasons (e.g., early relapse, inaccessibility of transplant facility). This, together with the facts that patients who have relapsed or are refractory to conventional chemotherapy have poorer prognoses and responses to chemotherapy compared with those with newly diagnosed acute leukemia, requires that novel, targeted agents need to be developed for this patient population. In a preferred embodiment of the present treatment methods, the hematologic malignancy is acute myeloid leukemia, including relapsed AML.

Chronic lymphocytic leukemia (CLL) is the most common leukemia in Western countries and accounts for 30% of all leukemias in the U.S. Approximately 14,570 new cases of CLL will be diagnosed in 2011 (Siegel et al., 2011), and 4,400 patients will die. The disease is characterized by a progression of functionally incompetent, monoclonal lymphocytes, leading to lymphadenopathy, splenomegaly, hepatomegaly, and a prominent lymphocytosis in the peripheral blood and bone marrow. Most CLL patients initially demonstrate a complete or partial remission to chemotherapy, but with the exception of those treated by HSCT, nearly all relapse following discontinuation of treatment or develop refractory disease. Current initial treatment for CLL includes conventional chemotherapy and/or monoclonal antibody (rituximab) therapy. Survival for most patients is 5-10 years with increasing morbidity over time. For patients with relapsed/refractory CLL, the current treatment options do not cure the disease and there is an estimated median survival of 16 months. In a preferred embodiment of the present treatment methods, the hematologic malignancy is chronic lymphocytic leukemia, including relapsed CLL.

Follicular lymphoma (FL) is the second most common lymphoma in the United States and Western Europe, accounting for about 20% of NHL (overall), and the majority of low-grade lymphomas. Despite the fact that most patients respond to initial therapy (with about 40-80% complete remission), depending upon the regimen used, nearly all patients later develop progressive disease. Also, up to 10% are refractory to their initial treatment. Therefore, new, more effective therapies are needed. In a preferred embodiment of the present treatment methods, the hematologic malignancy is follicular lymphoma, including relapsed FL.

Diffuse large B-cell lymphoma (DLBCL) is the most common type of NHL, accounting for 25-30% of adult cases (40% of NHL among patients more than 75 years old). DLBCL has several subtypes, including but not limited to germinal center B (GCB) type, activated B-cell type (ABC) and primary mediastinal (Gisselbrecht et al., 2011). The 3-year overall survival (OS) for GCB and ABC in treated patients is 84% and 56%, respectively. Most DLBCL patients are not cured with conventional therapy. After relapse, while at least 60% of patients remain sensitive to conventional treatment, fewer than 10% have prolonged disease-free survival with second-line treatment regimens (Gisselbrecht et al., 2010). Relapsed or refractory (r/r) DLBCL is treated with chemotherapy (with or without rituximab) with the goal of subsequent high-dose chemotherapy and transplant, for the subset of patients with chemosensitive disease. Approximately 50% of responders to a second chemotherapy regimen followed by HSCT maintain their response at 2 years. For non-transplant candidates who fail second line therapy or who relapse post-transplant, therapy is palliative. Without transplant, chemotherapy provides short-term disease control in r/r DLBCL. Primary refractory patients are unlikely to achieve CR with a second chemotherapy regimen and following relapse, a second remission is usually not durable (Singer et al., 1986).

As DLBCL is initially a chemoresponsive disease, adding an agent such as an anti-CXCR4 antibody of this disclosure to restore chemosensitivity is a sound strategy for treating this disease. In a preferred embodiment of the present treatment methods, the hematologic malignancy is diffuse large B-cell lymphoma, including relapsed or refractory DLBCL.

Prompted by data from HIV-1 studies showing CXCR4-mediated apoptosis by binding of HIV-1 envelope glycoprotein-gp120 to CXCR4 (Garg et al., 2006; Berndt et al., 1998), the ability of an anti-CXCR4 antibody of the disclosure, BMS-936564, to induce apoptosis of CXCR4-expressing cell lines was measured. BMS-936564-induced apoptosis was demonstrated in over 20 different CXCR4-expressing cell lines (see Example 11, and Tables 3 and 4), confirming that this mechanism is not restricted to one cell type.

Apoptosis was also demonstrated in an in vitro model of minimal residual disease (MRD) for chronic lymphocytic leukemia (Kashyap et al., 2012). Eradication of MRD is one of the most challenging goals of treatment of CLL. In this MRD model, which is based on coculture of stromal cells that express and secrete CXCL12 and provide survival support to primary leukemia cells from CLL patients, CLL cells exhibited increased viability (20-60% at 48 hours) and showed resistance to chemotherapy agents. However, nanomolar concentrations (2-200 nM) of BMS-936564 induced cell death in CLL cells cultured alone as well as those incubated using the MRD model. The proapoptotic activity of BMS-936564 appeared to be P53 independent as apoptosis was observed in CLL cells from patients with 17p deletion and fludarabine resistance in vitro. BMS-936564 also inhibited CXCL12-mediated F-actin polymerization in CLL cells at lower concentrations than with AMD-3100, a small molecule CXCR4 inhibitor. These data suggest that BMS-936564 can effectively target CLL cells present in the tumor microenvironment in vivo that may contribute to MRD (Kashyap et al., 2012).

The apoptotic effect of the disclosed anti-CXCR4 antibodies, a property not exhibited by small-molecule CXCR4 antagonists, e.g., AMD3100, indicates that these antibodies can be used alone, as monotherapy, to treat patients with cancer. Previous studies on the effect of CXCR4 antagonists in in vivo AML and MM tumor models have suggested that these antagonists are effective in enhancing the sensitivity of the tumors cells to chemotherapy (Azab et al., 2009; Zeng et al., 2009). In contrast, the data presented herein in the Examples demonstrate that a statistically significant tumor growth inhibition was achieved when BMS-936564 was administered as monotherapy in a wide variety of AML, NHL and MM models. Accordingly, in certain embodiments of the present treatment methods, the anti-CXCR4 antibody or fragment thereof is administered as monotherapy. In preferred embodiments, the antibody or fragment thereof induces apoptosis of a CXCR4-expressing cell. Accordingly, this disclosure provides a method of inducing apoptosis of CXCR4-expressing cancer cells, including cells of the majority of hematological malignancies, comprising administering to a subject afflicted with the cancer, a therapeutically effective amount of an antibody or a fragment thereof that binds specifically to a CXCR4 receptor expressed on a cell surface.

Since BMS-936564 is an $IgG_4$ antibody, the in vivo efficacy cannot be explained by ADCC or CDC. However, it is possible that the antibody, once bound to CXCR4-expressing cells, engages FcγR1 receptors expressed on antigen presenting cells leading to phagocytosis. The cell lines, in which BMS-936564 efficacy was observed in vivo, required a secondary anti-Fc antibody to BMS-936564 to induce apoptosis in vitro (Example 11). This may be a consequence of lower expression of CXCR4 on those particular cell lines. If the mechanism of apoptosis initiation is dependent upon bringing CXCR4 molecules into close proximity, and the density of CXCR4 on the cell surface is low relative to the binding distance spanned by the anti-CXCR4 antibody, then a secondary high-affinity anti-Fc antibody may be required to bridge that gap, bringing the receptors together to drive an apoptotic signal. In vivo, this may be accomplished through FcγR1 receptors.

The data described herein suggest a novel mechanism of action, involving apoptosis of CXCR4-expressing target cells, for an anti-CXCR4 antibody in addition to its role in cellular mobilization. These data indicate that BMS-936564 may provide effective therapy for hematologic malignancies including MM, AML, and various NHLs, such as FL and DLBCL, as well as for solid tumor malignancies. However, the present methods are not necessarily limited to any particular mechanism of action of the anti-CXCR4 antibodies of the disclosure. For example, CXCR4 may modulate the epithelial to mesenchymal transition (EMT) in MM cells and the anti-CXCR4 antibodies of this disclosure may inhibit EMT, as evidenced by the demonstration that BMS-936564 inhibits the EMT-related proteins Twist, Snail and Slug, and up-regulates E-Cadherin (Roccaro et al., 2012). These data corroborate the view that CXCR4 may represent a valid therapeutical target due to its ability to modulate EMT.

It has previously been shown the CXCR4/CXCL12 axis plays a major role in homing and trafficking of MM cells to the BM, and disruption of the interaction of tumor cells with the BM leads to enhanced sensitivity to therapeutic agents (Alsayed et al., 2007; Azab et al., 2009). These findings suggest that the novel anti-CXCR4 human antibody, BMS936564, may prevent the homing and adhesion of MM cells to the BM and sensitize these cells to therapeutic agents. Notably, the validity of this basis for targeting CXCR4 is further substantiated by in vivo data reported by Roccaro et al. (2012) who used primary MM cells (CD138$^+$), MM cell lines (MM.1S, RPMI.8226), and primary MM bone marrow stromal cells (BMSCs) to evaluate migration towards CXCL12 and BMSCs. Cytotoxicity and DNA synthesis were measured by MTT and thymidine uptake, respectively. An in vivo melanoma mouse model was used to validate the effect of anti-CXC4 on modulating tumor cell metastasis. It was demonstrated that (1) mice treated with BMS-936564 presented with a less MM cell dissemination to distant bone marrow niches, compared to vehicle-treated mice, supporting the hypothesis that CXCR4 may represent a crucial modulation of tumor cell dissemination; (2) in the melanoma xenograft model BMS-936564-treated mice exhibited a reduced number of metastasis compared to vehicle-treated mice; and (3) BMS-936564 functionally target MM cells in vitro in terms of migration, adhesion and survival (Roccaro et al., 2012).

It was further demonstrated that BMS936564 inhibited migration of MM cells toward CXCL12 and primary MM BMSCs in a dose-dependent manner. Adhesion of primary MM cells to BMSCs was also inhibited by BMS936564 in a dose-dependent manner, while also inducing cytotoxicity on primary BM-derived CD138$^+$ cells. The BMS936564 antibody targeted MM cells in the context of BM milieu by overcoming BMSC-induced proliferation of tumor cells. In addition, BMS936564 synergistically enhanced bortezomib-induced cytotoxicity in MM cells (Roccaro et al., 2012). As described in Example 11, BMS936564-dependent activation of apoptotic pathways in MM cells was demonstrated by cleavage of caspase-9 and PARP. CXCL12-induced ERK-, Aid-, and Src-phosphorylation were inhibited by BMS936564 in a dose-dependent manner. Importantly, as described in Example 16, BMS936564 inhibited MM cell proliferation in vivo in xenograft mouse models.

In total, these data clearly demonstrate that targeting CXCR-4 on MM cells with an anti-CXCR4 antibody provides an effective means, probably employing multiple mechanisms, for treating cancer in general, and MM in particular.

The anti-CXCR4 antibodies of the disclosure can also be used in combination other cancer treatments, such as surgery and/or radiation, and/or can be co-administered with one or other more therapeutic agents, e.g., a cytotoxic agent, a radiotoxic agent or an immunosuppressive agent, which enhances or augments the therapeutic effect of the anti-CXCR4 antibodies. The antibody can be linked to the agent (as an immunoconjugate) or can be administered separate from the agent. In the latter case (separate administration), the antibody can be administered before, after or concurrently with the agent or can be co-administered with other known therapeutic agents, including conventional chemotherapeutic drugs and antibodies that bind tumor-associated antigens or immunoregulatory targets. Chemotherapeutic drugs include, among others, doxorubicin (adriamycin), cisplatin bleomycin sulfate, carmustine, chlorambucil, cyclophosphamide, lenalidomide, bortezomib, dexamethasone, mitoxantrone, etoposide, cytarabine, bendamustine, rituximab, ifosfamide, carboplatin, and etoposide. Co-administration of an anti-CXCR4 antibody, or antigen binding fragment thereof, of the present disclosure with chemotherapeutic agents provides two anti-cancer agents which operate via different mechanisms which yield a cytotoxic effect to human tumor cells. Such co-administration can solve problems due to development of resistance to drugs or a change in the antigenicity of the tumor cells that would render them unreactive with the antibody.

In other embodiments, the subject can be additionally treated with an agent that modulates, e.g., enhances or inhibits, the expression or activity of Fcγ or Fcγ receptors by, for example, treating the subject with a cytokine. Preferred cytokines for administration during treatment with the multispecific molecule include of granulocyte colony-stimulating factor (G-CSF), granulocyte-macrophage colony-stimulating factor (GM-CSF), interferon-γ (IFN-γ), and tumor necrosis factor (TNF).

The antibodies of this disclosure also can be used in combination with one or more additional therapeutic antibodies or other binding agents, such as Ig fusion proteins. Non-limiting examples of other antibodies or binding agents with which an anti-CXCR4 antibody of this disclosure can be administered in combination include antibodies or binding agents to CTLA-4, PSMA, CD30, IP-10, IFN-γ, CD70, PD-1, PD-L1, KIR, TNF, TNF-R, VEGF, VEGF-R, CCR5, IL-1, IL-18, IL-18R, CD19, CD52, CS1, EGFR, CD33, CD20, Her-2, CD25, gpIIb/IIIa, IgE, CD11a, α4 integrin, IFNα and IFNAR1.

There is growing evidence that disruption of the CXCR4 pathway, and disruption of the interaction between hematological cancer cells such as MM cells and their bone marrow microenvironment, confers greater sensitization to anti-cancer therapies, such as with lenalidomide and bortezomib for MM. As described in the Examples, nonclinical data on BMS-936564 as monotherapy and in combination with chemotherapy in MM cell lines and xenograft studies indicate that BMS-936564 is active in MM and may enhance the efficacy of regimens such as lenalidomide/dexamethasone and bortezomib. Preclinical studies have also shown that CXCR4 inhibition with AMD3100 leads to de-adhesion of MM cells from bone marrow stromal cells and mobilization of these cells into the periphery, which results in increased sensitivity to bortezomib (Azab et al., 2009). The anti-CXCR4 antibodies of the disclosure similarly potentiate the effect of chemotherapeutics by their ability to release malignant cells from the protective environment of the BM. In addition to mobilizing MM cells and increasing their chemosensitization, these antibodies have the additional effect of directly killing MM cells by apoptosis (Example 11), among other possible mechanisms. BMS-936564 has been shown to inhibit MM tumor growth in vivo when administered alone or in combination with lenalidomide or bortezomib (Example 16).

In certain embodiments of the therapeutic methods described herein, the method further comprises administering to the subject at least one chemotherapeutic agent in combination with the anti-CXCR4 antibody or fragment thereof. In certain embodiments, the cancer is MM and the at least one chemotherapeutic agent is lenalidomide plus low-dose dexamethasone, or bortezomib plus dexamethasone. These chemotherapy combinations are standard regimens that have proven therapeutic value in subjects with relapsed or refractory MM, and the safety profile of these chemotherapy agents is well characterized. In certain preferred embodiments, the anti-CXCR4 antibody is administered weekly, in Cycle 1 for the first two weeks as monotherapy, and then in combination with a chemotherapy regimen that includes lenalidomide plus low-dose dexamethasone, or bortezomib plus dexamethasone.

For example, for treatment of MM with BMS-936564 in combination with lenalidomide and dexamethasone, an exemplary dosage regimen comprises: (1) BMS-936564 (1, 3, or 10 mg/kg) administered as a single 60 minute IV infusion on Days 1, 8, 15, 22, 29 and 36 (Cycle 1) and on Days 1, 8, 15, and 22 (Cycle 2 and subsequent cycles); (2) lenalidomide (25 mg po) administered for 21 days (Days 15-35; Cycle 1) and Days 1-21 (Cycle 2 and subsequent cycles); and (3) dexamethasone (40 mg) administered on Days 15, 22, 29, and 36 (Cycle 1) and on Days 1, 8, 15, and 22 (Cycle 2 and subsequent cycles).

For treatment of MM with BMS-936564 in combination with bortezomib and dexamethasone, an exemplary dosage regimen comprises: (1) BMS-936564 (1, 3, or 10 mg/kg) administered as a single 60 minute IV infusion on Days 1, 8, 15, 22, and 29 (Cycle 1) and on Days 1, 8, and 15 (Cycle 2 and subsequent cycles); (2) Bortezomib (1.3 mg/m$^2$) administered as a 3-5 second IV push on Days 15, 18, 22, and 25 (Cycle 1) and on Days 1, 4, 8, 11 (Cycle 2 and subsequent cycles); and (3) dexamethasone (20 mg) administered on Days 15, 16, 18, 19, 22, 23, 25 and 26 (Cycle 1) and on Days 1, 2, 4, 5, 8, 9, 11 and 12 (Cycle 2 and subsequent cycles).

In certain embodiments, the cancer is AML and the at least one chemotherapeutic agent administered to a cancer patient in combination with the anti-CXCR4 antibody or fragment thereof of the disclosure is mitoxantrone, etoposide, and/or cytarabine, since this regimen is considered a standard-of-care regimen for relapsed, refractory AML patients (Amadori et al., 1991). In certain preferred embodiments, the anti-CXCR4 antibody is administered weekly, in Cycle 1 for the first two weeks as monotherapy, and then in combination with a chemotherapy regimen that includes mitoxantrone, etoposide, and cytarabine.

For example, for treatment of AML with BMS-936564 as monotherapy, an exemplary regimen comprises BMS-936564 (0.3, 1, 3, or 10 mg/kg) administered as a single 60-minute IV infusion on Day 1 in Cycle 1, and on Days 1, 8, and 15 in subsequent Cycles.

For treatment of AML with BMS-936564 in combination with chemotherapy, an exemplary dosage regimen comprises: (1) BMS-936564 administered on the first day of chemotherapy prior to the first dose of chemotherapy. BMS-936564 is administered on Days 1, 8 and 15 in Cycle 2 and subsequent cycles. In addition, for Cycles 2-13, chemotherapy consists of the following regimen (28-day Cycle): (2) mitoxantrone (8 mg/m$^2$ IV) over 15 minutes on Day 1 through 5; (3) etoposide (100 mg/m$^2$ IV) over 1 hour on Day 1 through 5; and (4) cytarabine (Ara-C; 1 g/m$^2$ IV) over 1 hour on Day 1 through 5.

In certain embodiments, the cancer is CLL or FL and the at least one chemotherapeutic agent administered to a cancer patient in combination with the anti-CXCR4 antibody or fragment thereof of the disclosure is bendamustine and/or rituximab. Preclinical studies indicate there is anti-tumor synergy between bendamustine and rituximab in several leukemia and lymphoma cell lines (Rummel et al., 2002) such that the latter sensitized B-cell lymphomas to apoptosis induced by chemotherapies, including bendamustine (Chow et al., 2002). The bendamustine plus rituximab (BR) combination has shown efficacy in lymphoma patients who are naive, pretreated or refractory to rituximab (Friedberg et al., 2008). In certain preferred embodiments, the anti-CXCR4 antibody is administered in combination with bendamustine and rituximab.

In preferred embodiments of a method for treating DLBCL, the anti-CXCR4 antibody is used in combination with rituximab, ifosfamide, carboplatin, and/or etoposide (Kewalramani et al., 2004). No chemotherapy regimen has shown superiority in relapsed or refractory DLBCL. R-ICE (rituximab, ifosfamide, carboplatin, and etoposide) is one of the most commonly used regimens in r/r DLBCL due to its comparable efficacy to other regimens and decreased toxicity relative to R-DHAP (dexamethasone, high-dose cytarabine, cisplatin) followed by high-dose chemotherapy and autologous HSCT for responding patients (Gisselbrecht et al., 2010). In certain preferred embodiments, the anti-CXCR4 antibody is administered in combination with rituximab, ifosfamide, carboplatin, and etoposide.

For example, for treatment of FL, DLBCL and CLL subjects with BMS-936564 as monotherapy, a preferred regimen comprises BMS-936564 (0.3-10 mg/kg) administered as a single 60-minute IV infusion on Day 1 in Cycle 1, and on Days 1, 8, 15, 22, 29, 36, 43 and 50 in subsequent cycles.

When administered in combination with chemotherapy for treatment of CLL, FL, and DLBCL subjects, an exemplary embodiment comprises administration of BMS-936564 on the first day of chemotherapy prior to the first dose of chemotherapy, and administration of chemotherapy at least 1 hour after completion of the infusion of BMS-936564. BMS-936564 is administered on Days 1 and 8 in Cycle 2 and subsequent Cycles.

Chemotherapy for CLL consists of the following regimen (28-day Cycle): rituximab (375 mg/m$^2$ IV) on Day 1 of Cycle 2 and subsequent cycles, then 500 mg/m$^2$ on Day 1 of subsequent cycles; and bendamustine (70 mg/m$^2$ IV) over 60 minutes on Day 1 of Cycle 2.

Chemotherapy for FL consists of the following regimen (28-day Cycle): rituximab (375 mg/m$^2$ IV) on Day 1 of Cycle 2 and subsequent cycles, then 500 mg/m$^2$ on Day 1 of subsequent cycles; and bendamustine (90 mg/m$^2$ IV) over 60 minutes on Day 1 of Cycle 2.

Chemotherapy for DLBCL consists of the following regimen (28-day Cycle): rituximab (375 mg/m$^2$ IV) on Day 1 of Cycle 2 and subsequent cycles; ifosfamide (5000 mg/m$^2$) continuous IV infusion, on Day 4, along with Mesna (2-mercaptoethane sulfonate Na; 5000 mg/m$^2$) continuous IV infusion over 24 hr, starting on Day 4 of Cycle 2 and subsequent cycles; carboplatin (dosage to yield target AUC 5 mg/mL·min calculated by the Calvert formula; maximum dose=800 mg), on Day 4 of Cycle 2 and subsequent cycles; etoposide (100 mg/m$^2$ IV) daily on Days 3-5 of Cycle 2 and subsequent cycles.

One aspect of this invention is the use of any anti-CXCR4 antibody or antigen-binding portion thereof of the disclosure for the preparation of a medicament for treating a subject afflicted with a CXCR4$^+$ cancer. Uses of any anti-CXCR4 antibody or antigen-binding portion thereof of the disclosure for the preparation of medicaments are broadly applicable to the full range of cancers disclosed herein. In preferred embodiments of these uses, the cancers include hematological malignancies, such as relapsed or refractory multiple myeloma, relapsed acute myeloid lymphoma, relapsed chronic lymphocytic leukemia, relapsed follicular lymphoma or refractory diffuse large B-cell lymphoma. This disclosure also provides medical uses of any anti-CXCR4 antibody or antigen-binding portion thereof of the disclosure corresponding to all the embodiments of the methods of treatment employing an anti-CXCR4 antibody described herein.

Also within the scope of the present disclosure are kits comprising any anti-CXCR4 antibody of antigen-binding fragment or composition thereof of this disclosure and instructions for use. Accordingly, this disclosure provides a kit for treating a cancer in a subject, the kit comprising (a) one or more doses of any of the anti-CXCR4 antibodies or CXCR4-binding fragment thereof of the disclosure and (b) instructions for using the anti-CXCR4 antibody or fragment thereof in any of the therapeutic methods described herein. For example, in certain embodiments the anti-CXCR4 antibody in the kit comprises the CDR1, CDR2 and CDR3 domains in a heavy chain variable region having the amino acid sequence set forth in SEQ ID NO: 25, and the CDR1, CDR2 and CDR3 domains in a light chain variable region having the amino acid sequence set forth in SEQ ID NO: 29. In preferred embodiments, the anti-CXCR4 antibody is BMS-936564. The kit can further contain one or more additional therapeutic reagents as described herein, such as an immunosuppressive reagent, a chemotherapeutic agent or a radiotoxic agent, or one or more additional antibodies that target different antigens.

Kits typically include a label indicating the intended use of the contents of the kit and instructions for use. The term label includes any writing, or recorded material supplied on or with the kit, or which otherwise accompanies the kit. In certain embodiments of a pharmaceutical kit, the anti-CXCR4 antibody may be co-packaged with other therapeutic agents in unit dosage form.

B. Viral Infections, Including HIV Infection

CXCR4 has been shown to be a coreceptor for HIV entry into T cells and, additionally, certain murine anti-CXCR4 antibodies have been demonstrated to be able to inhibit entry of HIV isolates into T cells (see Hou et al., 1998; Carnec et al., 2005). Thus, CXCR4 can be used as a receptor by viruses for entry into the cell and antibodies to CXCR4 can be used to inhibit cell entry of such viruses that use CXCR4 as a receptor. CXCR4-mediated apoptosis by binding of HIV-1 envelope glycoprotein-gp120 to CXCR4 has been reported (Garg et al., 2006).

Investigation revealed that antibodies cross-linked to CXCR4 could mimic the cell death observed with gp120-induction (Berndt et al., 1998), which suggested that the use of anti-chemokine receptor antibodies to prevent HIV-1 infection might result in efficient and rapid destruction of the receptor-expressing T-cells. Accordingly, the human anti-CXCR4 antibodies of this disclosure can be used to inhibit entry of a virus into a cell, wherein the virus uses CXCR4 as a receptor for cell entry, such that viral infection is inhibited. In a preferred embodiment, the antibodies are used to inhibit entry of HIV into T cells, e.g., in the treatment or prevention of HIV/AIDS. The antibody can be used alone or in combination with other anti-viral agents, such as anti-retroviral drugs such as AZT or protease inhibitors.

C. Inflammatory Conditions

The CXCR4/CXCL12 pathway has been shown to play a role in a variety of inflammatory conditions, including but not limited to inflammatory liver disease (Terada et al., 2003); autoimmune joint inflammation (Matthys et al., 2001); allergic airway disease (Gonzalo et al., 2000); and periodontal disease (Hosokawa et al., 2005).

Accordingly, the human anti-CXCR4 antibodies of this disclosure that inhibit binding of CXCL12 to CXCR4 can be used to inhibit inflammation in inflammatory disorders, including disorders selected from the group consisting of inflammatory liver disease, autoimmune joint inflammation, allergic airway disease, periodontal disease, rheumatoid arthritis, inflammatory bowel disease, systemic lupus erythematosus, Type I diabetes, inflammatory skin disorders (e.g., psoriasis, lichen planus), autoimmune thyroid disease, Sjögren's syndrome, pulmonary inflammation (e.g., chronic obstructive pulmonary disease, pulmonary sarcoidosis, lymphocytic alveolitis) and inflammatory kidney disease (e.g., IgA nephropathy, glomerulonephritis). The antibody can be used alone or in combination with other anti-inflammatory agents, such as non-steroidal anti-inflammatory drugs (NSAIDs), corticosteroids (e.g., prednisone, hydrocortisone), methotrexate, COX-2 inhibitors, TNF antagonists (e.g., etanercept, infliximab, adalimumab) and immunosuppressants (such as 6-mercaptopurine, azathioprine and cyclosporine A).

D. Angiogenesis

It has been demonstrated that CXCL12 induces neovascularization through recruitment of CXCR4-expressing hemangiocytes (Jin et al., 2006). Moreover, blockade of the CXCR4/CXCL12 pathway can attenuate in vivo tumor growth by inhibiting angiogenesis in a VEGF-independent manner (Guleng et al., 2005). Still further, as demonstrated in Example 7, antibodies of this disclosure are capable of inhibiting capillary tube formation in vitro. Accordingly, the anti-CXCR4 antibodies of this disclosure that inhibit binding of CXCL12 to CXCR4 can be used to inhibit angiogenesis by interfering with the CXCR4/CXCL12 pathway. Inhibition of angiogenesis can be used, for example, to inhibit tumor growth or tumor metastasis (regardless of whether the tumor is CXCR4$^+$). The antibody can be used alone or in combination with other anti-angiogenic agents, such as anti-VEGF antibodies.

E. Autologous Stem Cell Transplantation

Peripheral blood stem cells are the preferred source of stem cells for use in autologous stem cell transplantation, for example in the treatment of certain hematological malignancies. Collection of stem cells from the peripheral blood requires mobilization of CD34$^+$ stem cells from BM to the peripheral blood. Various cytokines, chemokines and adhesion molecules have been implicated in the regulation of this process (reviewed in Gazitt, 2001), including the interaction of CXCR4 and SDF-1. Moreover, a small molecule CXCR4 antagonist has been demonstrated to stimulate rapid mobilization of CD34$^+$ stem cells from the BM to the periphery (see, e.g., Devine et al., 2004; Broxmeyer et al., 2005; Flomenberg et al., 2005). Accordingly, anti-CXCR4 antibodies of this disclosure that inhibit CXCR4 activity (i.e., antagonist antibodies) can be used to stimulate mobilization of CD34$^+$ stem cells from the BM to the peripheral blood to allow for the use of such stem cells in transplantation (e.g., autologous transplantation), for example in the treatment of hematological disorders, such as multiple myeloma and non-Hodgkin's lymphoma. The antibody can be used alone or in combination with other agents used to stimulate mobilization of stem cells, such as G-CSF and/or GM-CSF. Thus, in another embodiment, the invention provides a method of stimulating mobilization of CD34$^+$ stem cells from BM to peripheral blood in a subject, the method comprising administering to the subject an anti-CXCR4 antibody of the invention such that mobilization of CD34$^+$ stem cells from BM to peripheral blood is stimulated. The method can further comprise collecting CD34+ stem cells from peripheral blood, such as for use in autologous stem cell transplantation.

The present invention is further illustrated by the following examples, which should not be construed as further limiting. The contents of all figures and all references, patents and published patent applications cited throughout this application are expressly incorporated herein by reference.

Example 1

Generation of Human Monoclonal Antibodies Against CXCR4 and CXCL12

Anti-CXCR4 human monoclonal antibodies were generated using a combination approach in which, first, transgenic transchromosomic mice expressing human antibody genes (Medarex KM MOUSE®, Milpitas, Calif., described in PCT Publication No. WO 02/43478 and U.S. Pat. No. 7,041,870) were immunized with human CXCR4-transfected R1610 cells to raise in the mice a repertoire of human immunoglobulins specific for human CXCR4 and then, second, a human antibody library was prepared from spleen cells of the mice and displayed on phage such that the phage were then screened for expression of variable region fragments having affinity for CXCR4 by panning with human CXCR4 incorporated into magnetic proteoliposomes (CXCR4-MPL). Variable region fragments of interest were recloned into a Fab expression vector and the Fab retested for antigen binding against transfected CXCR4-expressing cells. Fab clones F7 (since redesignated MDX-1338 or BMS-936564), F9, D1 and E2 were selected for further analysis. Whole antibodies were generated from the Fabs using standard molecular biology techniques. This combination approach is generally described in U.S. Pat. No. 6,794,132, and is specifically described in detail in WO 2008/060367.

To generate the anti-CXCL12 antibody, Medarex KM® transgenic mice were immunized with recombinant human CXCL12 (Peprotech, Rocky Hill, N.J.). Spleen lysates were pooled and processed as described previously (U.S. Pat. No. 6,794,132). Using proprietary phage display procedures, Biosite generated antibody fragments (Fab library). Phage which bound to CXCL12 were selected using biotinylated- CXCL12. Selected antigen-reactive Fabs were converted to full length IgG$_4$ (S228P) and re-expressed in CHO cells.

Isotype control antibody IgG$_4$ containing the S228P hinge mutation to reduce half-antibody formation (Angal et al., 1993) was produced at Biologics Discovery California, Sunnyvale, Calif.).

Example 2

Structural Characterization of Human Anti-CXCR4 Monoclonal Antibodies F7, F9, D1 and E2

The cDNA sequences encoding the heavy and light chain variable regions of the F7, F9, D1 and E2 Fab clones, obtained from phage display library screening as described in Example 1, were sequenced using standard DNA sequencing techniques.

The nucleotide and amino acid sequences of the heavy chain variable region of F7 are shown in FIG. 1A and in SEQ ID NO: 33 and 25, respectively. The nucleotide and amino acid sequences of the light chain variable region of F7 are shown in FIG. 1B and in SEQ ID NO: 37 and 29, respectively.

Comparison of the F7 heavy chain immunoglobulin sequence to the known human germline immunoglobulin heavy chain sequences demonstrated that the F7 heavy chain utilizes a $V_H$ segment from human germline $V_H$ 3-48, a D segment from the human germline 4-23, and a JH segment from human germline JH 6B. Further analysis of the F7 $V_H$ sequence using the Kabat system of CDR region determination led to the delineation of the heavy chain CDR1, CDR2 and CD3 regions as shown in FIG. 1A and in SEQ ID NOs: 1, 5 and 9, respectively. Comparison of the F7 light chain immunoglobulin sequence to the known human germline immunoglobulin light chain sequences demonstrated that the F7 light chain utilizes a $V_L$ segment from human germline $V_K$ L15 and a JK segment from human germline JK 1. Further analysis of the F7 $V_L$ sequence using the Kabat system of CDR region determination led to the delineation of the light chain CDR1, CDR2 and CD3 regions as shown in FIG. 1B and in SEQ ID NOs: 13, 17 and 21, respectively.

The nucleotide and amino acid sequences of the heavy chain variable region of F9 are shown in SEQ ID NO: 34 and 26, respectively. The nucleotide and amino acid sequences of the light chain variable region of F9 are shown in SEQ ID NO: 38 and 30, respectively. Comparison of the F9 heavy chain immunoglobulin sequence to the known human germline immunoglobulin heavy chain sequences demonstrated that the F9 heavy chain utilizes a $V_H$ segment from human germline $V_H$ 3-48, a D segment from the human germline 4-23, and a JH segment from human germline JH 6B. Further analysis of the F9 $V_H$ sequence using the Kabat system of CDR region determination led to the delineation of the heavy chain CDR1, CDR2 and CD3 regions as shown in SEQ ID NOs: 2, 6 and 10, respectively. Comparison of the F9 light chain immunoglobulin sequence to the known human germline immunoglobulin light chain sequences demonstrated that the F9 light chain utilizes a $V_L$ segment from human germline $V_K$ L15 and a JK segment from human germline JK 1. Further analysis of the F9 $V_L$ sequence using the Kabat system of CDR region determination led to the delineation of the light chain CDR1, CDR2 and CDR3 regions as shown in SEQ ID NOs: 14, 18 and 22, respectively.

The nucleotide and amino acid sequences of the heavy chain variable region of D1 are shown in SEQ ID NO: 35 and 27, respectively. The nucleotide and amino acid sequences of the light chain variable region of D1 are shown in SEQ ID NO: 39 and 31, respectively. Comparison of the D1 heavy chain immunoglobulin sequence to the known human germline immunoglobulin heavy chain sequences demonstrated that the D1 heavy chain utilizes a $V_H$ segment from human germline $V_H$ 3-48, a D segment from the human germline 4-23, and a JH segment from human germline JH 6B. Further analysis of the D1 $V_H$ sequence using the Kabat system of CDR region determination led to the delineation of the heavy chain CDR1, CDR2 and CD3 regions as shown in SEQ ID NOs. 3, 7 and 11, respectively. Comparison of the D1 light chain immunoglobulin sequence to the known human germline immunoglobulin light chain sequences demonstrated that the D1 light chain utilizes a $V_L$ segment from human germline $V_K$ L15 and a JK segment from human germline JK 1. Further analysis of the D1 $V_L$ sequence using the Kabat system of CDR region determination led to the delineation of the light chain CDR1, CDR2 and CD3 regions as shown in SEQ ID NOs. 15, 19 and 23, respectively.

The nucleotide and amino acid sequences of the heavy chain variable region of E2 are shown in SEQ ID NO: 36 and 28, respectively. The nucleotide and amino acid sequences of the light chain variable region of E2 are shown in SEQ ID NO: 40 and 32, respectively. Comparison of the E2 heavy chain immunoglobulin sequence to the known human germline immunoglobulin heavy chain sequences demonstrated that the E2 heavy chain utilizes a $V_H$ segment from human germline $V_H$ 3-48, a D segment from the human germline 4-23, and a JH segment from human germline JH 6B. Further analysis of the E2 $V_H$ sequence using the Kabat system of CDR region determination led to the delineation of the heavy chain CDR1, CDR2 and CD3 regions as shown in SEQ ID NOs: 4, 8 and 12, respectively. Comparison of the E2 light chain immunoglobulin sequence to the known human germline immunoglobulin light chain sequences demonstrated that the E2 light chain utilizes a $V_L$ segment from human germline $V_K$ L15 and a JK segment from human germline JK 1. Further analysis of the E2 $V_L$ sequence using the Kabat system of CDR region determination led to the delineation of the light chain CDR1, CDR2 and CD3 regions as shown in SEQ ID NOs: 16, 20 and 24, respectively.

Analysis of the framework sequences of the $V_H$ and $V_L$ regions of F7, F9, D1 and E2, as compared to the germline sequences from which they were derived, identified various framework amino acid residues that differed from germline. Certain framework residues in the N-terminal regions of the $V_H$ and $V_L$ segments were chosen for "back-mutation" to restore the framework residue to the germline sequence, because these non-germline residues in the N-terminal portion were encoded by the primers used to create the phage display libraries described in Example 1. In particular, the modified forms of the $V_H$ and $V_L$ segments of F7, F9, D1 and E2 (referred to as "GL" forms, for germline) were created using standard molecular biology techniques to substitute the germline amino acid residue at the indicated framework position. The specifically back-mutated amino acids, and alignments of the sequences of the GL variants with the sequences of the original variable regions of F7, F9, D1 and E2 are provided in WO 2008/060367.

The F7, F9, D1 and E2 Fab fragments are converted to full-length antibodies using standard recombinant DNA techniques. For example, DNA encoding the $V_H$ and $V_K$ regions of one of the Fab fragments can be cloned into an expression vector that carries the heavy and light chain constant regions such that the variable regions are operatively linked to the constant regions. Alternatively, separate vectors can be used for expression of the full-length heavy chain and the full-length light chain. Non-limiting examples of expression vectors suitable for use in creating full-length antibodies include the pIE vectors described in U.S. Pat. No.

7,674,618. The F7 (BMS-936564) Fab fragments were converted to a full-length IgG$_4$ (S228P) antibody and re-expressed in CHO cells.

Example 3

Binding Characteristics of Anti-CXCR4 Human Monoclonal Antibodies

In this example, binding characteristics of the anti-CXCR4 antibodies were examined by flow cytometry.

The human T cell line CEM, which expresses native human CXCR4 on its cell surface, was used to examine the ability of the F7, F9, D1 and E2 antibodies to bind to native, cell-surface CXCR4. Full-length F7, F9, D1 and E2 were titrated in a 1:3 serial dilution series, resulting in a concentration range from 300 nM to 5 pM. The antibodies were then mixed with CEM cells and allowed to bind before being detected with a FITC-conjugated anti-human IgG secondary antibody. The cells were then analyzed by fluorescence cytometry. The resulting mean fluorescence intensities are shown in the graph of FIG. 2, which demonstrates that all four anti-CXCR4 antibodies bind to CEM cells. The EC$_{50}$ for binding F7, F9, D1 and E2 were 21 nM, 14 nM, 80 nM and 290 nM, respectively.

Figure 3:
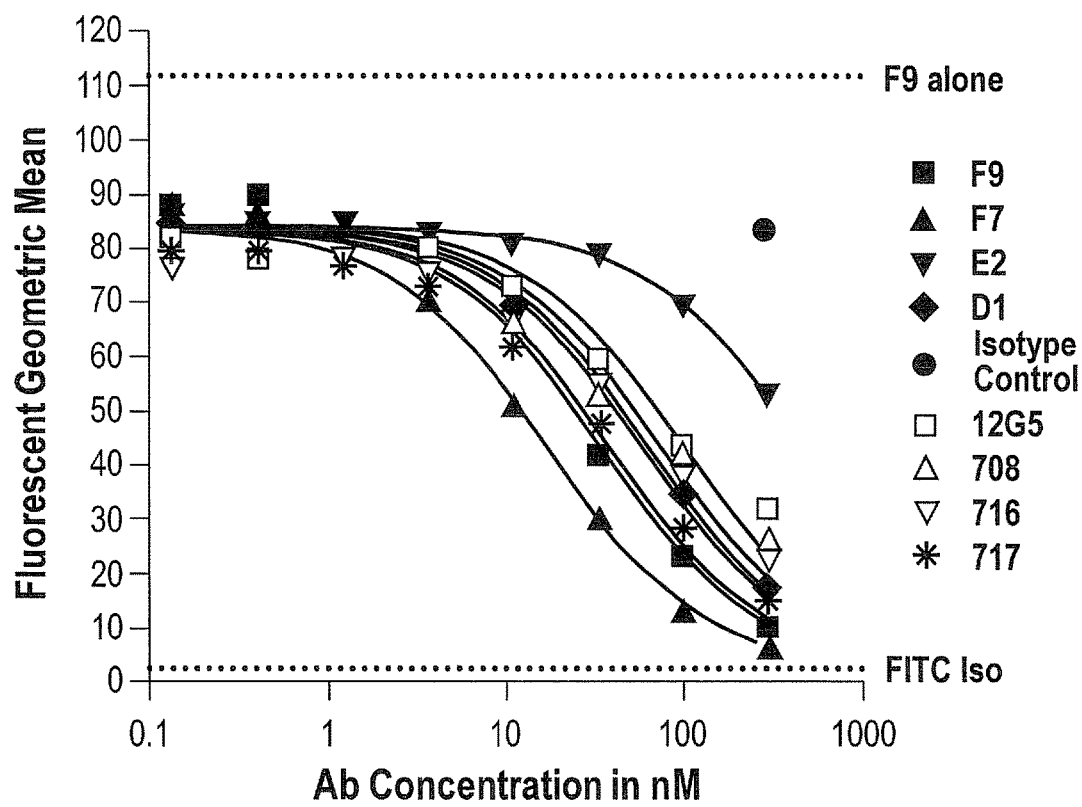
FIG. 3 shows antibody competition for binding to CEM cells between FITC-labeled anti-CXCR4 antibody F9 and a panel of unlabeled human anti-CXCR4 antibodies.

To determine the ability of a panel of anti-CXCR4 antibodies to compete for binding to CXCR4, competition studies were performed. The four human anti-CXCR4 antibodies F9, F7, E2 and D1 were used, along with four commercially available murine monoclonal anti-CXCR4 antibodies (12G5, 708, 716 and 717; R&D Systems catalog Nos. MAB170, MAB171, MAB172 and MAB173, respectively). The anti-CXCR4 antibodies were titrated in a 1:3 serial dilution series resulting in a concentration range from 300 nM to 5 pM in the presence of a constant concentration of FITC-labeled anti-CXCR4 antibody F9. The mixture of antibodies was then added to CEM cells and allowed to bind. The ability of each antibody to compete with F9 for binding to CEM cells was assessed by fluorescent cytometry and detection of FITC. The resulting mean fluorescent intensities are shown in the graph of FIG. 3, which demonstrates that all seven antibodies examined (F7, E2, D1, 12G5, 708, 716 and 717) were able to compete with F9 for binding to CEM cells, although the E2 antibody only demonstrated partial inhibition at high concentrations compared to the other antibodies.

In another set of experiments, the ability of the BMS-936564 mAb to bind to a variety of different cell lines was examined by flow cytometry by carrying out an FACS titration. Increasing amounts of mAb (from less than 0.001 µg/ml to more than 100 µg/ml) were incubated with 100,000 cells and binding assessed by flow cytometry. The Bmax value also was determined, which indicates approximately how many CXCR4 molecules are present on each cell. Based on the binding curves, an EC$_{50}$ for antibody binding was determined, the results of which are summarized below in Table 1.

TABLE 1

FACS Titration Results for F7 (BMS-936564)
Binding to Different Cell Lines

| Cell Type | EC$_{50}$ (µg/ml) | Bmax |
|---|---|---|
| Ramos | 0.48 | 106,000 |
| Raji | 0.34 | 52,536 |

TABLE 1-continued

FACS Titration Results for F7 (BMS-936564)
Binding to Different Cell Lines

| Cell Type | EC$_{50}$ (µg/ml) | Bmax |
|---|---|---|
| Namalwa | 1.57 | 116,000 |
| L540 | 3.69 | 31,868 |
| DMS79 | 3.99 | 24,587 |
| MDA-MB-231 | 9.24 | 14,186 |

Bmax = maximum binding (GMFI units)

The results show that the F7 mAb (BMS-936564) is capable of binding effectively to each of the six cell lines tested, with the lowest EC$_{50}$'s observed with the Ramos and Raji cell lines. These data also show that the expression of CXCR4 receptor is highest for Ramos and Namalwa cells and lowest for MDA-MB-231 cells and DMS79 cells.

In another binding experiment, the ability of the BMS-936564 mAb to bind to different subsets of human peripheral blood mononuclear cells (PBMCs) was examined. Human PBMCs were isolated by standard methods and different cellular subsets were isolated by FACS. In particular, the following cellular subsets were isolated: (i) CD3$^+$, (ii) CD20$^+$; (iii) CD11b$^+$ and (iv) CD14$^+$. Flow cytometry experiments conducted with the BMS-936564 mAb (at 33 µg/ml) demonstrated that it was capable of binding effectively to each of the four subsets, as compared to an isotype-matched control antibody.

Figure 4A:
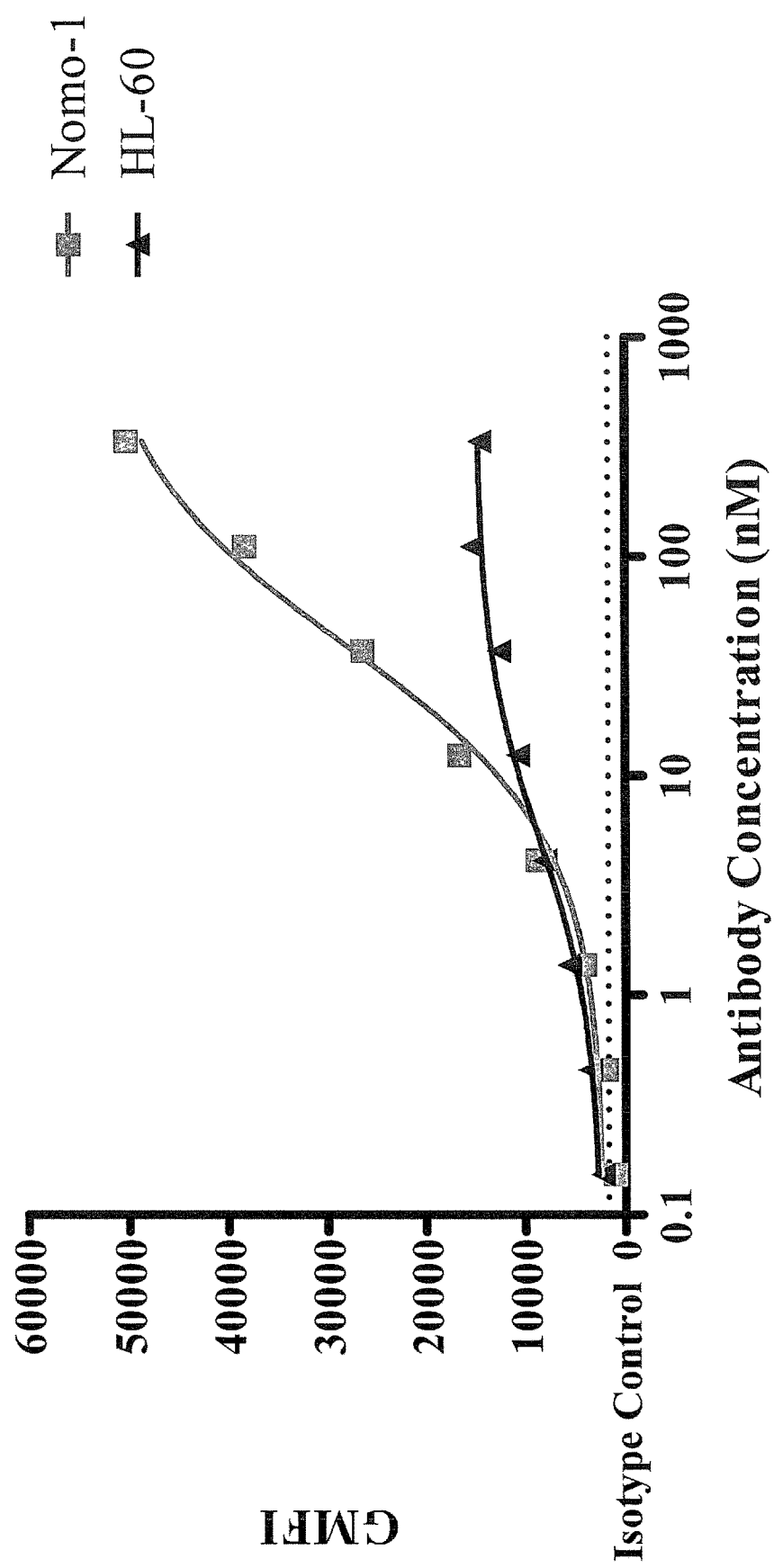
FIG. 4 shows a flow cytometric analysis of BMS-936564 binding. The antibody binds to AML cell lines Nomo-1 and HL-60 (A), CXCR4-transfected R1610, CEM and Ramos cell lines (B), MM cell lines, JJN-3R, and MOLP8 (C), and primary AML patient blood cells (D).
Figure 4B:
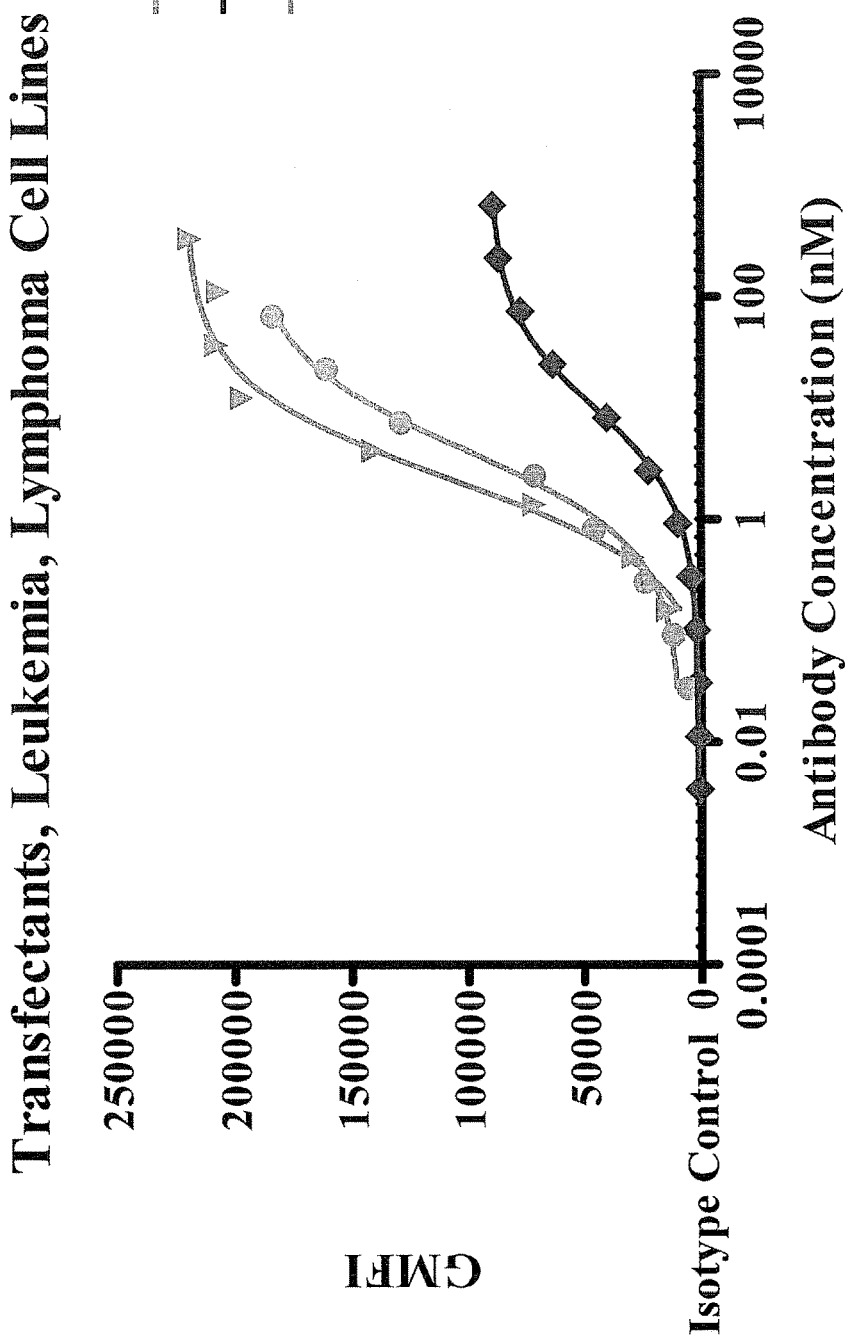
Figure 4C:
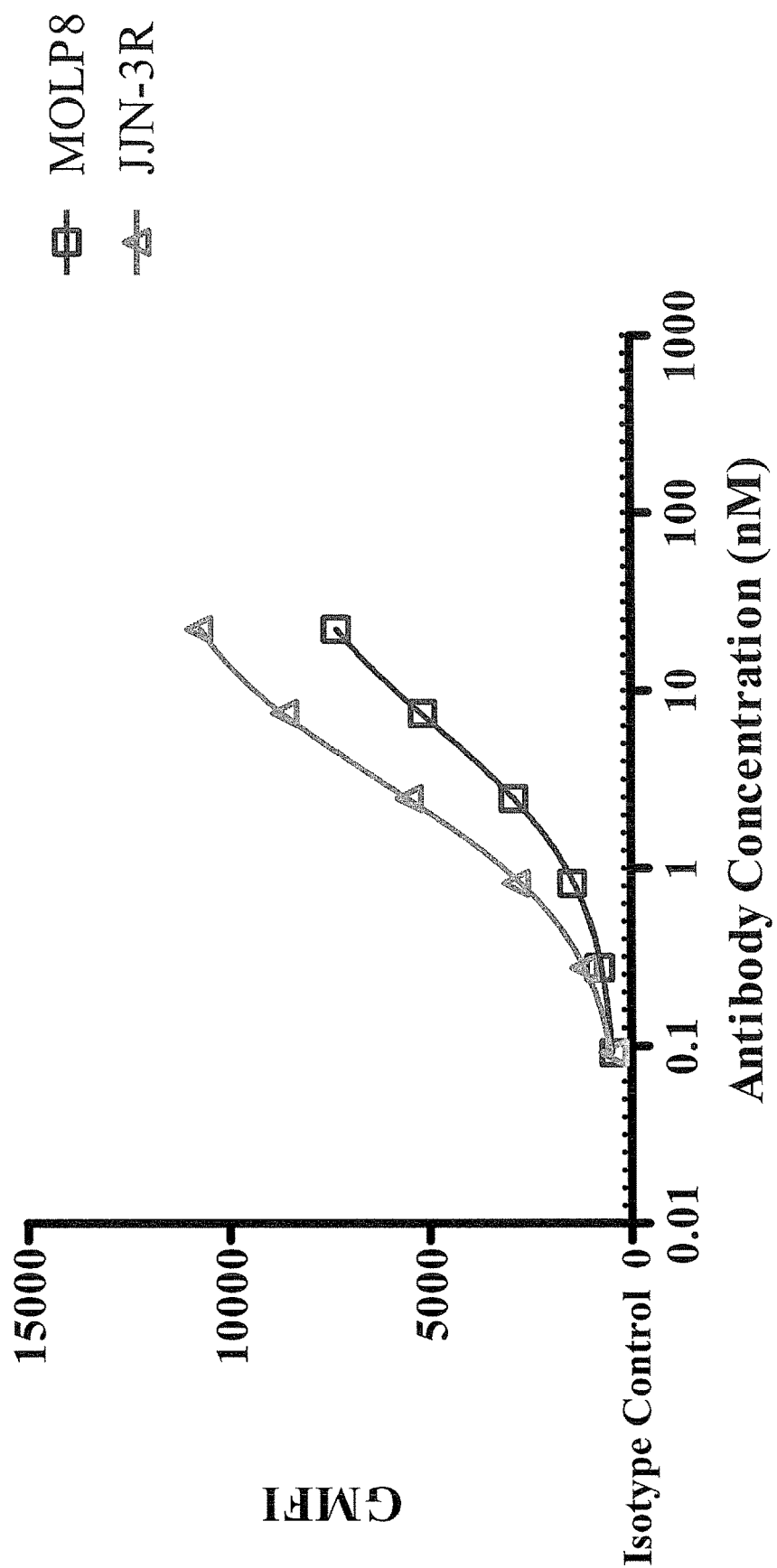
Figure 4D:
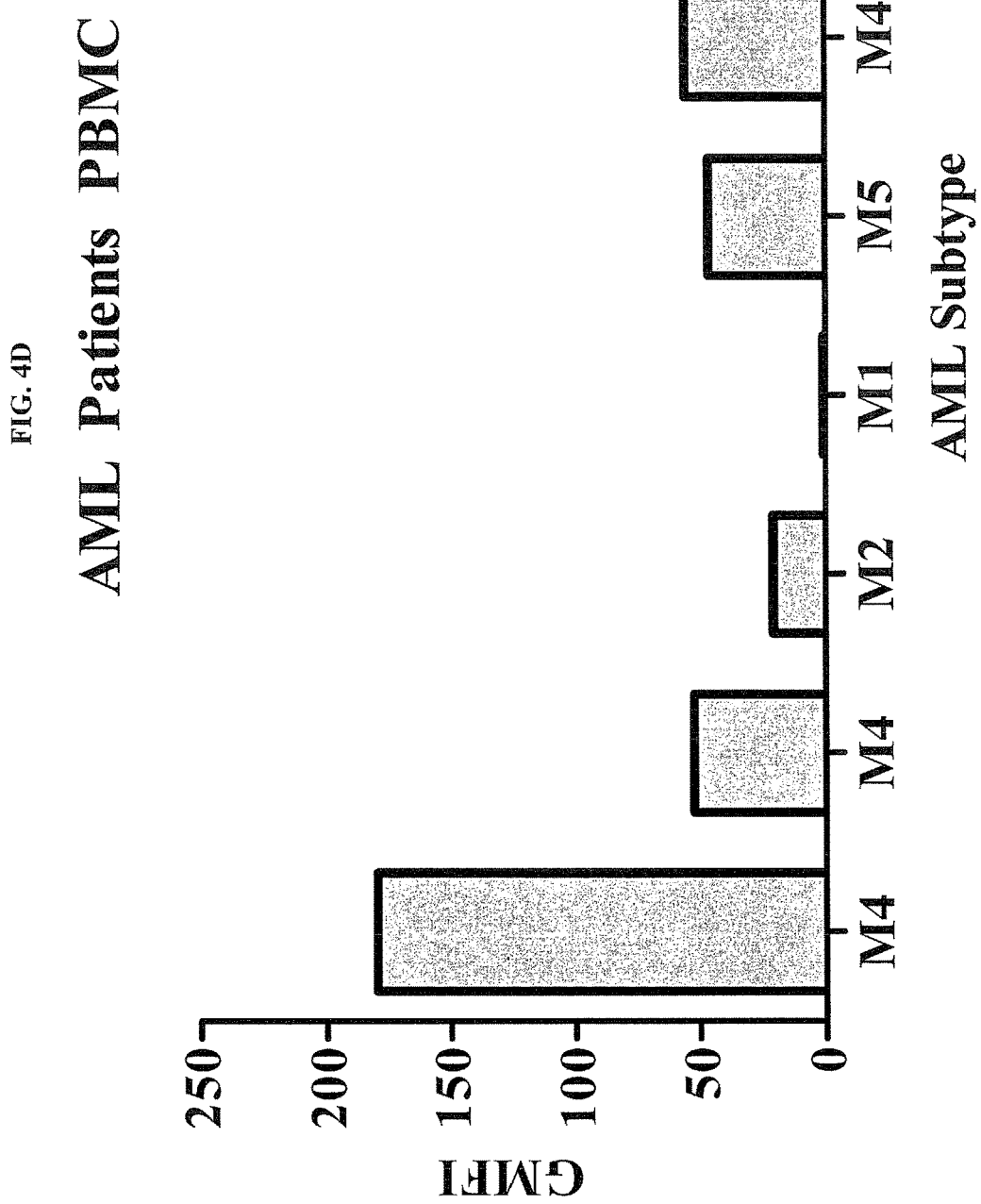

In another experiment, a different set of human CXCR4$^+$ cell lines were evaluated for BMS-936564 binding using flow cytometry. Cells were prepared for flow cytometry (FACS) staining by suspending cells with the indicated concentrations of naked BMS-936564 or biotinylated BMS-936564 before incubating the mixture of antibody and cells with goat anti-human FCγ-PE or PE-conjugated streptavidin. Cells were analyzed by FACS by gating on the live cell population identified by FSC and SSC. Dose-dependent binding was seen for the cell lines R1610-huCXCR4 (R1610 hamster fibroblasts transfected with human CXCR4 and kept under G418 selection); Ramos (human B lymphoblast Burkitt's lymphoma); CEM (human T lymphoblast acute lymphoblastic leukemia); Nomo-1 (human acute myeloid leukemia); HL-60 (human promyeloblast); MOLP8 (human MM); and JJN-3R (human MM cell line selected for resistance to bortezomib). See FIG. 4. No binding to the R1610 parental cells was detected. Based upon geometric mean fluorescent intensity (GMFI), CXCR4 levels were highest on R1610-huCXCR4 and Ramos cells followed by CEM (FIG. 4B), Nomo-1 and HL60 (FIG. 4A). The multiple myeloma cell lines MOLP-8 and JJN-3R expressed the lowest number of receptors (FIG. 4C). The EC$_{50}$ values for binding are shown in Table 2. In addition, BMS-936564 bound to healthy donor PBMCs (data not shown) as well as 7/8 PBMCs samples collected from AML patients with variable GMFI (FIG. 4D). These data indicate that CXCR4 is expressed on multiple hematopoietic cell lines and variably expressed in AML patients.

TABLE 2

Binding of BMS-936564 Binding to Human CXCR4$^+$ Cell Lines

| Cell Type | EC$_{50}$ (nM) |
|---|---|
| R1610-huCXCR4 | 2.3 |
| Ramos | 4.2 |
| CEM | 10.3 |

TABLE 2-continued

Binding of BMS-936564 Binding to Human CXCR4+ Cell Lines

| Cell Type | EC$_{50}$ (nM) |
|---|---|
| Nomo-1 | 40 |
| HL-60 | 5.3 |
| MOLP-8 | 6.5 |
| JJN-3R | 2.0 |

Example 4

Inhibition of CXCL12 Binding to CXCR4 by Anti-CXCR4 and Anti-CXCL12 Antibodies

To determine the ability of the anti-CXCR4 human antibodies to inhibit the binding of CXCL12 to CXCR4, a competition study was performed using $^{125}$I-labeled CXCL12 (PerkinElmer, Waltham, Mass.) and CEM cells, which naturally express CXCR4. A comparison of anti-CXCR4 antibodies on blocking CXCL12 binding to CEM cells was performed by a standard radio-labeled ligand binding assay. The anti-CXCR4 antibodies were serially diluted 1:3 to yield a range of concentrations from 300 nM to 137 pM. The antibodies were added to 750,000 CEM cells in 100 µl in the presence of 100 pM $^{125}$I-CXCL12 with a specific activity of 2000 Ci/mmole (Amersham, catalog #IM314-25UCI). An irrelevant antibody of the same isotype was used as a negative control. The total possible bound radio-labeled ligand was determined by allowing the $^{125}$I-CXCL12 to bind to CEM cells in the absence of antibodies for 2 hours at 4° C. Non-specific binding of the radio-labeled ligand was determined by allowing the $^{125}$I-CXCL12 to bind in the presence of 1 µM unlabeled CXCL12 (Peprotech, catalog #300-28A). The amount of cell-associated $^{125}$I-CXCL12 was determined by standard methods. The results are shown in FIG. 5, which demonstrates that the F7 antibody (BMS-936564) provides the most effective blockade of CXCL12 binding to CXCR4 expressed on CEM cells. The F9 and D1 antibodies also blocked CXCL12 binding, although more moderately than F7. The E2 antibody, although it does bind to CXCR4 on CEM cells (as demonstrated in Example 3), did not effectively block CXCL12 binding to CXCR4 on CEM cells. The EC$_{50}$'s for CXCL12 blockade by F7, F9 and D1 were 2.3 nM, 12.5 nM and 28.6 nM, respectively.

In another experiment, the blockade of binding of CXCL12 to CXCR4 by BMS-936564 and an anti-CXCL12 antibody was compared. Serial dilutions of BMS-936564, anti-CXCL12 and control antibody were tested for blockade of $^{125}$I-CXCL12 binding to CXCR4+ CEM cells. Competition of $^{125}$I-CXCL12 (PerkinElmer, Waltham, Mass.) binding to CXCR4 on CEM cells was demonstrated using a fixed concentration of $^{125}$I-CXCL12 (100 pM) and a titration of BMS-936564 from 5 pM to 300 nM. An isotype antibody was used as a negative control and unlabeled CXCL12 was used as a positive control. Plates were incubated at room temperature for 1 hour, the filters were washed, removed and counts per minute (CPM) were read by a PerkinElmer WIZARD® gamma counter (Waltham, Mass.). For all in vitro studies, the data were graphed and analyzed with GraphPad Prism software (San Diego, Calif.), using nonlinear regression and sigmoidal dose-response curves.

Figure 6A:
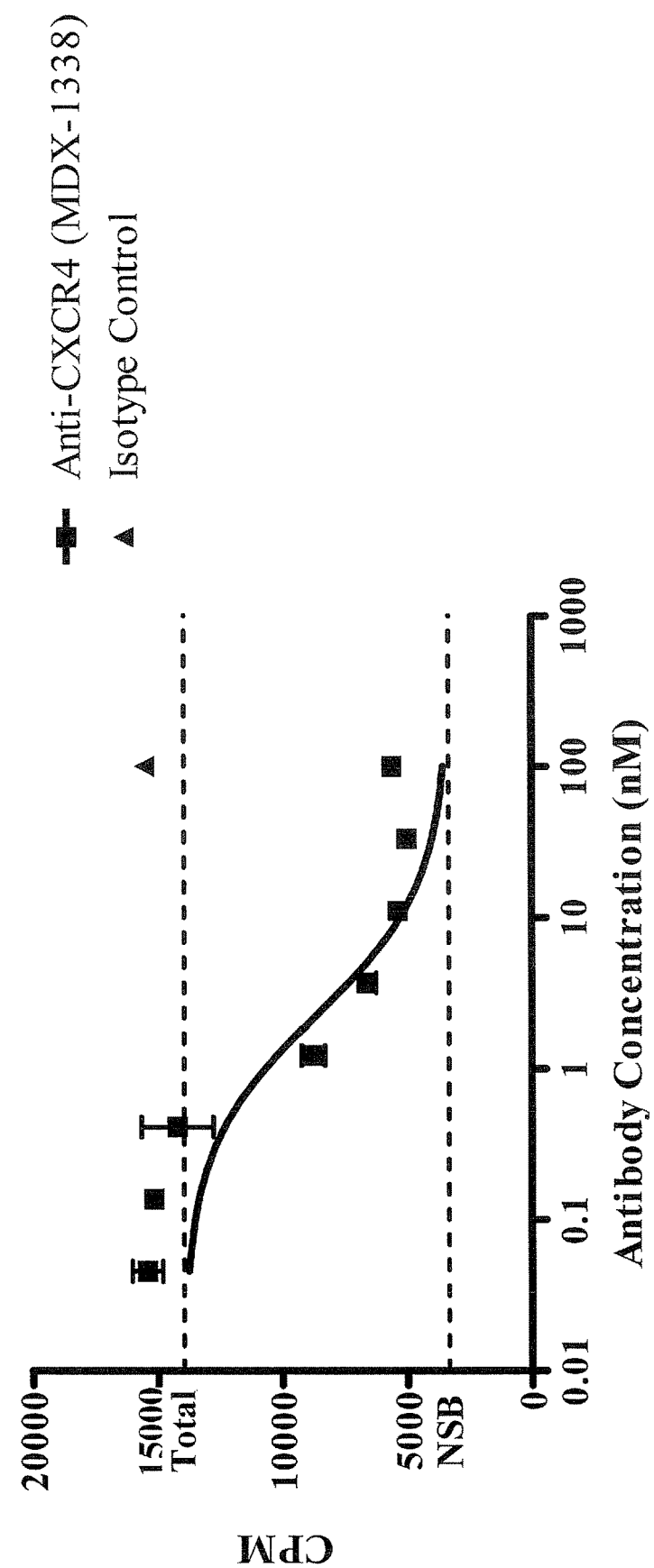
FIG. 6 shows inhibition of binding of $^{125}$I-labeled CXCL12 to CEM cells by anti-CXCR4 antibody MDX-1338 (BMS-936564) (A) or an anti-CXCL12 antibody (B), and inhibition of binding of $^{125}$I-labeled CXCL12 to Ramos cells by MDX-1338 (6C). Ligand binding assays were conducted by incubating 100 pM $^{125}$I-CXCL12 with CEM cells in the presence of increasing concentration of MDX-1338, anti-CXCL12, or isotype control antibody. Unlabeled CXCL12 was added at 1000-fold molar excess (100 nM) to establish non-specific binding (NSB). $^{125}$I-CXCL12 without antibody or unlabeled competitor was added to establish total achievable binding (Total).
Figure 6B:
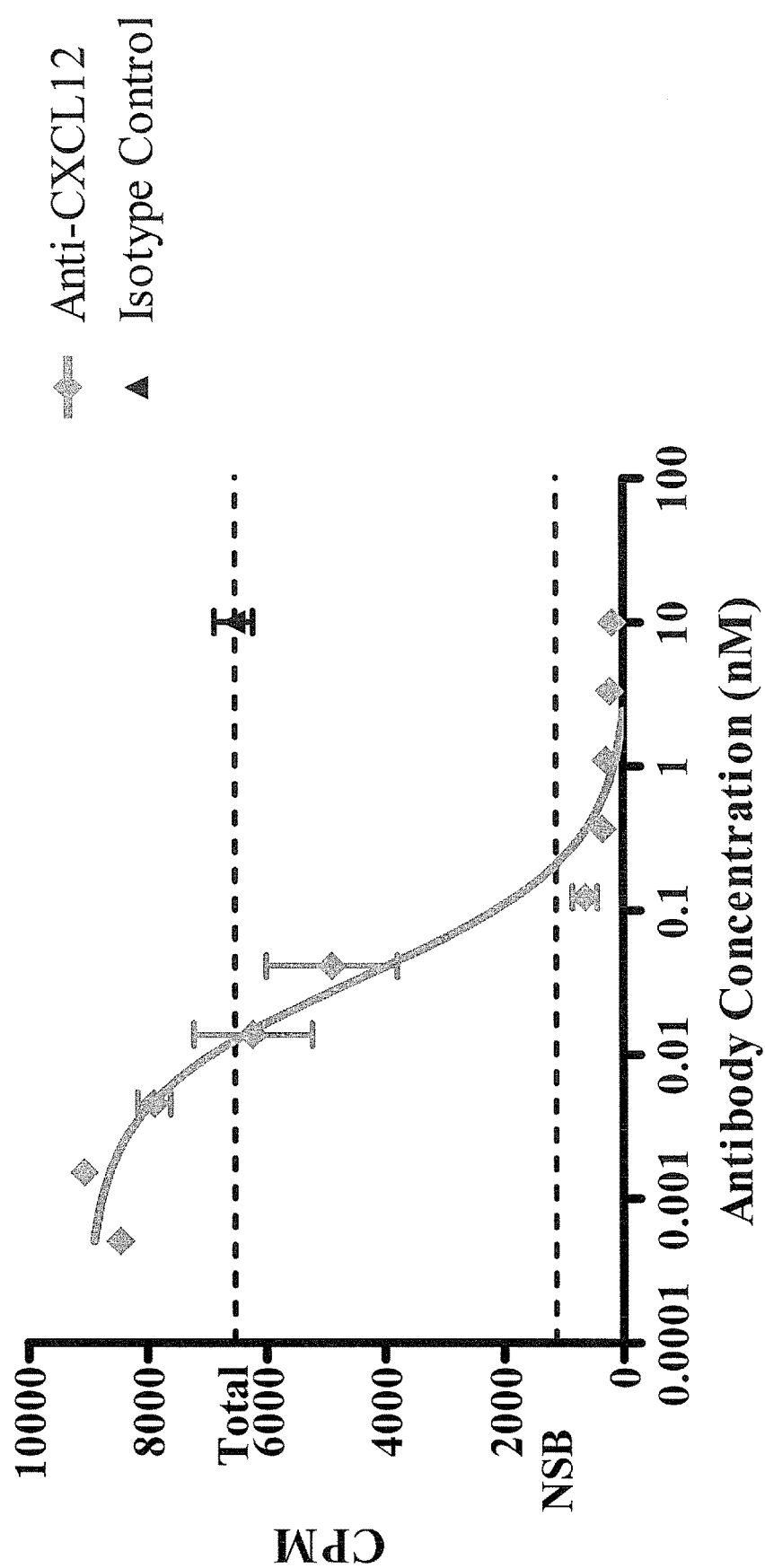

Saturation binding studies were conducted using radiolabeled CXCL12 and CXCR4$^{hi}$ CEM cells. The K$_D$ of $^{125}$I-CXCL12 binding to CEM cells was determined to be 4.3 nM (data not shown) which is similar to the reported K$_D$ of CXCL12 for CXCR4 ranging from 3.0 to 5.4 nM (DiSalvo et al., 2000). Using a suboptimal fixed concentration of $^{125}$I-CXCL12 (100 pM), BMS-936564 was titrated and dose-dependent inhibition of $^{125}$I-CXCL12 binding with an EC$_{50}$ value of approximately 2 nM was observed (FIG. 6A). Interestingly, the anti-CXCL12 antibody was more potent and induced a dose-dependent inhibition of $^{125}$I-CXCL12 binding to CEM cells with an EC$_{50}$ value of approximately 90 pM (FIG. 6B).

Figure 6C:
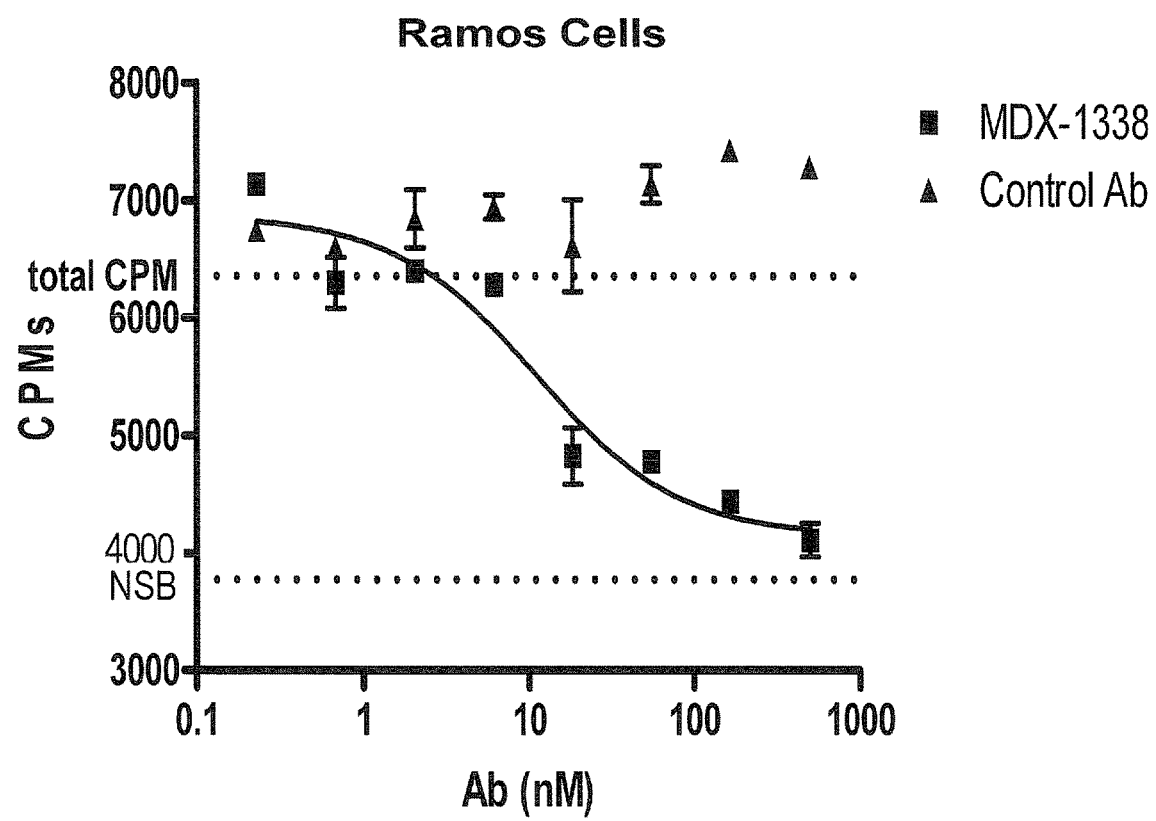

BMS-936564 was also shown to block $^{125}$I-CXCL12 binding to Ramos cells in a dose-dependent manner with an EC$_{50}$ value of approximately 11 nM (FIG. 6C).

Example 5

Inhibition of CXCL12-Induced Calcium Flux by Anti-CXCR4 and Anti-CXCL12 Antibodies To determine the ability of the anti-CXCR4 human antibodies to inhibit calcium flux in CEM cells induced by CXCL12, CEM cells were first labeled with the fluorescent dye Calcium 3 (Molecular Devices, Sunnyvale, Calif.). The anti-CXCR4 antibodies were titrated in a 1:3 serial dilution series resulting in a concentration range from 100 nM to 1 pM and allowed to bind to 200,000 CEM cells in 200 µl and incubated 10 minutes at room temperature prior to loading into a FLEXSTATION® machine (Molecular Devices). As a negative control, an irrelevant antibody of the same isotype was used. Cells were then stimulated with a final concentration of 50 nM recombinant human CXCL12α (Peprotech), added as 500 nM in a volume of 22 µl for a final volume of 222 µl. The resulting calcium flux was measured for 200 seconds per well. As a positive control, cells in the absence of antibody were stimulated with CXCL12α (made up in Hank's buffered saline (HBS) with 0.1% BSA or HBS) to achieve a maximum possible calcium flux signal. To determine a baseline, cells were stimulated with HBS with 0.1% BSA. The CXCL12α-stimulated release of calcium was measured by the development of calcium-dependent fluorescence over time. The area under the curve of the resulting fluorescence trace was reported as an indication of calcium flux. The resulting inhibition of calcium flux by the anti-CXCR4 antibodies is represented in FIG. 7. The data were plotted and the EC$_{50}$s were calculated using GraphPad Prism software and the non-linear curve fit, sigmoidal dose response formula. Antibodies F7 (BMS-936564), F9 and D1 inhibited CXCL12α-induced calcium flux. Although antibody E2 did bind to CXCR4 (as demonstrated in Example 3), it did not significantly inhibit CXCL12α-induced calcium flux. The EC$_{50}$'s for inhibition of CXCL12-induced calcium flux by F7, F9 and D1 were 0.90 nM, 0.32 nM and 0.57 nM, respectively.

Figure 8A:
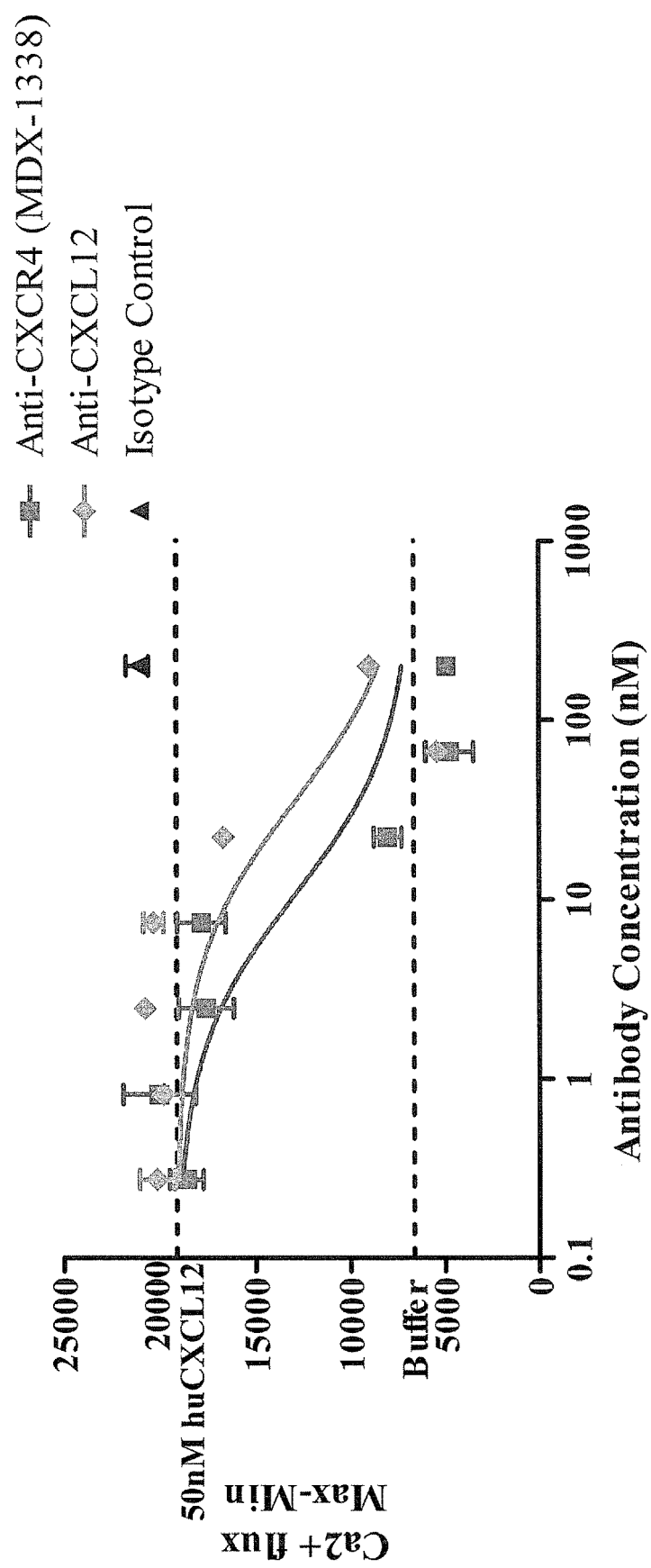
FIG. 8 shows inhibition of CXCL12-induced calcium flux in CXCR4$^+$ cells by anti-CXCR4 antibody MDX-1338 (BMS-936564) or an anti-CXCL12 antibody. Calcium flux assays were conducted by incubating either Ramos cells (A) or CEM cells (B) with Calcium 4 dye in the presence or absence of the test antibody or an isotype control. Dye-loaded cells were incubated at room temperature with 50 nM and 5 nM CXCL12 with the Ramos and CEM cells, respectively. The area under the curve of fluorescence between 20 to 200 seconds was quantitated and an $EC_{50}$ was calculated.
Figure 8B:
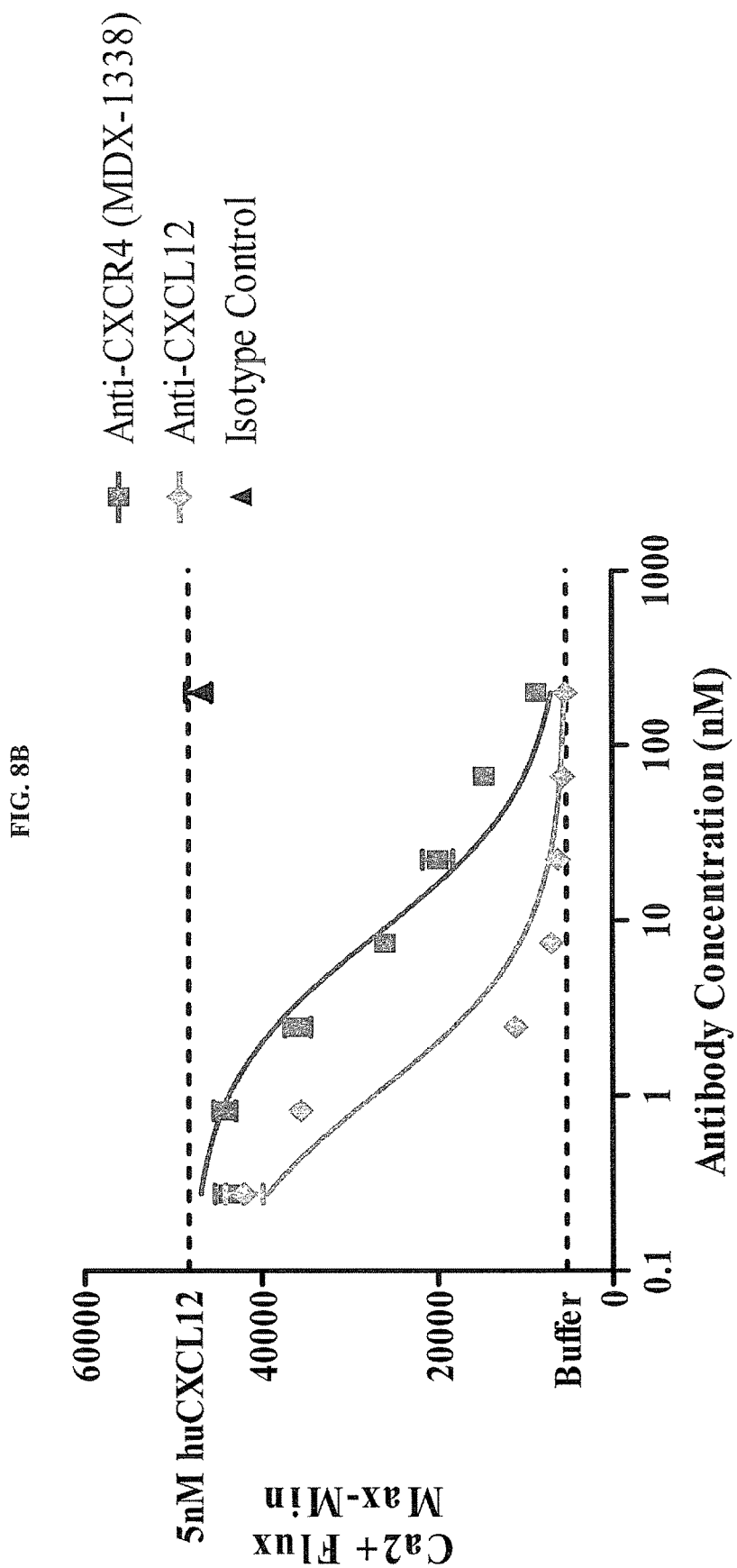

In another experiment, the capacity of BMS-936564 and anti-CXCL12 to inhibit CXCL12-induced calcium flux was compared. Ramos and CELL cells were loaded with FLIPR® Calcium 4 dye (Molecular Devices), and a fixed concentration of CXCL12 was used to stimulate calcium flux. A titration of BMS-936564 or anti-CXCL12 from 50 pM to 100 nM was used to inhibit the response. A maximal calcium response was set with CXCL12 minus antibodies. A baseline response was established with buffer stimulation of cells without CXCL12. Calcium fluxes were read on the FLEXSTATION® (Molecular Devices). CXCL12 was shown to induce a dose-dependent rise in intracellular calcium with peak calcium flux reached at 50 nM and 5 nM with Ramos and CEM cells, respectively. Using the optimal concentration of CXCL12 to stimulate calcium flux, a titration of BMS-936564 or anti-CXCL12 was used to inhibit the response (FIGS. 6C and 6D). Both BMS-936564 and anti-CXCL12 blocked CXCL12-induced calcium flux in a dose dependent manner. BMS-936564 blocked with an $EC_{50}$ of approximately 10 nM and 8 nM in Ramos and CEM, respectively (FIGS. 8A and 8B), whereas anti-CXCL12 blocked with an $EC_{50}$ of approximately 35 nM (Ramos) and 2 nM (CEM) cells (FIGS. 8A and 8B).

Example 6

Figure 9:
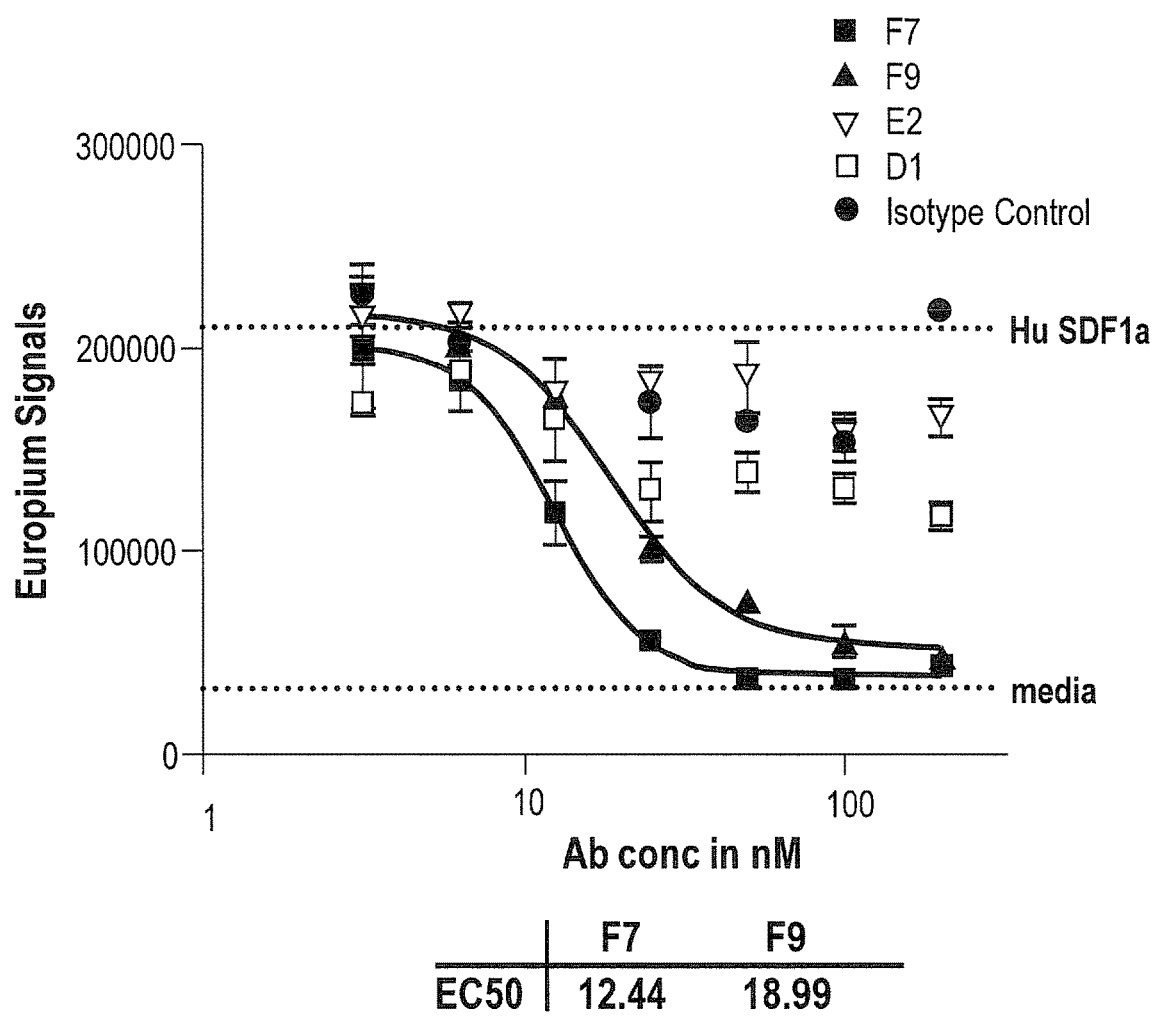
FIG. 9 shows inhibition of CXCL12-induced migration of CEM cells by anti-CXCR4 human antibodies F7 (BMS-936564) and F9, whereas antibodies D1 and E2 do not significantly inhibit migration.

Inhibition of CXCL12-Induced Migration of CEM Cells by Anti-CXCR4 and Anti-CXCL12 Antibodies To determine the ability of the anti-CXCR4 human antibodies to inhibit migration of CEM cells induced by CXCL12, CEM cells first were labeled with the BATDA (bis(acetoxymethyl)2,2':6',2''-terpyridine-6,6''-dicarboxylate) chemiluminescent migration reagent (PerkinElmer). The anti-CXCR4 antibodies were titrated in a 1:3 serial dilution series resulting in a concentration range from 100 nM to 1 pM and allowed to bind to labeled CEM cells at a density of 10 million cells per ml. As a negative control, an irrelevant antibody of the same isotype was used. Recombinant human CXCL12α (Peprotech) was added at 5 nM at 30 µl per well to the lower chamber of a 96 well Neuroprobe migration plate with 5.7 mm diameter filters per well. Each well contains 5 µM pores. Labeled CEM cells with and without antibody were loaded onto the filters at a concentration of 0.5 million cells per well in a volume of 50 µl. The migration plate was incubated at 37° C. for 2.5 hours. Migrated cells were captured in the lower chamber of the plate, lysed and detected with DELFIA® Europium detection solution (Perkin Elmer). The chemiluminescent signal was recorded on a Fusion instrument. The resulting inhibition of CXCL12α-induced migration by the anti-CXCR4 antibodies is shown in FIG. 9. The results demonstrated that antibodies F7 and F9 inhibited migration effectively, while antibodies D1 and E2 did not significantly inhibit migration. The $EC_{50}$'s for inhibition of CXCL12-induced CEM cell migration by F7 and F9 were 12.44 nM and 18.99 nM, respectively.

Figure 10A:
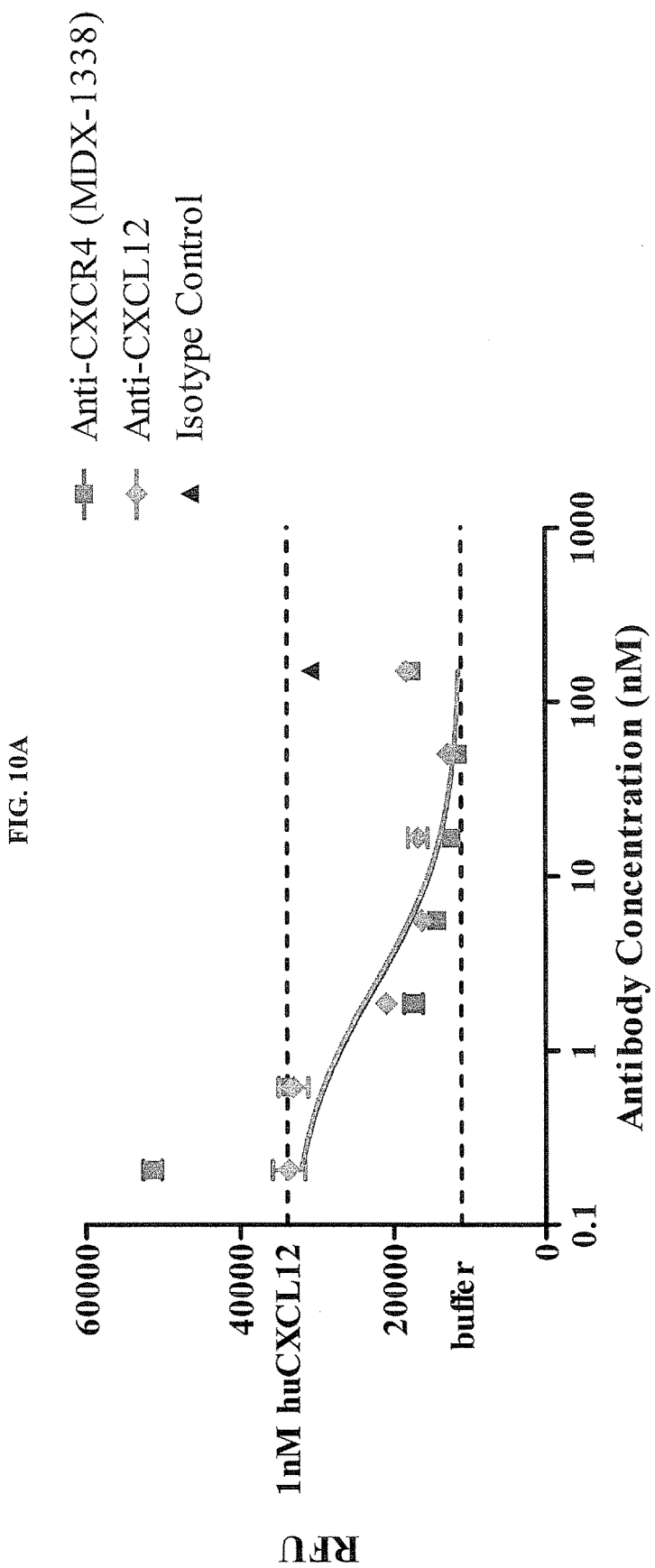
FIG. 10 shows inhibition of CXCL12-induced migration of CXCR4$^+$ cells by anti-CXCR4 antibody MDX-1338 (BMS-936564) or an anti-CXCL12 antibody. Migration assays with the Ramos (A) and CEM (B) cells was carried out in the presence of 1.25 nM and 0.05 nM CXCL12 respectively. The number of labeled cells, which had migrated into the lower compartment, was measured on a Fusion (PerkinElmer) plate reader. Each point represents n=3.
Figure 10B:
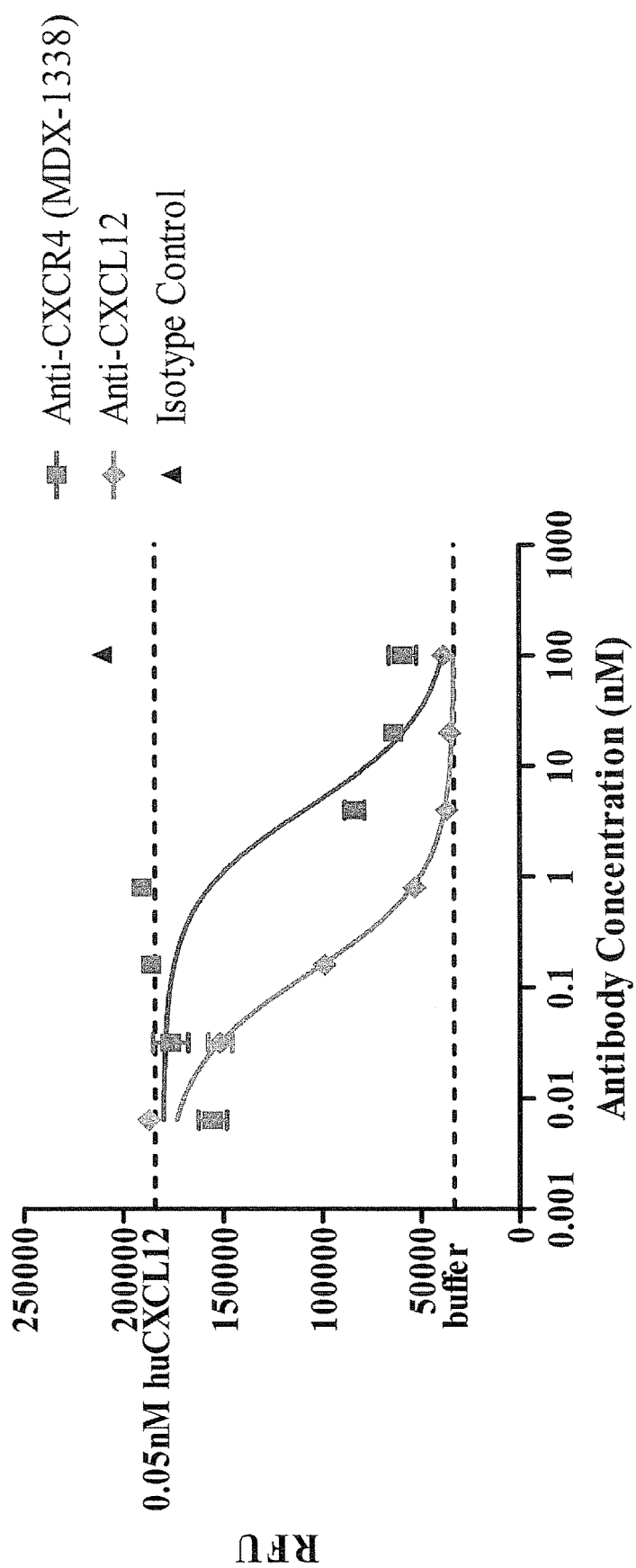

In another experiment, the ability of BMS-936564 and anti-CXCL12 to inhibit CXCL12-induced migration of Ramos and CEM cells was compared. Cells were loaded with BATDA. A fixed concentration of CXCL12 was used to stimulate migration of cells through a filter containing 5 µm pores on Migration Plates from Neuro Probe (Gaithersburg, Md.). A titration of BMS-936564 or anti-CXCL12 from 20 pM to 300 nM was added to the cells. CXCL12 without antibody was used to establish maximal migration. Migration toward media alone without CXCL12 was used to measure background migration. Following a 2-hour incubation at 37° C., migrated cells were detected by addition of DELFIA® Europium solution (Perkin Elmer) to the lysed cells and detected by time resolved fluorescence on the Fusion instrument. The optimal concentration of CXCL12 for inducing Ramos migration was established to be 10 ng/mL (1.25 nM) while CEM cells were more sensitive to CXCL12 and exhibited maximal migration at 0.05 nM CXCL12. BMS-936564 was shown to block CXCL12-induced migration with an approximate $EC_{50}$ value of 1 nM in Ramos cells and 4 nM in CEM cells (FIGS. 10A and 10B). Anti-CXCL12 inhibited CXCL12-induced migration with an approximate EC50 value of 0.9 nM (Ramos) and 0.13 nM (CEM) cells (FIGS. 10A and 10B).

Example 7

Inhibition of HuVEC Capillary Tube Formation by Anti-CXCR4 Antibodies

In this example, the ability of the anti-CXCR4 human antibodies to inhibit capillary tube formation by human umbilical vein endothelial cells (HuVEC) was examined MATRIGEL® was diluted 1:1 with RPMI and plated onto the wells of a 96 well plate and allowed to polymerize for 30 minutes at 37° C. HuVEC (from Cambrex, cat. # CC-2519) at 80% confluence were trypsinized and resuspended at $1\times10^6$ cells per ml in RPMI with 0.5% FBS. Antibodies were well mixed with HuVEC at a final concentration of 3 mg/ml and allowed to incubate at room temperature for 30 minutes. An irrelevant antibody of the same isotype or media alone was used as a negative control. As a positive control of inhibition of tube formation, a mouse anti-human αvβ3 (CD51/CD61) antibody (R&D Systems, cat. # MAB3050) was used. HuVEC with or without antibodies were plated onto the MATRIGEL®-coated wells and incubated at 37° C. for 18 hours.

The HuVEC incubated with media alone or with the isotype-matched control antibody formed capillary tubes resulting in the appearance of connected cells across the plate with 3-5 points of connection or branch points per cell. The HuVEC incubated with either the anti-CXCR4 human antibodies or the anti-αvβ3 antibody did not form capillary tubes. The cells appeared isolated and with few or no branch points. The anti-CXCR4 antibodies that were most effective in blocking CXCL12 binding, CXCL12-induced calcium flux and CXCL12-induced migration, namely F7 and F9, were also the most effective in inhibiting capillary tube formation. The anti-CXCR4 antibody E2, which binds to CXCR4 but does not block CXCL12 binding or CXCL12-induced effects, did not inhibit capillary tube formation.

Example 8

Figure 11A:
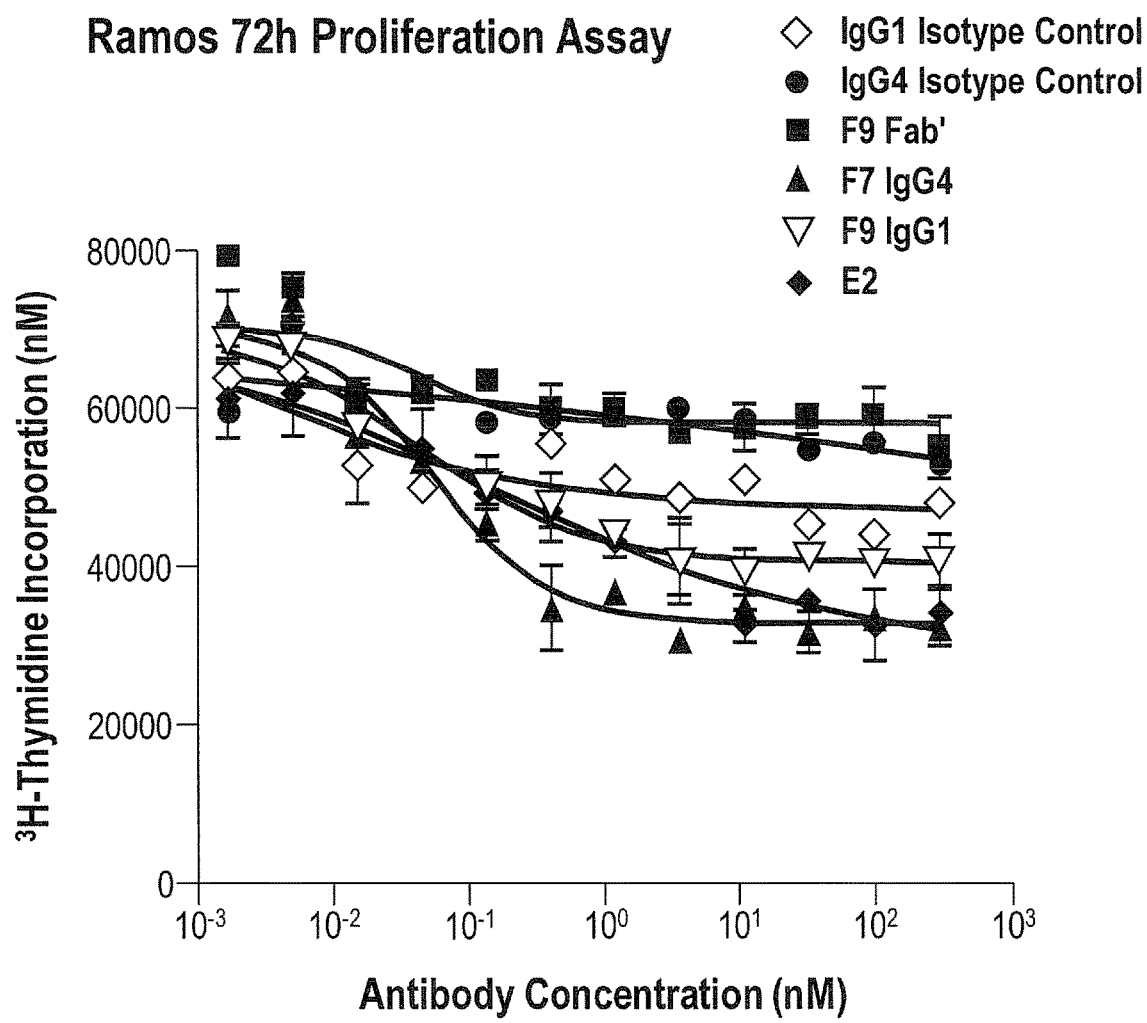
FIG. 11 shows (A) the inhibition of Ramos tumor cell proliferation in vitro by anti-CXCR4 human antibodies F7 (BMS-936564), F9 and E2, and (B) the inhibition of Ramos cell proliferation by MDX-1338 (BMS-936564), compared to no inhibition by anti-CXCL12. In (B), the effects of various peptide CXCR4 antagonists are also shown.

Anti-CXCR4 Antibodies, but not Anti-CXCL12, Inhibit In Vitro Proliferation of CXCR4-Expressing Cells In this example, the ability of the anti-CXCR4 human antibodies to inhibit proliferation of Ramos tumor cells (a human Burkitt's lymphoma cell line) in vitro was examined. In the assay, $1\times10^4$ cells/well were incubated with increasing doses ($10^{-3}$ to 300 nM) of F7 IgG4 antibody, F9 IgG1 antibody, E2 IgG1 antibody, F9 Fab' antibody or isotype controls. The cells were incubated with antibody for 72 hours, with $^3$H-thymidine being added for the final 24 hours of incubation to allow for monitoring of cell proliferation. Following the incubation, incorporation of $^3$H-thymidine by the cells was measured by standard techniques. The results are shown in the graph of FIG. 11A. The results demonstrate that the F7 IgG4, F9 IgG1 and E2 IgG1 antibodies each were able to inhibit Ramos cell proliferation, as indicated by decreased $^3$H-thymidine incorporation when incubated with these antibodies, whereas the F9 Fab' fragment did not inhibit cell proliferation. These results indicate that the anti-CXCR4 human antibodies have a direct anti-proliferative effect on the tumor cells in vitro and thus do not require secondary cross-linking to achieve an anti-proliferative effect.

Figure 11B:
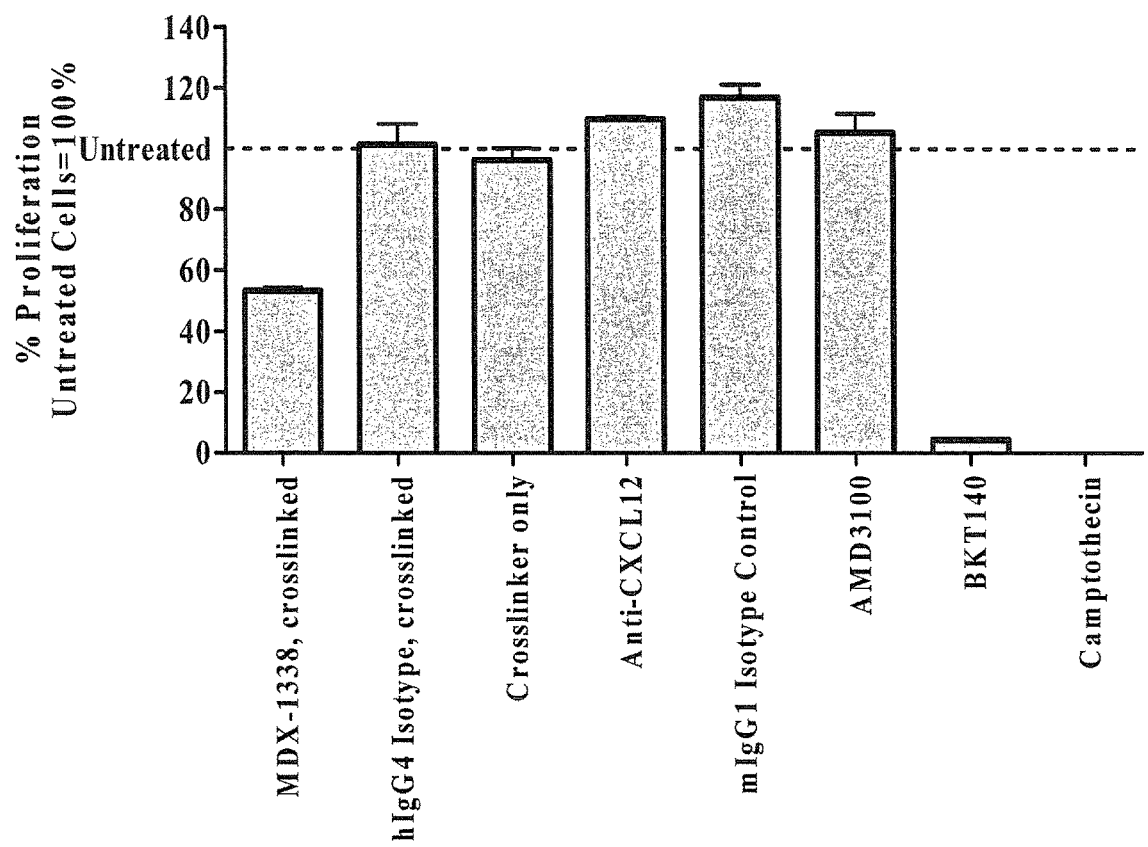

In another experiment, the effects of MDX-1338, anti-CXCL12, and small-molecule CXCR4 antagonists, AMD3100 and BKT140, on proliferation of Ramos cells were compared. Ramos cells were suspended at $1 \times 10^5$ cells/mL in growth media, incubated with the relevant antibodies, including isotype controls, and other test agents and cultured for 72 hours at 37° C. Cell-Titer-Glo (Promega) was added to wells, mixed, and incubated at room temperature for 10 minutes. The plate was read on a GloMax Luminometer (Promega). The results are shown in FIG. 11B. A maximum of about 50% inhibition of Ramos cell proliferation was seen with 40 nM BMS-936564 treatment compared to isotype control, but anti-CXCL12 did not inhibit cell proliferation. In addition, AMD3100, a small molecule CXCR4 antagonist did not inhibit proliferation. A recently described 14-residue peptide antagonist, BKT140, did inhibit proliferation but at much higher concentrations (100 µM). Camptothecin (CPT) completely inhibited cell proliferation at 10 µM.

Example 9

Inhibition of Solid Tumor Cell Proliferation In Vivo by Anti-CXCR4 Antibodies

Figure 12A:
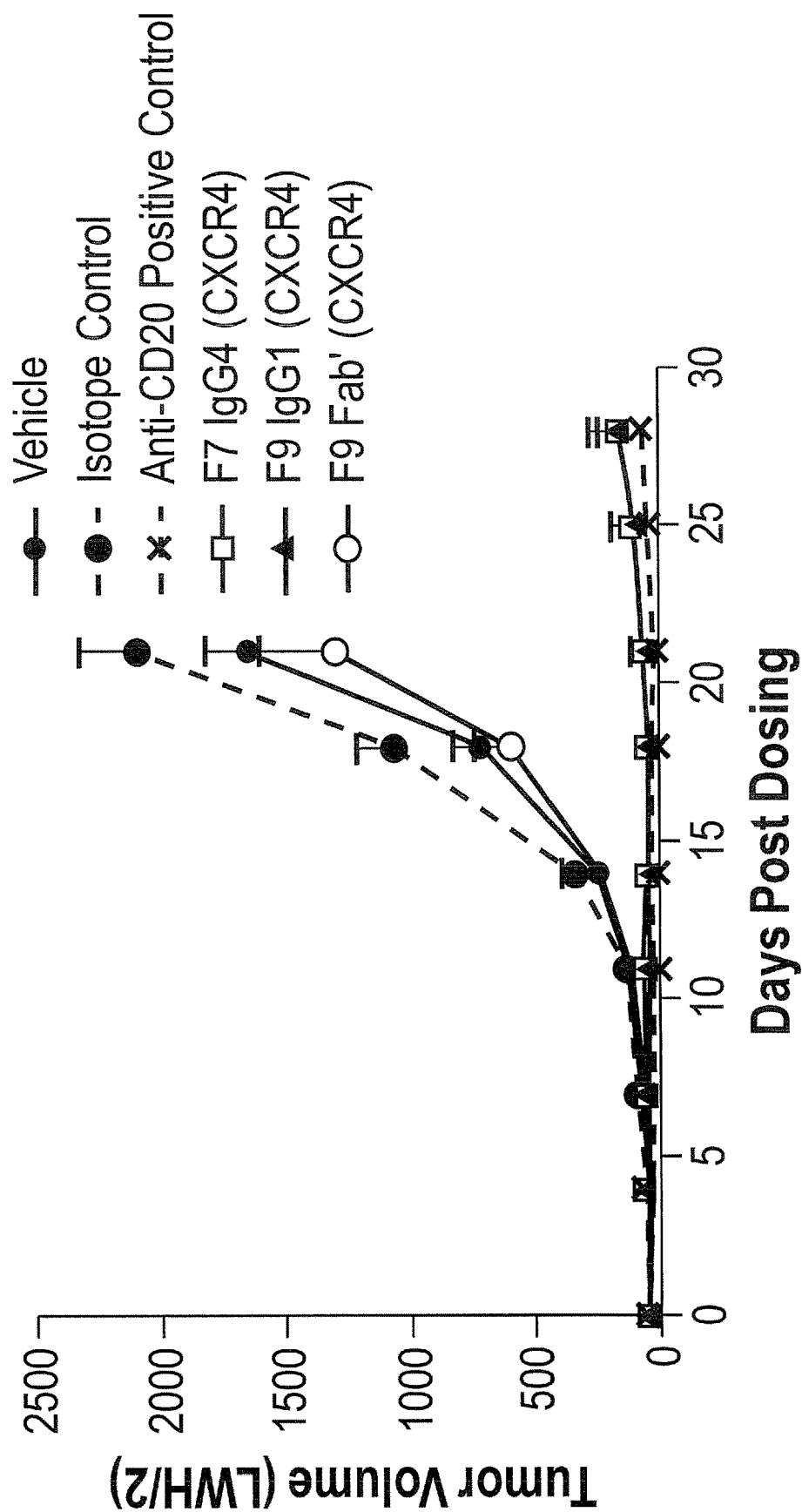
FIG. 12A shows the mean tumor volume growth curve.
Figure 12B:
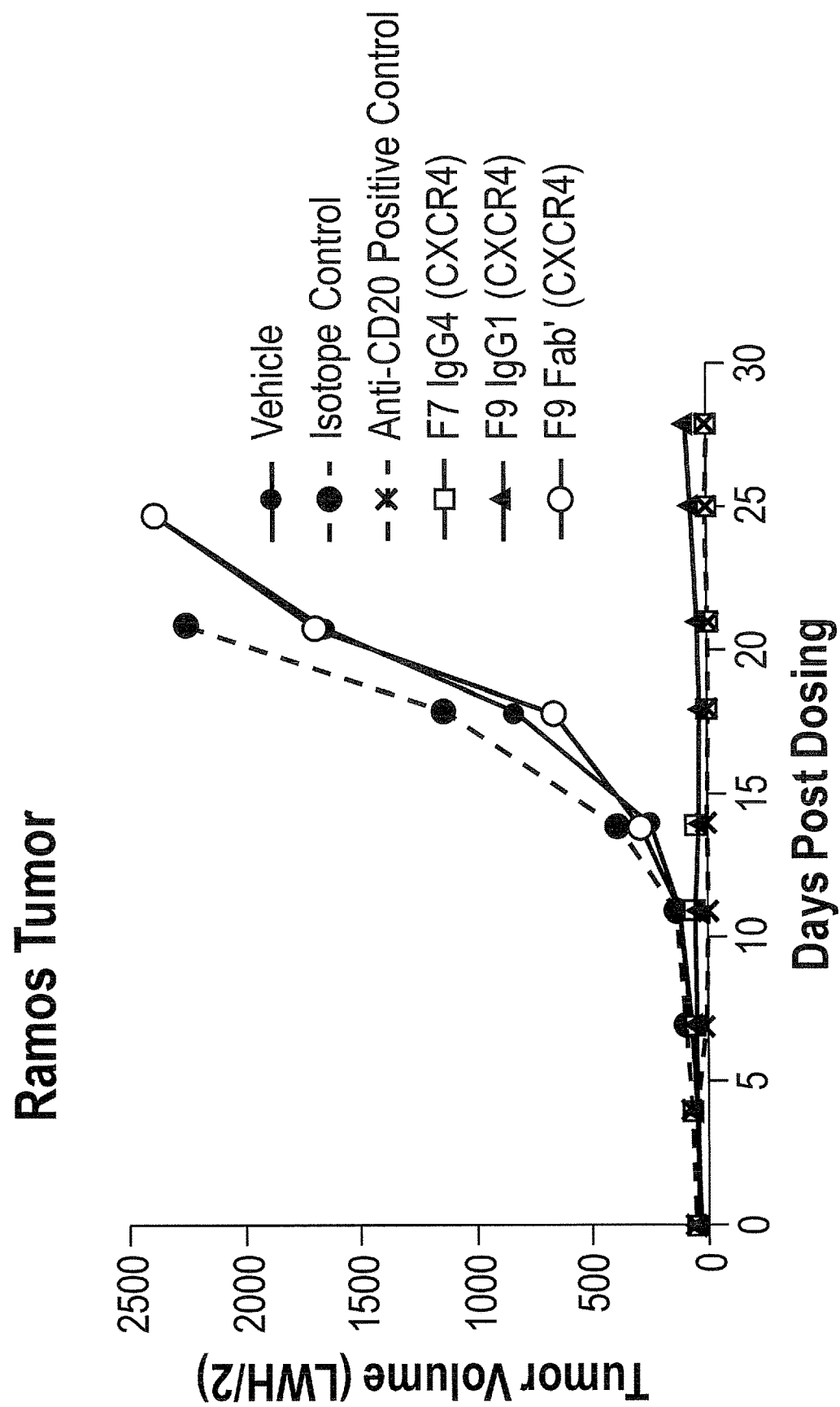
FIG. 12B shows the median tumor volume growth curve.
Figure 12C:
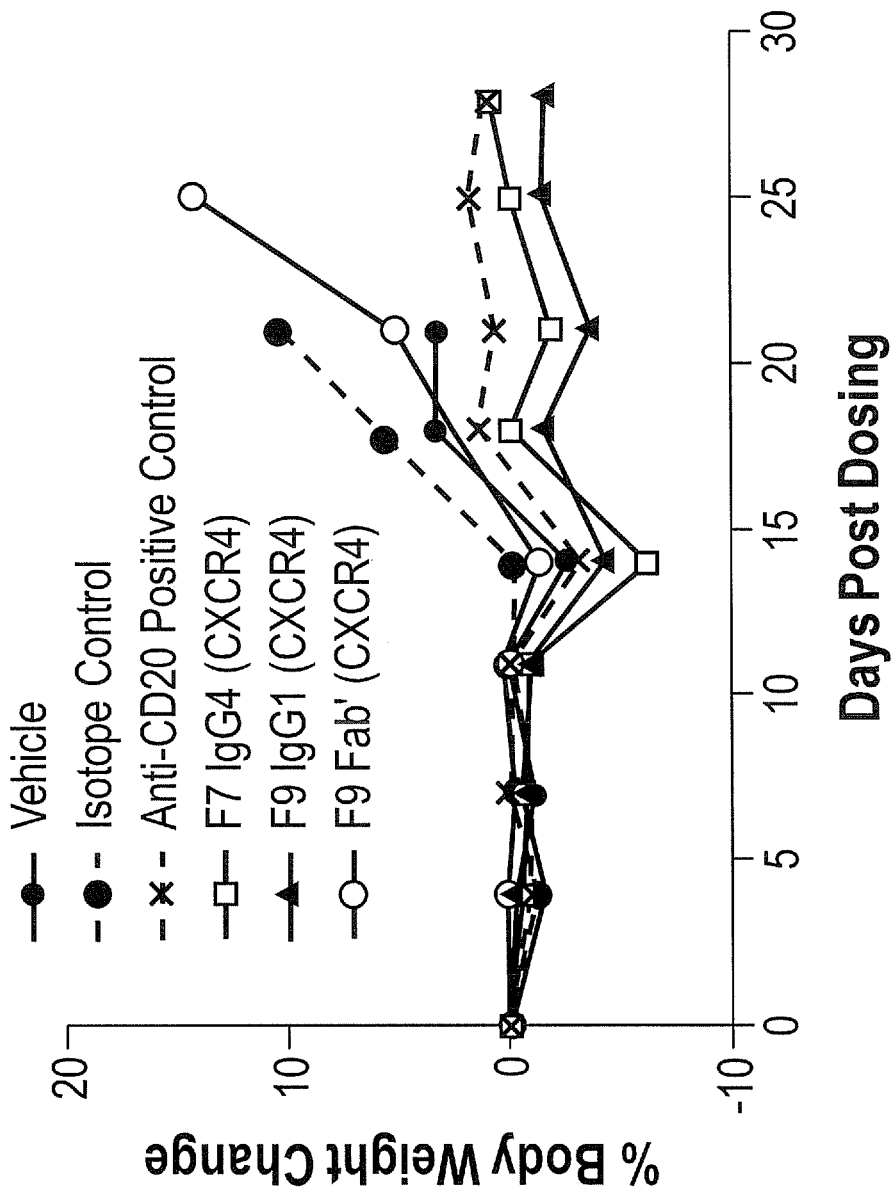
FIG. 12C shows the median % body weight change.

In this example, the ability of the anti-CXCR4 human antibodies to inhibit proliferation of an established solid tumor in vivo was examined using a Ramos subcutaneous tumor cell model. In this assay, $10 \times 10^6$ Ramos cells/mouse were implanted into the flank region of each mouse and allowed to grow to a mean size of 40 mm³, calculated by length×width×height/2 of the tumors. The mice then received an intraperitoneal (IP) injection of a first dose of antibody (designated as day 0 of treatment) and received a second IP dose of antibody on day 7. Mice treated with a Fab' fragment antibody also received IP antibody doses on day 3 and day 10. Groups of mice (n=8) were treated with either (i) vehicle; (ii) isotype control (15 mg/kg); (iii) F7 IgG4 (15 mg/kg); (iv) F9 IgG1 (15 mg/kg); (v) F9 Fab' (10 mg/kg); or (vi) anti-CD20 positive control (15 mg/kg). Tumor volume and mouse body weight were measured at regular intervals (approximately 2-3 times/week) between day 0 and day 30 post dosing. The results of the experiment are presented in FIGS. 12A, 12B and 12C, which show mean tumor volume (FIG. 12A), median tumor volume (FIG. 12B) and median % body weight change (FIG. 12C). The results demonstrated that, like the positive control, the F7 IgG4 and F9 IgG1 antibodies significantly inhibited tumor cell growth as measured by increased tumor volume, whereas the F9 Fab' fragment did not inhibit tumor cell growth as compared to the isotype control. All treatments were well-tolerated as indicated by no significant body weight change. The differences in body weights between treatments were most likely due to the weights of the tumors. The results indicate that the anti-CXCR4 human antibodies are capable of inhibiting growth of an established solid tumor in vivo.

Example 10

Figure 13A:
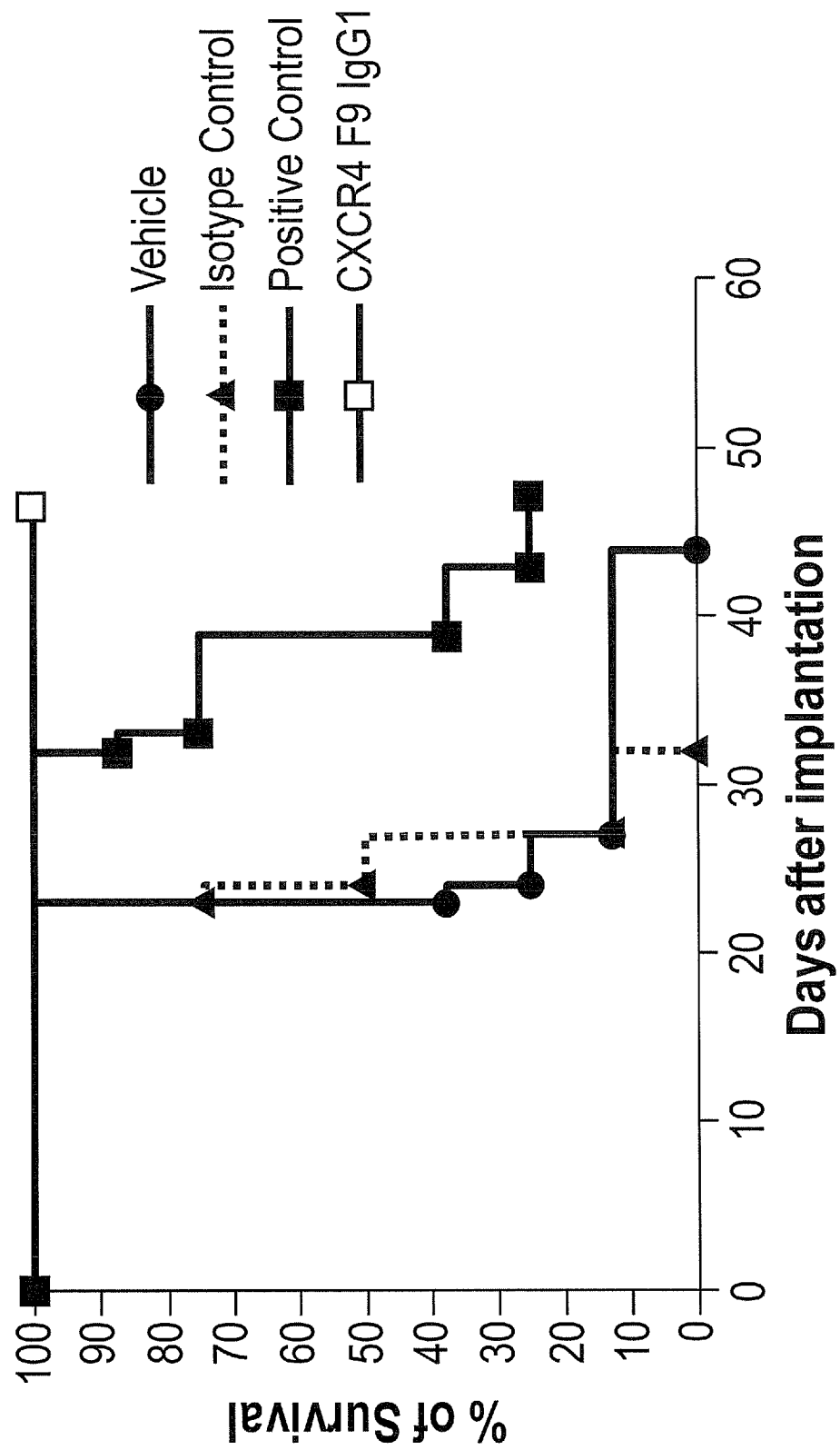
FIG. 13 shows percentage survival of mice treated with the anti-CXCR4 human antibody F9 (A), or the anti-CXCR4 antibody, BMS-936564, and an anti-CXCL12 antibody (B) in a Ramos systemic tumor cell model. BMS-936564 is highly efficacious in this Ramos systemic model, whereas the anti-CXCL12 Ab shows no efficacy.

Increased Survival Time in a Mouse Systemic Tumor Cell Model by Treatment with an Anti-CXCR4 Antibody, but not with an Anti-CXCL12 Antibody In this example, the ability of an anti-CXCR4 human antibody to increase survival time of mice was examined using a Ramos systemic tumor cell model. In this assay, $1 \times 10^6$ Ramos cells/mouse were injected intravenously (IV) into each mouse on Day 0. The mice then received an intraperitoneal (IP) injection of a first dose of antibody on Day 1 (i.e., one day after IV administration of tumor cells) and received four more IP doses of antibody, on days 5, 8, 15 and 22 (mice treated with the positive control antibody were treated only on day 1). Groups of mice (n=8) were treated with either (i) vehicle; (ii) isotype control (15 mg/kg); (iii) F9 IgG1 (15 mg/kg); or (iv) anti-CD19 positive control (15 mg/kg). Dose response studies had previously found 15 mg/kg to be an effective dose of anti-CD19 (data not shown). Percent survival was measured at regular intervals between Day 0 and Day 50 post dosing (hind leg paralysis was used as the endpoint of the experiment). The results of the experiment are presented in FIG. 13A, which shows percent survival over time. The median numbers of days of survival for the mice treated with either vehicle or the isotype control were 23 and 25.5 days, respectively, whereas the median number of days of survival of the mice treated with one dose of the anti-CD19 positive control was 39 days. Significantly, 100% of the mice in the group treated with five doses of the F9 IgG1 antibody survived to the end of the experiment. These results indicate that the anti-CXCR4 human antibody is capable of increasing survival times of mice in a systemic tumor cell model.

Figure 13B:
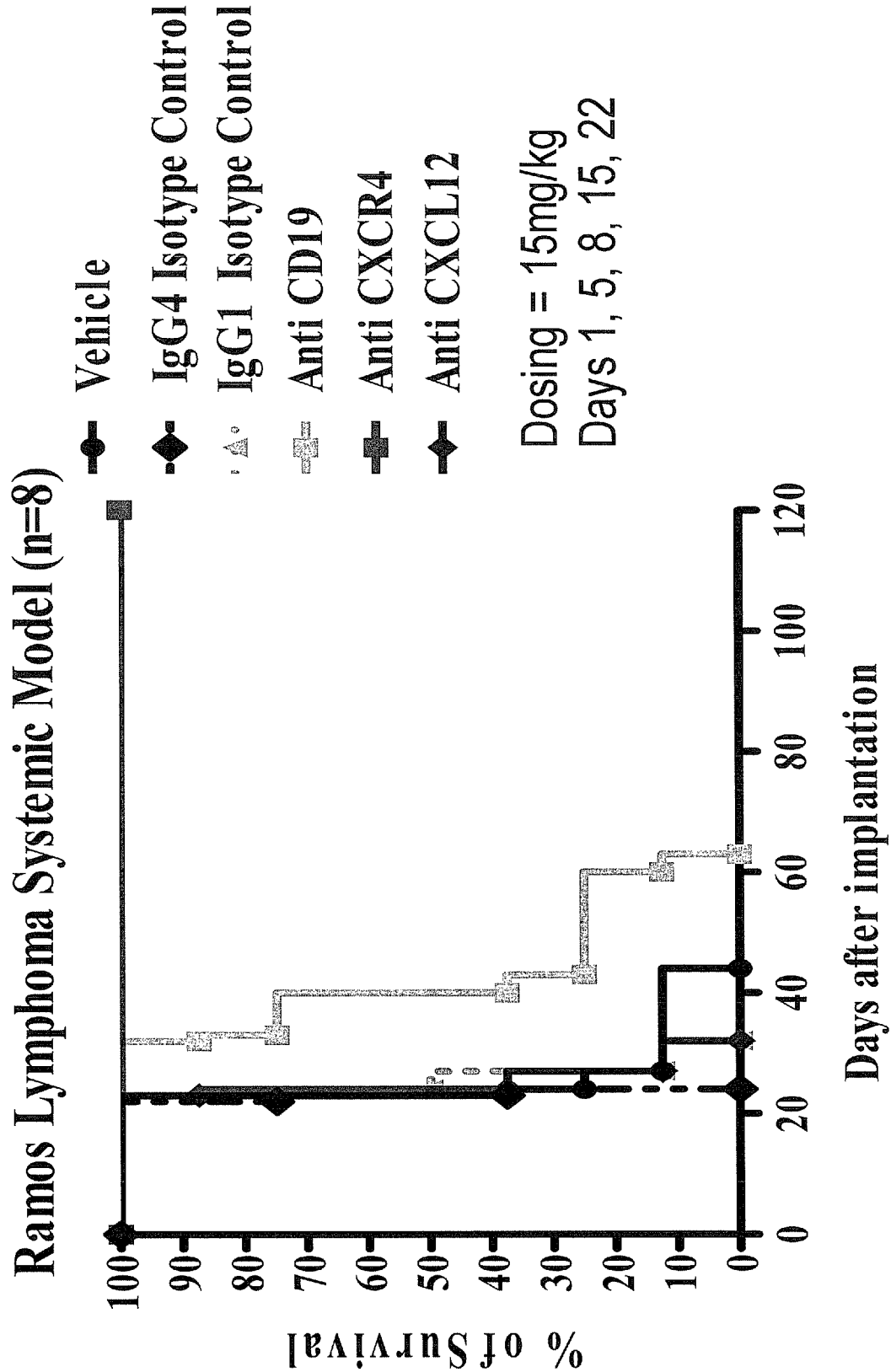

A similar experiment was performed to compare the ability of BMS-936564 and the anti-CXCL12 antibody to increase survival time of mice. SCID mice bearing systemic Ramos tumor xenografts were treated with 15 mg/kg of BMS-936564, the anti-CXCL12 antibody, anti-CD19 positive control, a human IgG4 or IgG1 isotype control, or a vehicle (PBS) control, as described above. BMS-936564 was found to be highly efficacious in prolonging mouse survival in this Ramos systemic model, much more so than the anti-CD19 positive control (see FIG. 13B). The median number of days of survival for the mice treated with the vehicle or the isotype controls were 23-24 days, whereas the median number of days of survival of the mice treated with one dose of the anti-CD19 positive control was 39 days. Significantly, at the end of the experiment 120 days after implantation, 100% of the mice in the group treated with five doses of BMS-936564 survived. In contrast, the anti-CXCL12 antibody surprisingly showed no efficacy, with survival times virtually identical to those of the vehicle and isotype controls. These data indicate that a mechanism(s) other than, or in addition to, blockade of CXCL12-induced effects must be operational in vivo.

Example 11

BMS-936564 Induces Apoptosis of CXCR4-Expressing Cells

The robust in vivo anti-tumor activity of BMS-936564 prompted further studies aimed at understanding the mechanism of action of BMS-936564. Specifically, a set of experiments focused on the ability of the anti-CXCR4 mAb F7 (BMS-936564) to induce apoptosis in different cell lines. In the apoptosis assay, F7 mAb at 10 mg/ml was incubated with either Ramos cells (500,000 cells), Namalwa cells (500,000 cells) or R1610 cells transfected to express CXCR4 (100,000 cells). Untransfected R1610 cells were used as a negative control. Anti-CXCR4 mAb F7 or isotype control antibody was incubated with cells at 37° C. and 250 µl samples were removed at 24, 48 and 72 hours. To assess apoptosis, the cells from various time points were incubated with Annexin V-FITC-FL1 and Propidium Iodide-FL3, followed by flow cytometry. The combined percentage of cells collected in the FL1, FL3 and FL1-FL3 double positive quadrants were considered apoptotic. To remove background, the percentages of isotype antibody-induced apoptotic cells were subtracted from the percentage of BMS-936564-induced apoptotic cells.

The results, summarized below in Table 3, demonstrate that the F7 mAb is capable of inducing apoptosis in the Ramos, Namalwa and R1610-CXCR4 cells while F7 had no effect on induction of apoptosis of parental R1610 cells indicating that the response was CXCR4-specific.

TABLE 3

Induction of Apoptosis by Anti-CXCR4 mAb F7

| Cells | Time (Hours) | % Apoptosis |
| --- | --- | --- |
| R1610 | 72 | <1 |
| R1610-CXCR4 | 24 | 39 |
| R1610-CXCR4 | 48 | 58 |
| R1610-CXCR4 | 72 | 46 |
| Ramos | 24 | 22 |
| Ramos | 48 | 31 |
| Ramos | 72 | 22 |
| Namalwa | 24 | 17 |
| Namalwa | 48 | 24 |
| Namalwa | 72 | 44 |

Total % apoptosis values are corrected for baseline changes induced by isotype control antibodies.

In another experiment, the ability of BMS-936564 to induce apoptosis in a wider variety of cell lines (see Table 4) was examined. The cells ($5 \times 10^5$ cells/mL) were incubated with 10 nM-330 nM of BMS-936564 or isotype control at 37° C. for 24 hours. For a subset of cells (see Table 4), a cross linking antibody (goat anti-human IgG Fc specific polyclonal Ab) was added at six-fold excess. For all cell types, camptothecin (CPT), a cytotoxic quinoline alkaloid which inhibits the DNA enzyme topoisomerase I, was added at 10 µM for 24 hours at 37° C. as a positive control for apoptosis induction. Cells were then resuspended in Annexin V binding buffer (10 mM HEPES at pH 7.4, 140 mM NaCl, 2.5 mM $CaCl_2$) and stained with Annexin V-APC and 7-Aminoactinomycin D (7-AAD) or propidium iodide (PI). Cells were washed, resuspended in Annexin V binding buffer, and analyzed by flow cytometry (FACSArray system, BD Biosciences, San Jose, Calif.) and FlowJo software (Treestar, Inc., San Carlos, Calif.).

Ramos human B lymphoblast Burkitt's lymphoma (Cat. CRL-1596), CCRF-CEM human T lymphoblast acute lymphoblastic leukemia (CCL-119), HL-60 human promyeloblast (CCL-240), Namalwa human B lymphoblast Burkitt's lymphoma (CRL-1432), Raji human B lymphoblast Burkitt's lymphoma (CCL-86), RPMI 8226 human myeloma (CCL-155), MM.1S human B lymphoblast MM (CRL-2974), U226B1 human myeloma (TIB-196), MV-4-11 human biphenotypic B myelomonocytic leukemia (CRL-9591), MJ human T-cell lymphoma (CRL-8294), HH human T-cell lymphoma (CRL-2105), HuT78 human lymphoblast cutaneous lymphoma (TIB-161), NK92 human NK cell non-Hodgkin's lymphoma (CRL-2407) cell lines were purchased from ATCC, Manassas, Va.

Nomo-1 human acute myeloid leukemia (ACC 542), MOLP-8 MM (ACC 569), SU-DHL6 human B cell non-Hodgkin's lymphoma (ACC 572), L540 human Hodgkin's lymphoma (ACC 72), KG-1 human AML (ACC 14), MOLP-8 human MM (ACC 569), OPM-2 human MM (ACC 50), L-363 human plasma cell leukemia (ACC 49) cell lines were purchased from DSMZ, Braunschweig, Germany.

TABLE 4

Induction of Apoptosis on a Panel of Cell Lines by BMS-936564

| Cell Line | Cell Type | CXCR4 Expression | Adjusted Percent Apoptosis | % Tumor Growth Inhibition (Monotherapy) |
| --- | --- | --- | --- | --- |
| Ramos* | Lymphoma | ++++ | 71 | 80 |
| Namalwa* | Lymphoma | ++++ | 30 | 66 |
| Raji* | Lymphoma | ++++ | 15 | 35 |
| DHL6* | Lymphoma | + | 3 | 55/77 |
| L540* | Lymphoma | +++ | 35 | |
| HL60 | AML | ++ | 31 | 60/82 |
| Nomo-1 | AML | ++++ | 34 | 88 |
| KG-1 | AML | ++ | 8 | 23 |
| MOLP-8 | MM | ++ | 19 | 66 |
| RPMI 8226 | MM | ++ | 17 | |
| MM.1S | MM | + | 15 | 49 |
| U226 | MM | + | 22 | |
| JJN3R | MM | ++ | 31 | 97 |
| OPM2 | MM | ++ | 17 | |
| L-363 | MM | + | 16 | |
| MV-4-11 | MM | ++ | 1 | |
| MJ | TCL | ++ | 9 | |
| HH | TCL | +++ | 9 | |
| HuT78 | TCL | + | 22 | |
| CCRF-CEM* | ALL | +++ | 45 | 72 |
| NKL | NK | +++ | 36 | |
| KHYG-1 | NK | + | 10 | |
| NK-92 | NK | ++ | 48 | |
| Human Primary* | B (CD19+) | ++ | 17 | |
| Human Primary* | T (CD3+) | + | 6 | |
| Human Primary* | Monocytes (CD14+) | ++ | 24 | |

*Without cross-linker

| CXCR4 Expression Key | |
| --- | --- |
| MFI with 10 nM Ab | Score (+) |
| 400-2000 | + |
| 2000-10,000 | ++ |
| 10,000-50,000 | +++ |
| 50,000-250,000 | ++++ |

R1610 hamster fibroblasts (CRL-1657) purchased from ATCC were transfected with human CXCR4 and kept under selection using G418 at 500 µg/mL. JJN-3 cells (ACC 541) purchased from DSMZ were selected at BMS for resistance to bortezomib. NKL human NK cell large granulocyte leukemia cell line licensed from Dana-Farber Cancer Institute; KHYG-1 human NK cell leukemia cell line (JCRB0156) was purchased from the Health Science Research Resources Bank, Japan Health Sciences Foundation.

Figure 14A:
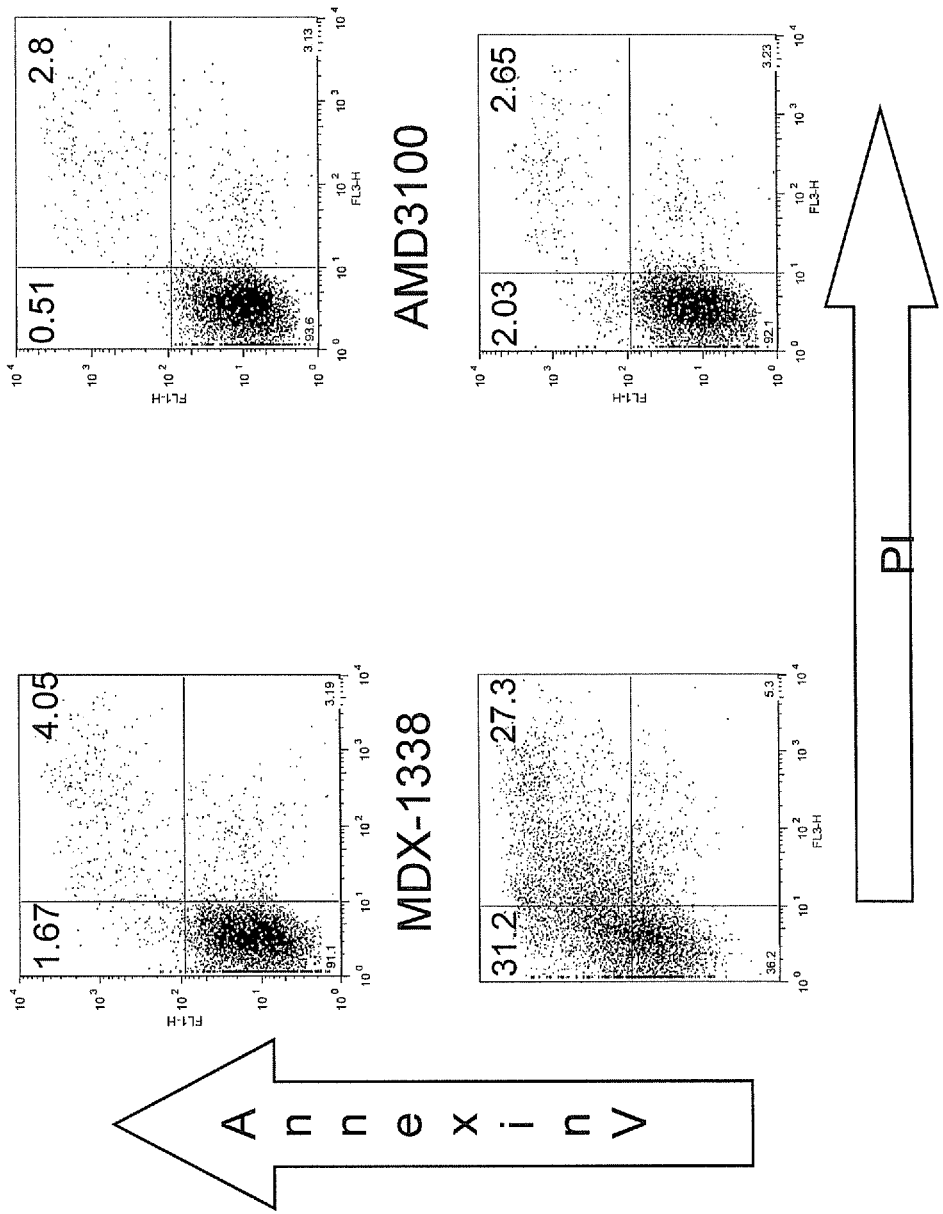
FIG. 14 shows the results of an apoptosis assay carried by incubating Ramos cells for 24 hours at 37° C. with 10 µg/mL MDX-1338 (BMS-936564) or isotype control. Cells were stained with Annexin V-FITC and propidium iodide (A). The percent of cells positive for Annexin V only or both Annexin V and PI double positive was determined (B).
Figure 14B:
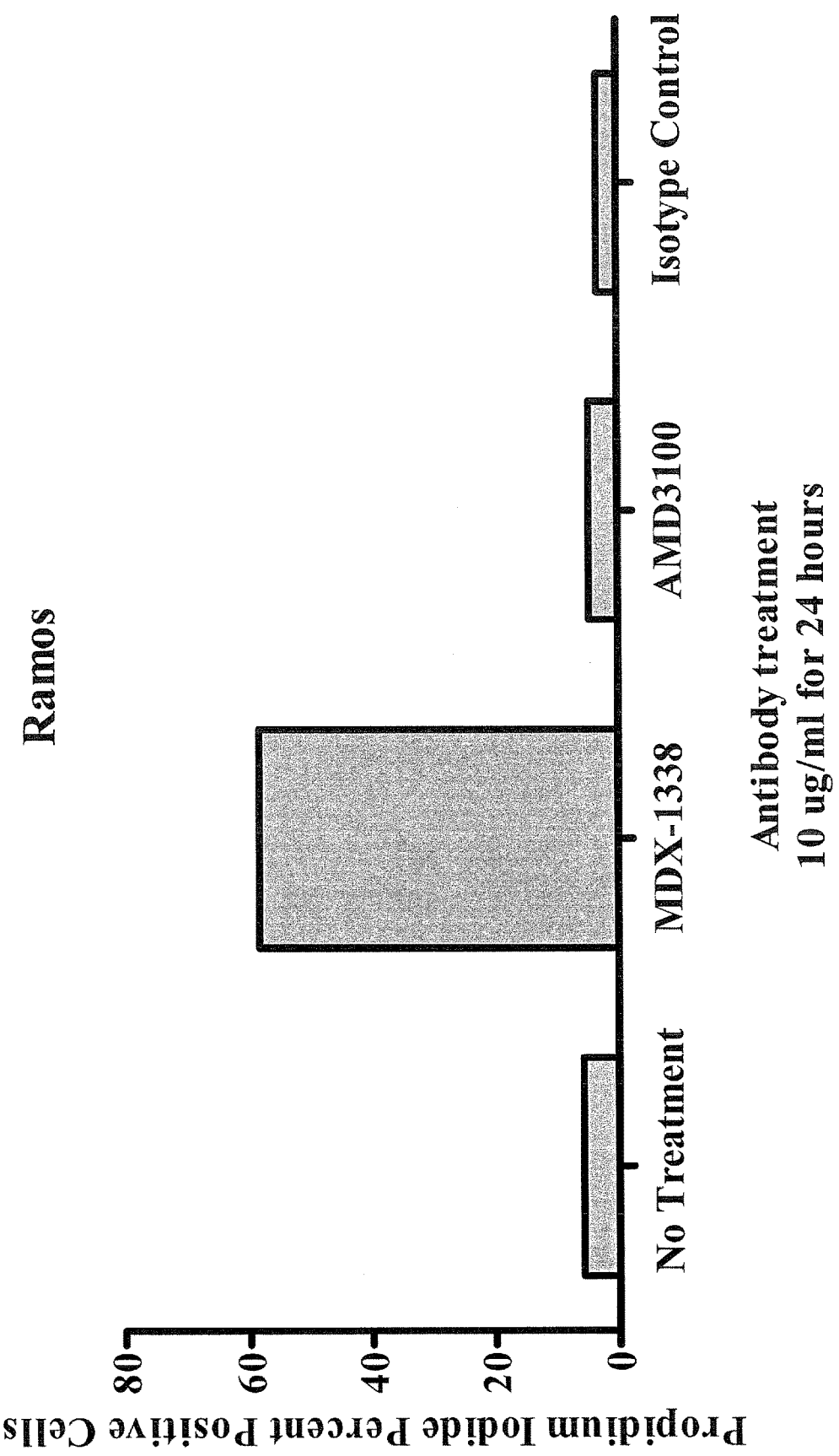

The ability of BMS-936564 to induce apoptosis of $CXCR4^+$ cells was compared with the apoptotic ability of the small molecule CXCR4-antagonist, AMD3100. Apoptosis was investigated by incubating Ramos cells with 10 µg/mL BMS-936564 or isotype control antibody for 24 hours at 37° C. For comparison, Ramos cells were incubated with 6 µM AMD3100, corresponding to the concentration which inhibited CXCL12-induced calcium flux and migration. Cells were stained with Annexin V-FITC and propidium iodide (PI). The percent of cells positive for Annexin V only or both Annexin V and PI double positive was determined BMS-936564 induced an increase in Annexin V (31.2%) and in Annexin V/PI double positive staining (27.3%) compared with cells that were either untreated (1.7% and 4.1%), incubated with isotype control antibody (0.5% and 2.8%), or treated with AMD3100 (2.0% and 2.7%) (FIGS. 14A and 14B).

Figure 15A:
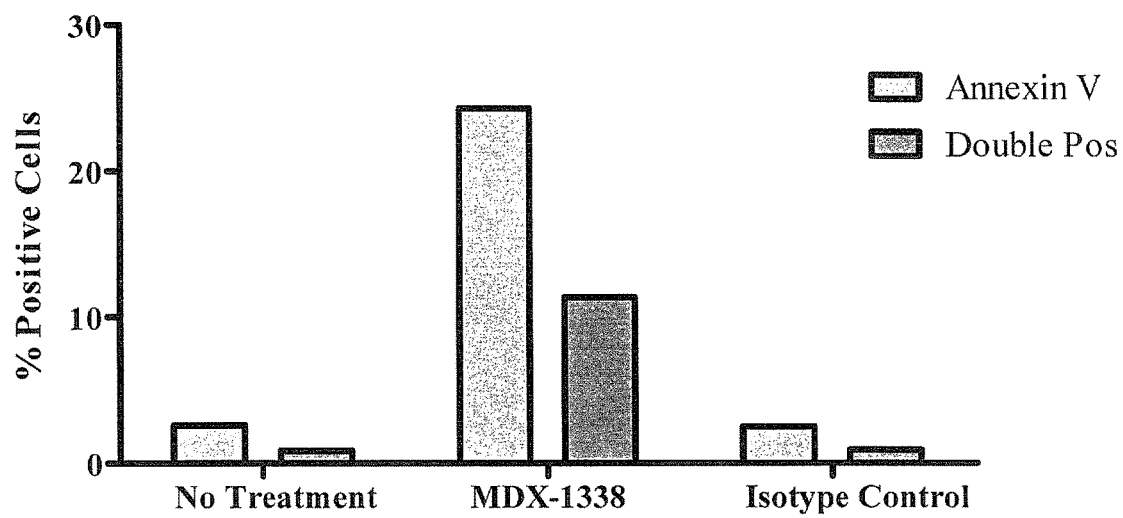
FIG. 15 shows that induction of apoptosis by MDX-1338 (BMS-936564) is CXCR4-specific. MDX-1338 or isotype control were added to CXCR4-transfected cells (A) or R1610 parental cells (B) and stained with Annexin V-FITC and PI. The percentages of cells that were positive for Annexin V only or doubly positive for both Annexin V and PI double positive are illustrated.
Figure 15B:
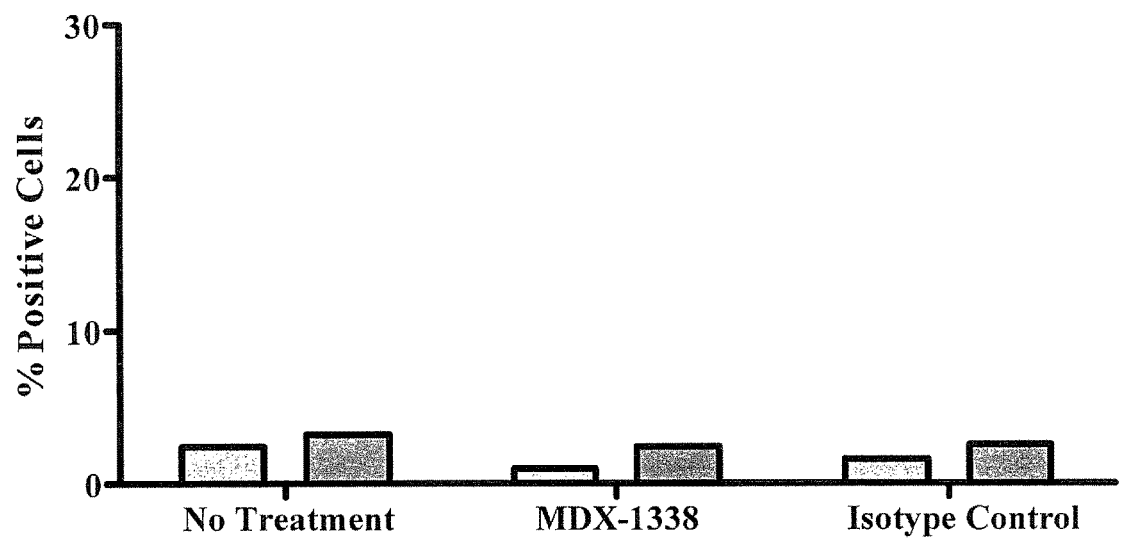

To verify the specificity of the apoptotic response to BMS-936564, parental R1610 cells which do not bind BMS-936564 (data not shown) and R1610 transfected with human CXCR4 that do bind to BMS-936564 (FIG. 4) were used to measure apoptosis. MDX-1338 (BMS-936564) or isotype control were added to R1610 cells and CXCR4-transfected cells for 24 hours at 37° C. then stained with Annexin V-FITC and propidium iodide (PI). The percent of cells that are positive for Annexin V only or both Annexin V and PI double positive was determined. The transfected cells R1610-hCXCR4 exhibited an increased level of Annexin V staining and Annexin V/PI staining in response to incubation with BMS-936564 (24.3% and 11.4%), while an isotype control antibody (2.5% and 0.9%) or when untreated (2.6% and 0.9%) had minimal effects (FIG. 15A). The parental R1610 cells did not exhibit apoptosis following BMS-936564 treatment (FIG. 15B) suggesting specificity for hCXCR4. Subsequent to these findings BMS-936564 was shown to induce apoptosis on several CXCR4$^+$ cell lines as well as normal PBMC (Table 4).

A summary of data on the apoptosis of different CXCR4$^+$ cell lines induced by BMS-936564 versus an isotype control is provided in Table 5.

TABLE 5

In vitro BMS-936558-induced Apoptosis in Multiple Myeloma Cell Lines

| Cell Line | CXCR4 Expression | Antibody Treatment | Annexin V % Positive | Annexin V + 7AAD % Positive |
|---|---|---|---|---|
| MOLP-8 | ++ | Isotype | 16.4 | 11.9 |
|  |  | BMS-936564 | 32.7 | 14.2 |
| RPMI-8226 | ++ | Isotype | 27.1 | 16.9 |
|  |  | BMS-936564 | 36.3 | 24.6 |
| MM.1S | + | Isotype | 20.5 | 8.4 |
|  |  | BMS-936564 | 34.1 | 9.8 |
| JJN-3R | ++ | Isotype | 15.0 | 4.8 |
|  |  | BMS-936564 | 46.8 | 25.1 |
| OPM-2 | ++ | Isotype | 14.4 | 2.8 |
|  |  | BMS-936564 | 31.1 | 3.7 |

The data summarized in Tables 4 and 5 indicate that BMS 936564 induces apoptosis, and thus can be an effective therapeutic, in practically every tumor cell that expresses CXCR4.

Example 12

Additional Studies Showing Inhibition of Tumor Cell Proliferation In Vivo by Anti-CXCR4 Antibodies In this Example, the ability of anti-CXCR4 human antibodies to inhibit proliferation or induce apoptosis of established solid tumors in vivo was examined using additional tumor cell models similar to the Ramos model described above in Example 9. A variety of tumor cell lines were examined Representative experiments and results are as follows.

In one experiment, 7.5×10$^6$ MDA-MB231 human breast cancer cells/mouse were implanted into the flank region of each mouse and allowed to grow to a mean size of 100 mm$^3$, calculated by length×width×height/2 of the tumors, which was day 7 post-implantation. The mice were randomized into different treatment groups and received an intraperitoneal (IP) injection of a first dose of antibody on day 7 post-implantation, received a second IP dose of antibody on day 14 post-implantation and then received a third dose on day 46 post-implantation. Groups of mice (n=9) were treated with either (i) vehicle (PBS); (ii) IgG1 isotype control (15 mg/kg); (iii) IgG4 isotype control (15 mg/kg); (iv) F7 IgG1 (15 mg/kg); or (v) F7 IgG4 (15 mg/kg). Tumor volumes were measured at regular intervals and the mean and median tumor volume determined for each treatment group at each interval. The results of this experiment are summarized below in Table 6, which shows mean tumor volume (in mm$^3$) and % tumor growth inhibition (TGI) at day 52, and median tumor volume (in mm$^3$) and % TGI at day 59 post-implantation. Additionally, one of the mice in the F7 IgG4 treatment group was tumor free at day 59. The results demonstrate that the F7 mAb is capable of inhibiting growth of MDA-MB231 breast cancer cells in vivo.

In a second experiment, 5×10$^6$ DMS79 human small cell lung carcinoma cells/mouse were implanted into the flank region of each mouse and allowed to grow to a mean size of 160 mm$^3$, calculated by length×width×height/2 of the tumors, which was day 7 post-implantation. The mice were randomized into different treatment groups and received intraperitoneal (IP) injections of antibody on a dosing schedule of Q3D×5 (every three days for five times). Groups of mice (n=10) were treated with either (i) vehicle (PBS); (ii) IgG4 isotype control (10 mg/kg); or (iii) F7 IgG4 (10 mg/kg). Tumor volumes were measured at regular intervals and the mean and median tumor volume determined for each treatment group at each interval. The results of this experiment are summarized below in Table 7, which shows mean and median tumor volume (in mm$^3$) and % tumor growth inhibition (TGI) at day 34 post-implantation. The results demonstrate that the F7 mAb is capable of inhibiting growth of DMS79 human small cell lung carcinoma cells in vivo.

TABLE 6

Tumor Growth Inhibition of MDA-MB231 Cells In vivo by mAb F7

|  | Day 52 | | Day 59 | |
|---|---|---|---|---|
| Treatment | Mean | TGI (%) | Median | TGI (%) |
| Vehicle | 154 |  | 187 |  |
| IgG1 Isotype Control | 172 |  | 216 |  |
| IgG4 Isotype Control | 188 |  | 226 |  |
| F7 Anti-CXCR4 IgG1 | 86 | 50 | 130 | 40 |
| F7 Anti-CXCR4 IgG4 | 79 | 58 | 108 | 52 |

TABLE 7

Tumor Growth Inhibition of DMS79 Cells In vivo by mAb F7

|  | Day 34 | | | |
|---|---|---|---|---|
| Treatment | Mean | TGI (%) | Median | TGI (%) |
| Vehicle | 900 |  | 882 |  |
| IgG4 Isotype Control | 992 |  | 903 |  |
| F7 Anti-CXCR4 IgG4 | 620 | 38 | 599 | 34 |

Additional subcutaneous xenograft tumor models were tested for the ability of anti-CXCR4 antibodies to inhibit tumor growth, in experiments similar to those described above and in Example 9. In an experiment using SU-DHL-6 B cell lymphoma cells, the results showed that treatment with the F7 IgG4 mAb at 15 mg/kg resulted in approximately 60% tumor growth inhibition. Similarly, in an experiment using Namalwa Burkitt's lymphoma cells, the results showed that treatment with the F7 IgG4 mAb at 3 mg/kg resulted in approximately 70% tumor growth inhibition. In contrast, no tumor growth inhibition by the F7 mAb was observed in experiments using NIH-H226 lung carcinoma cells or HPAC human pancreatic adenocarcinoma cells. However, staining of these cells by the F7 mAb in flow cytometry experiments showed minimal in vitro expression. Although the tumor cells in vivo were stainable by the mAb by immunohistochemistry, it is unclear at what stage of their tumor growth CXCR4 began to be expressed. This suggests that expression of CXCR4 by these two cell lines was insufficient to allow for tumor growth inhibition or induction of apoptosis in vivo by anti-CXCR4 treatment.

Example 13

Inhibition of Lung Metastases In Vivo by Anti-CXCR4 Antibodies

In this example, the ability of the F7 anti-CXCR4 mAb to inhibit lung metastases was examined using a C57 mouse systemic tumor model. More specifically, $0.4 \times 10^6$ B16-CXCR4 cells (B16 cells transfected to express human CXCR4) were injected intravenously into each of 30 mice of the C57 strain. The mice were randomized into three groups of ten mice each, which were then treated with either (i) vehicle (PBS); (ii) IgG4 isotype control (5 mg/kg); or (iii) F7 IgG4 (5 mg/kg). The antibody or vehicle was injected intraperitoneally 30 minutes after the B16-CXCR4 cells were injected intravenously. Lungs were harvested on day 14 and the number of lung metastasis nodules was quantitated. The results are summarized below in Table 8, which shows the mean and median number of lung metastases in each group. These results show that treatment with the F7 mAb led to a reduction in the mean number of lung metastatic nodules of 56%, whereas reduction was only 15% with the isotype control antibody, demonstrating that the F7 mAb is capable of inhibiting lung metastases in a systemic tumor model.

TABLE 8

Inhibition of Lung Metastases In vivo by mAb F7

| Treatment | Number of Lung Metastases | | % Inhibition of Lung Mets (Mean) |
|---|---|---|---|
| | Mean | Median | |
| Vehicle | 364 | 397 | |
| IgG4 Isotype Control | 309 | 294 | 15% |
| F7 Anti-CXCR4 IgG4 | 157 | 186 | 56% |

Example 14

BMS-936564 Inhibits Tumor Growth in In Vivo Non-Hodgkin's Lymphoma (NHL) Models

The in vivo activity of BMS-936564 and anti-CXCL12 in inhibiting tumor growth was tested in SCID mice bearing tumor xenografts. SCID mice were subcutaneously implanted with 10 million Ramos cells (human B lymphoblast Burkitt's lymphoma cell line) in 0.1 mL phosphate-buffered saline (PBS) and 0.1 mL MATRIGEL®, using a 1-cm$^3$ syringe and a 25-gauge half-inch needle. When a mean and median tumor size of 80 mm$^3$ was reached, the mice were randomized (n=8) according to tumor volume. On Days 0 and 7 each animal was injected intraperitoneally (IP) with ~200 μL of BMS-936564 (15 mg/kg/dose), anti-CXCL12 (15 mg/kg/dose), human IgG4 isotype control (15 mg/kg/dose), rituximab (15 mg/kg/dose) or PBS (vehicle control) at 0.3 mL IP. Dose response studies had previously found 15 mg/kg to be an effective dose of rituximab (data not shown). All antibody doses were well tolerated and no body weight losses were observed. Tumors and body weights were measured twice weekly. Tumor volumes were measured in three dimensions (L×W×H/2) with a Fowler Electronic Digital Caliper (Model 62379-531; Fred V. Fowler Co., Newton, Mass.), and data was electronically recorded using Study Director software from StudyLog Systems, Inc. (South San Francisco, Calif.). Animals were checked daily for postural, grooming, and respiratory changes, as well as lethargy. Mice were euthanized when the tumors reached the 2000 mm$^3$ endpoint or appeared ulcerated.

Figure 16:
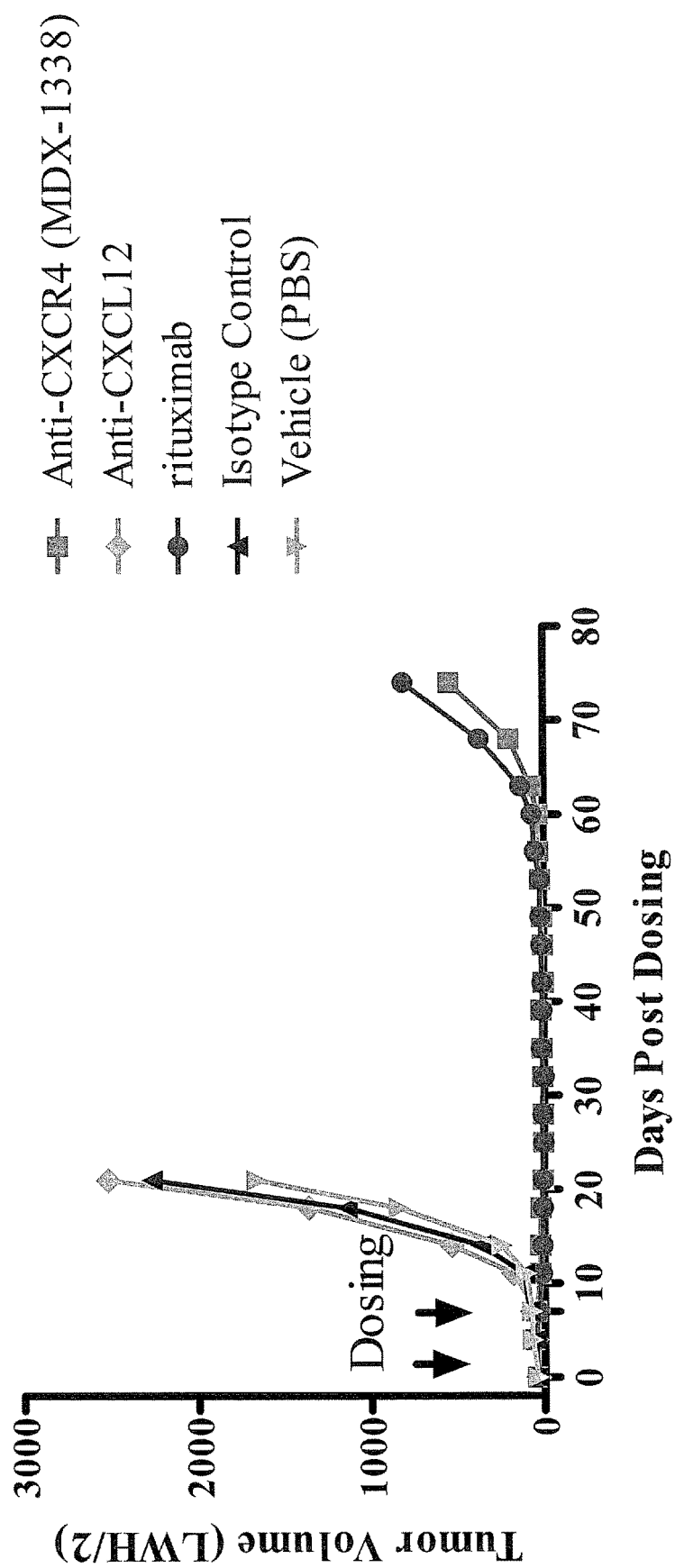
FIG. 16 shows in vivo tumor growth inhibition of a Ramos cell lymphoma xenograft by a blocking CXCR4 antibody, MDX-1338 (BMS-936564), and a rituximab (chimeric anti-CD20 monoclonal antibody) positive control, and the absence of tumor growth inhibition by a blocking anti-CXCL12 antibody.

BMS-936564 and the positive control, rituximab, inhibited tumor growth when compared with vehicle and isotype controls. Treatment with BMS-936564 resulted in a median growth inhibition of 99% on Day 21 and the inhibition was maintained for 60 days (FIG. 16). In contrast, anti-CXCL12 did not inhibit tumor growth and performed similarly to the isotype control antibody.

Example 15

BMS-936564 Inhibits Tumor Growth in In Vivo Acute Myeloid Leukemia (AML) Models

Figure 17A:
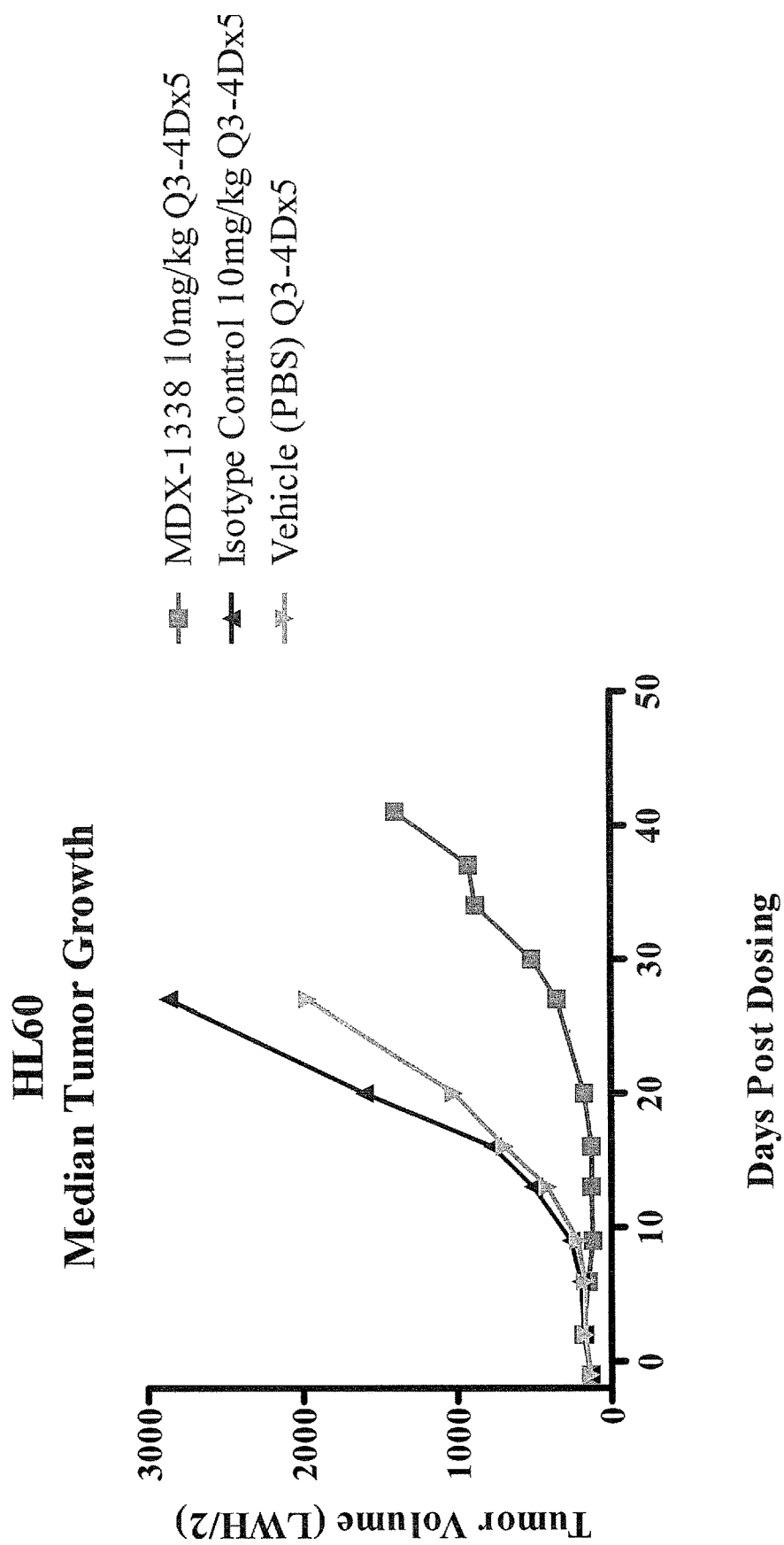
FIG. 17 shows in vivo tumor growth inhibition of a HL60 cell (A) and a Nomo-1 (B) acute myeloid leukemia xenograft by MDX-1338 (BMS-936564). Cytarabine expectedly did not inhibit tumor growth of the cytarabine-resistant Nomo-1 tumor.

To assess the antibody's efficacy in AML, two cytarabine-resistant mouse xenograft models, HL-60 and Nomo-1 were used. CXCR4 expression in each cell line was confirmed by FACS staining (FIG. 4A). SCID mice were subcutaneously implanted with 10 million HL-60 cells as described in Example 14. When the tumor volume reached approximately 136 mm$^3$, the mice were randomized (n=10) and dosed IP on Days 0, 3, 7, 10 and 14 with BMS-936564 (10 mg/kg/dose), human IgG4 isotype control (10 mg/kg/dose), or PBS (vehicle control), and monitored for 41 days. On Day 27, the median tumor growth inhibition was 88% and 83% when compared to isotype and vehicle groups, respectively (FIG. 17A).

In the Nomo-1 model (7.5 million cells implanted subcutaneously as in Example 14). When the tumor volume reached approximately 84 mm$^3$, the mice were randomized (n=9) and dosed with on Days 0, 3, 7, 10 and 14 with BMS-936564 (10 mg/kg/dose), IgG4 isotype control (10 mg/kg/dose), PBS (vehicle control) or cytarabine (20, 60 or 90 mg/kg/dose), and monitored for 57 days. On day 34, the median tumor growth inhibition of BMS-936564-treated mice was significantly delayed by 88% compared to isotype or vehicle control (FIG. 17B). As expected, cytarabine (also known as arabinofuranosyl cytidine or Ara-C) did not inhibit tumor growth (FIG. 17B).

Example 16

BMS-936564 Inhibits Tumor Growth in In Vivo Multiple Myeloma (MM) Models

Figure 18A:
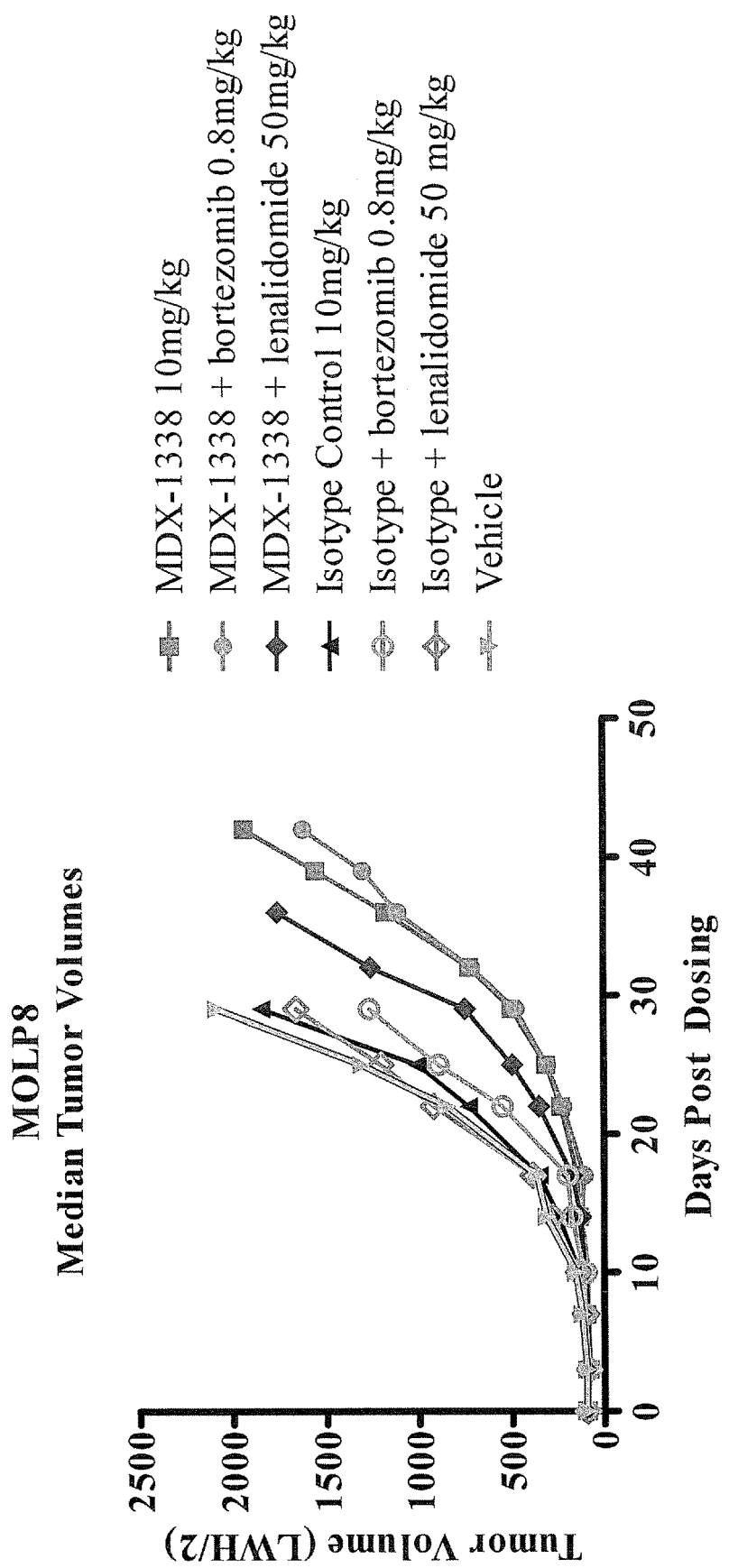
FIG. 18 shows in vivo tumor growth inhibition of a variety of CXCR4+ multiple myeloma cell xenografts by MDX-1338 (BMS-936564). A, tumor growth inhibition of MOLP8 cell xenografts treated with MDX-1338 alone or in combination with lenalidomide or bortezomib; B, tumor growth inhibition of JJN-3R cell xenografts treated with MDX-1338 or lenalidomide or bortezomib; C, tumor growth inhibition of parental JJN-3 cell xenografts treated with MDX-1338 alone or in combination with bortezomib; D, tumor growth inhibition of parental JJN-3 cell xenografts treated with MDX-1338 alone or in combination with lenalidomide; E, tumor growth inhibition of RPMI-8226 cell xenografts by MDX-1338 alone or in combination with lenalidomide (REVLIMID®); F, tumor growth inhibition of RPMI-8226 cell xenografts by MDX-1338 alone or in combination with bortezomib (VELCADE®); G, tumor growth inhibition of MM.1S cell xenografts by MDX-1338 alone or in combination with lenalidomide; H, tumor growth inhibition of OMP-2 cell xenografts by MDX-1338 alone or in combination with bortezomib; I, tumor growth inhibition of OPM-2 cell xenografts by MDX-1338 alone or in combination with lenalidomide.

A variety of CXCR4$^+$ myeloma cells, namely MOLP8, JJN-3R, JJN-3, RPMI-8226, MM.1S and OPM-2, were tested for sensitivity to BMS-936564 in SCID xenograft tumor models. In all the experiments, the mice were injected intraperitoneally on Days 0 and 7 with an IgG4 isotype control and a PBS vehicle control. MOLP-8 cells (2.5 million) were implanted into SCID mice as described in Example 14. When the tumor volume reached approximately 100 mm$^3$, the mice were randomized into groups of 8 mice (n=8) and dosed on Days 0, 3, 7, 10 and 14 with BMS-936564 (10 mg/kg/dose) alone or in combination with 50 mg/kg lenalidomide (REVLIMID®) or in combination with 0.8 mg/kg bortezomib (VELCADE®). BMS-936564 significantly delayed mean tumor growth by 66% and 56% when compared to isotype antibody control on Day 25 (last day when all mice in each cohort remained in the study) (FIG. 18A). MOLP8 tumors were relatively resistant to lenalidomide and bortezomib and the efficacy of BMS-936564 was not improved when combined with either drug (FIG. 18A). At the end of study on day 42, 5 out of 8 mice remained in the BMS-936564 group while no mice remained in the isotype-treated group.

Figure 18B:
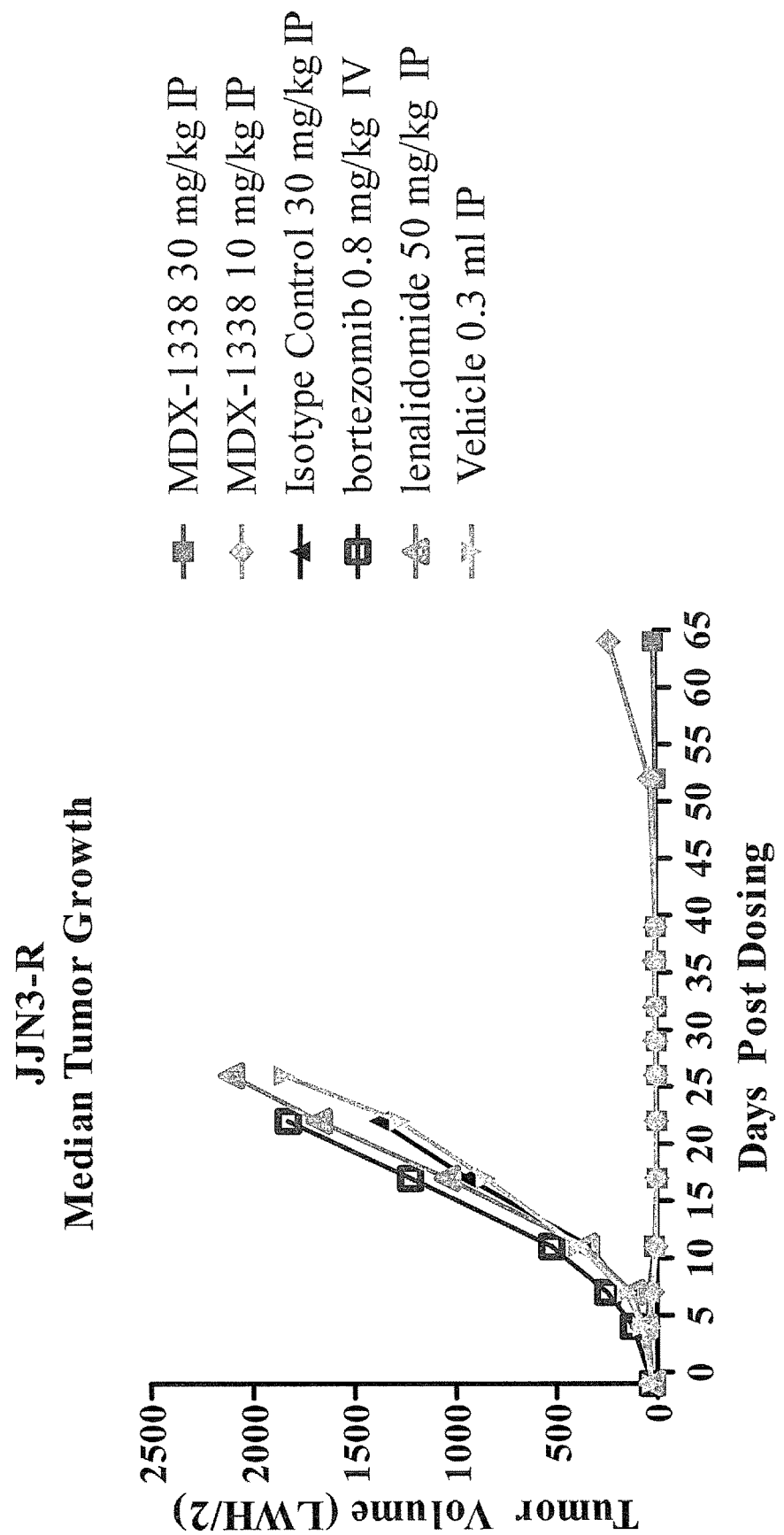

Bortezomib-resistant JJN-3R cells (5 million) were implanted into SCID mice as described. At a tumor volume of approximately 100 mm$^3$, the mice were randomized (n=8), dosed with BMS-936564 (10 or 30 mg/kg/dose IP) or lenalidomide (50 mg/kg/dose IP) or bortezomib (0.8 mg/kg/dose IV) on Days 0, 4, 7, 11 and 14, and monitored for 25 days. Median tumor growth over time is shown in FIG. 18B. Neither lenalidomide nor bortezomib alone inhibited tumor growth while median tumor growth inhibition was 100% for mice treated with BMS-936564 on day 25 compared to mice treated with the isotype control. At the end of study, 4 out of 7 mice were tumor-free in the BMS-936564 30-mg/kg group.

Figure 18C:
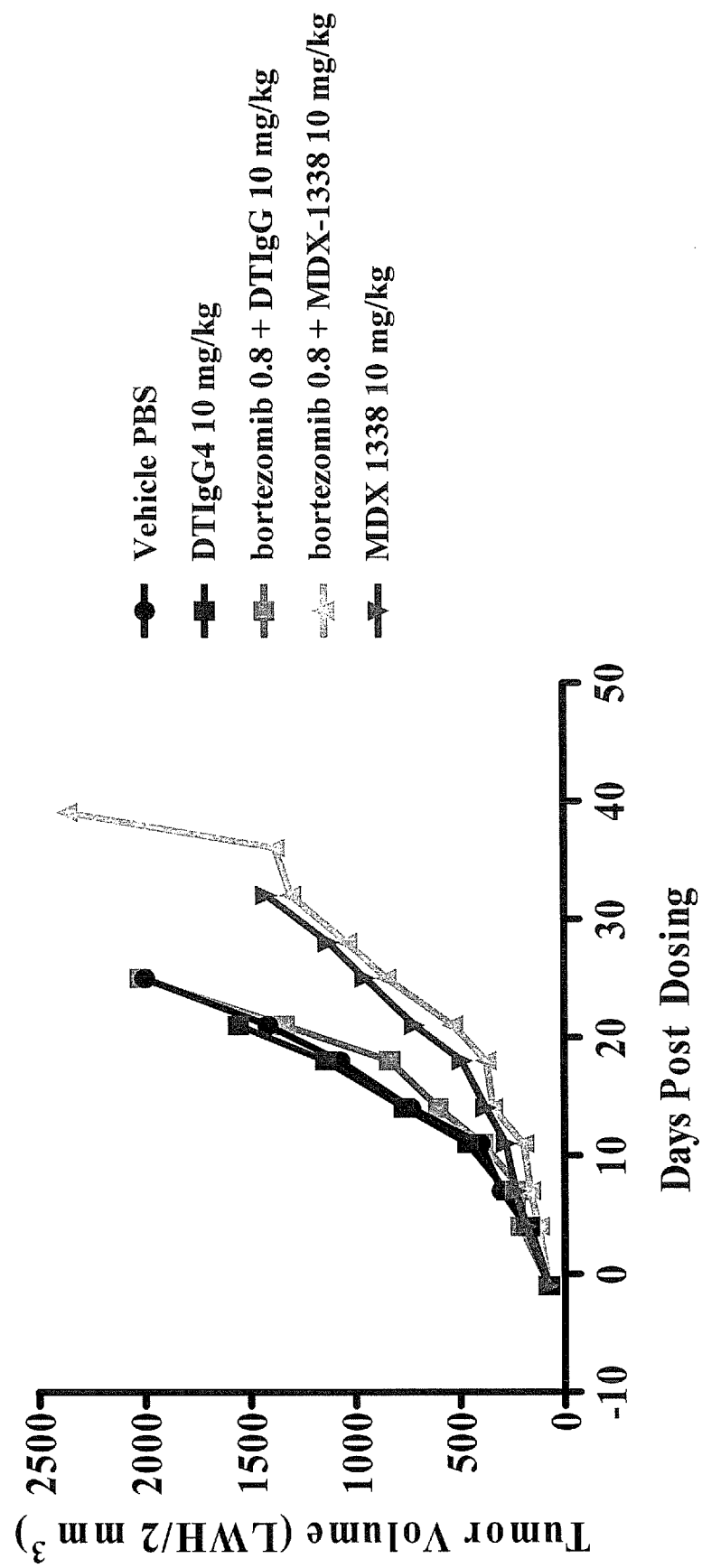
Figure 18D:
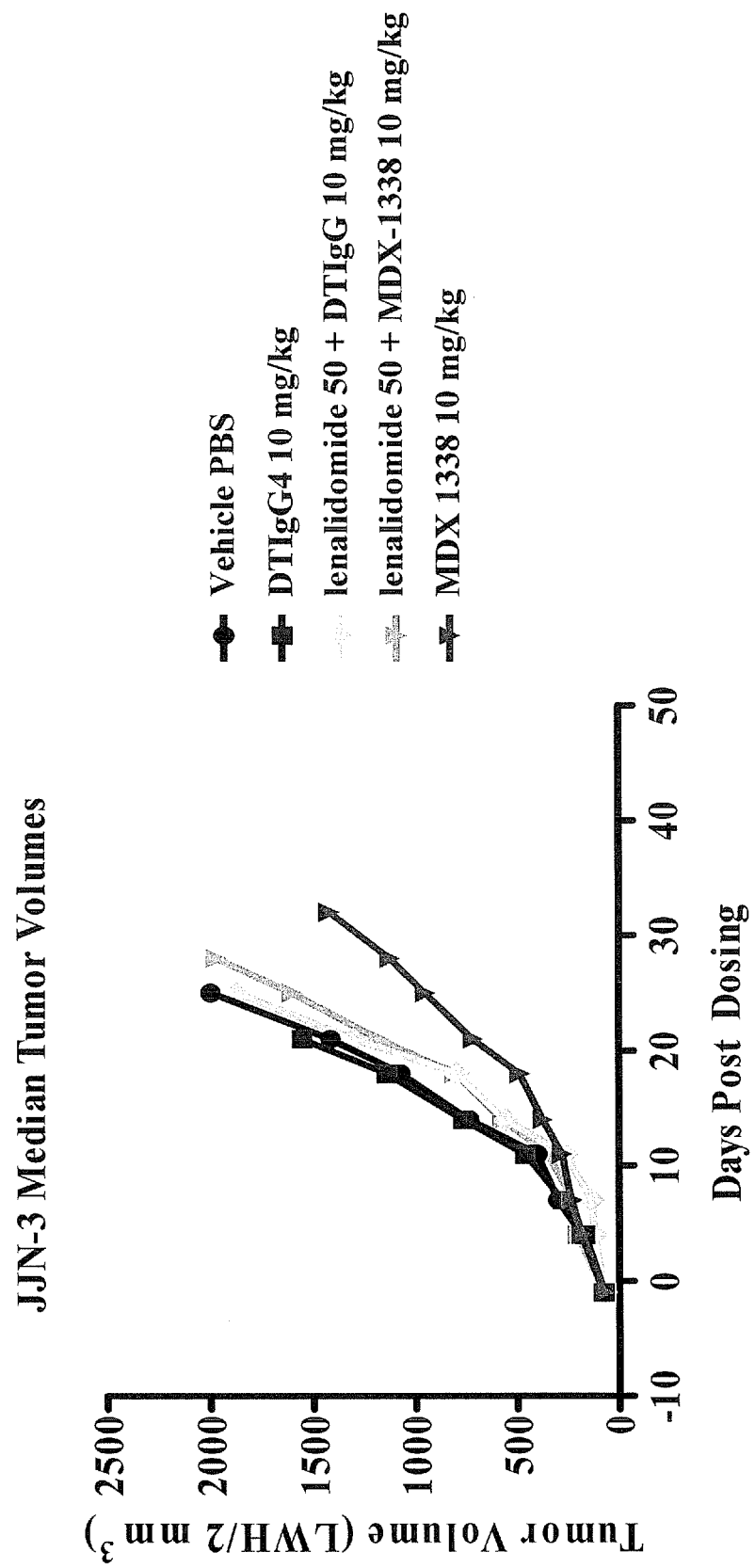

Using the parental JJN-3 cells, both bortezomib and lenalidomide, exhibited virtually no tumor-inhibiting efficacy. 5 million JJN-3 cells/mouse were implanted into SCID mice and the mice were randomized into groups of 8 when the tumor volume reached approximately 77 mm$^3$. The mice were dosed with MDX-1338 (10 mg/kg/dose IP) alone or in combination with bortezomib (0.8 mg/kg/dose IV) or lenalidomide (50 mg/kg/dose IP) on Days 0, 3, 7, 10, and 14. MDX-1338 inhibited tumor growth by 52% on Day 25 compared to mice treated with the vehicle control (FIG. 18C). Bortezomib exhibited marginal efficacy in inhibiting tumor growth in this JJN-3 cell model but in combination with MDX-1338 marginally increased the level of MDX-1338-induced inhibition to 58% on Day 25 compared to vehicle control (FIG. 18C). Lenalidomide was ineffective in inhibiting tumor growth, and the combination of lenalidomide and MDX-1338 was similarly ineffective, exhibiting less inhibition than MDX-1338 alone (FIG. 18D).

Figure 18E:
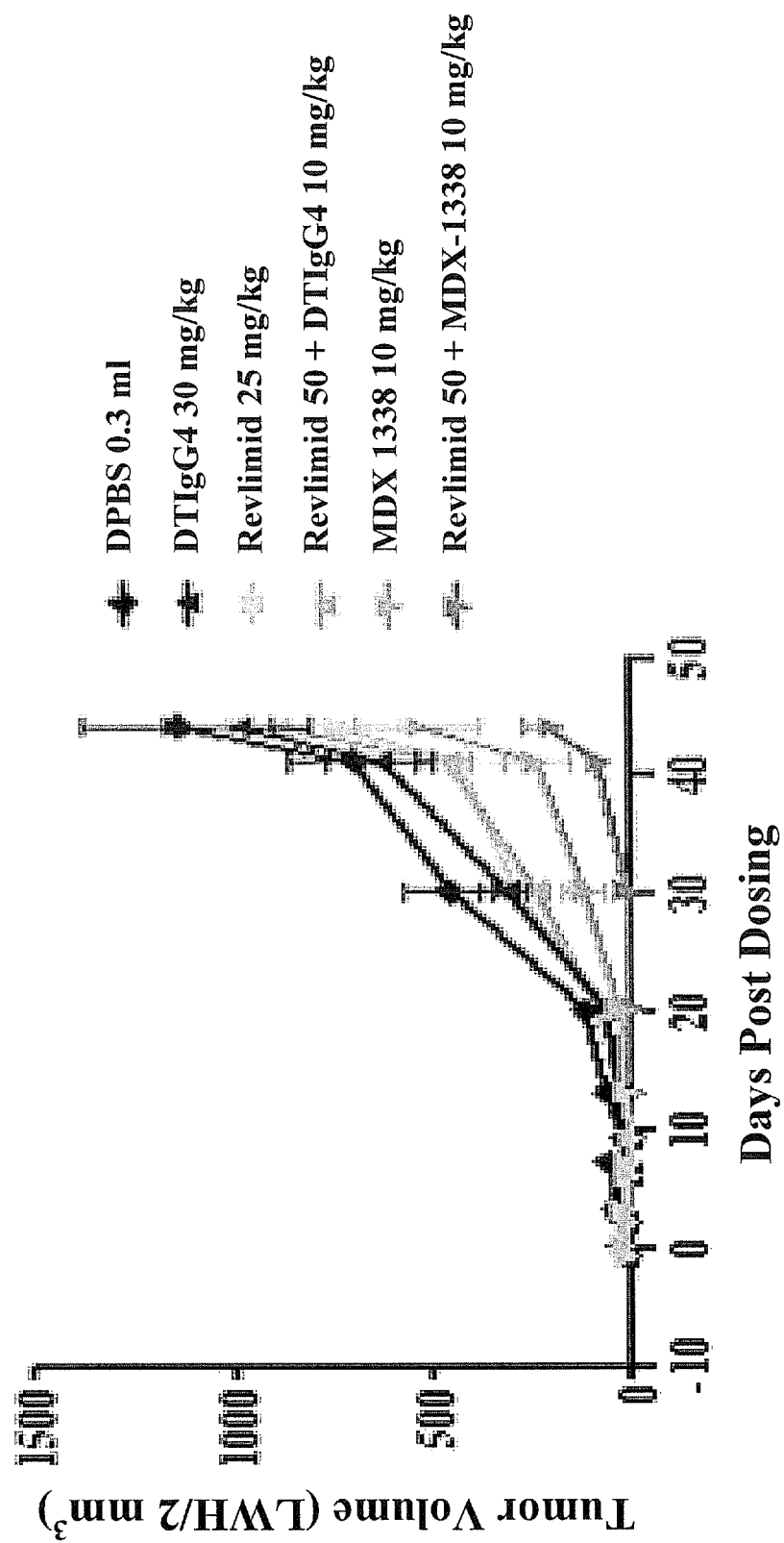
Figure 18F:
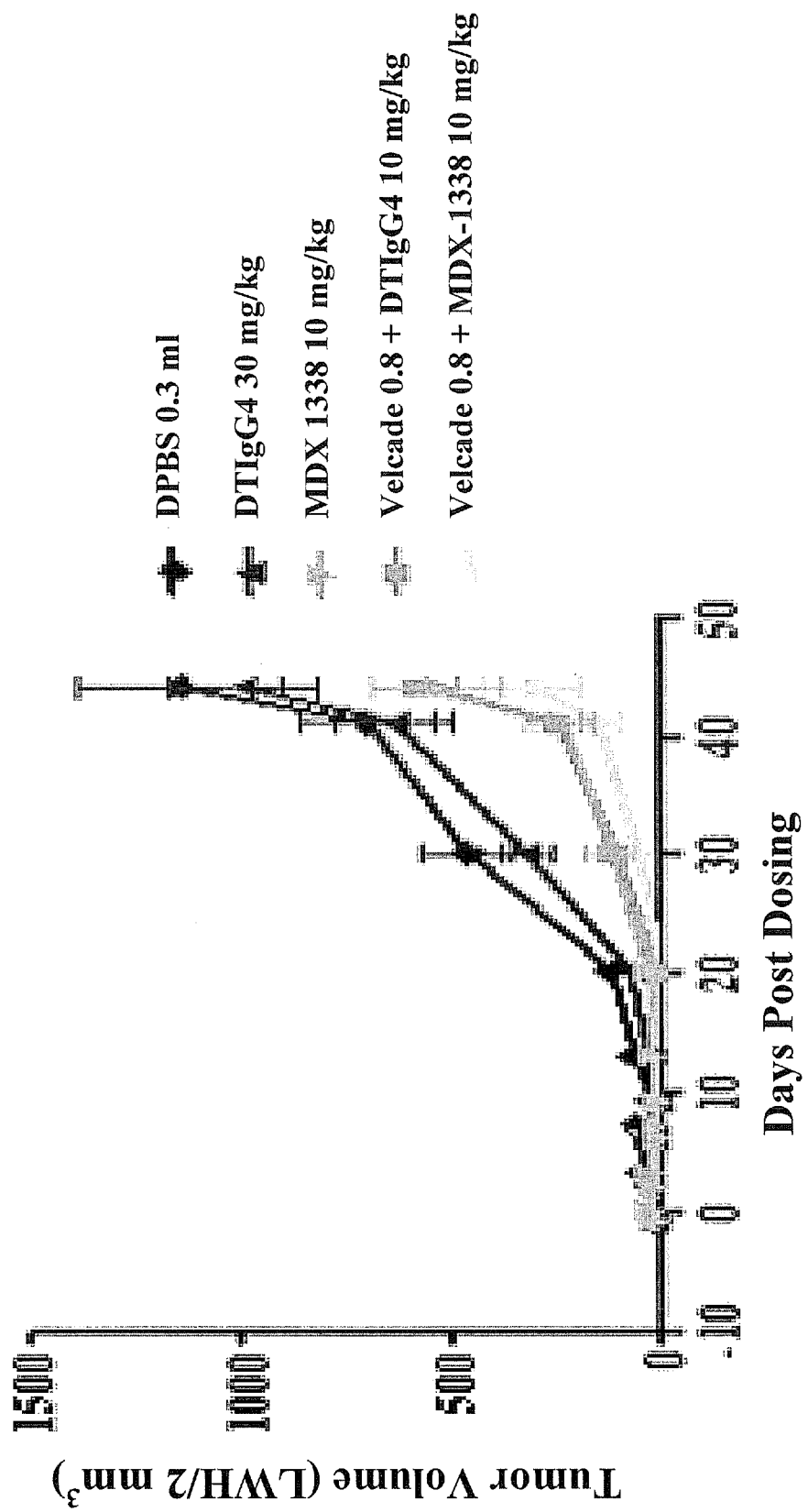

RPMI-8226 cells (10 million) were implanted into SCID mice as described in Example 14. The mice were randomized (n=8) when the tumor volume reached approximately 20 mm$^3$, dosed on Days 0, 3, 7, 10 and 14 with MDX-1338 (10 mg/kg/dose) alone or in combination with 50 mg/kg lenalidomide or in combination with 0.8 mg/kg bortezomib. MDX-1338 significantly delayed mean tumor growth by 53% when compared to the vehicle control on Day 44 (FIG. 18E). Lenalidomide alone exhibited marginal efficacy in this RPMI-8226 model, but it enhanced the efficacy of MDX-1338-tumor growth inhibition seen with 50 mg/kg lenalidomide in combination with 10 mg/kg MDX-1338 was 79% at Day 44 compared to isotype control (FIG. 18E). Bortezomib exhibited good efficacy in inhibiting mean tumor growth by 70% at Day 44 compared to isotype control (FIG. 18F), and slightly enhanced the efficacy of MDX-1338 which increased from 61% mean tumor growth inhibition to 82% at Day 44 compared to isotype control (FIG. 18F).

Figure 18G:
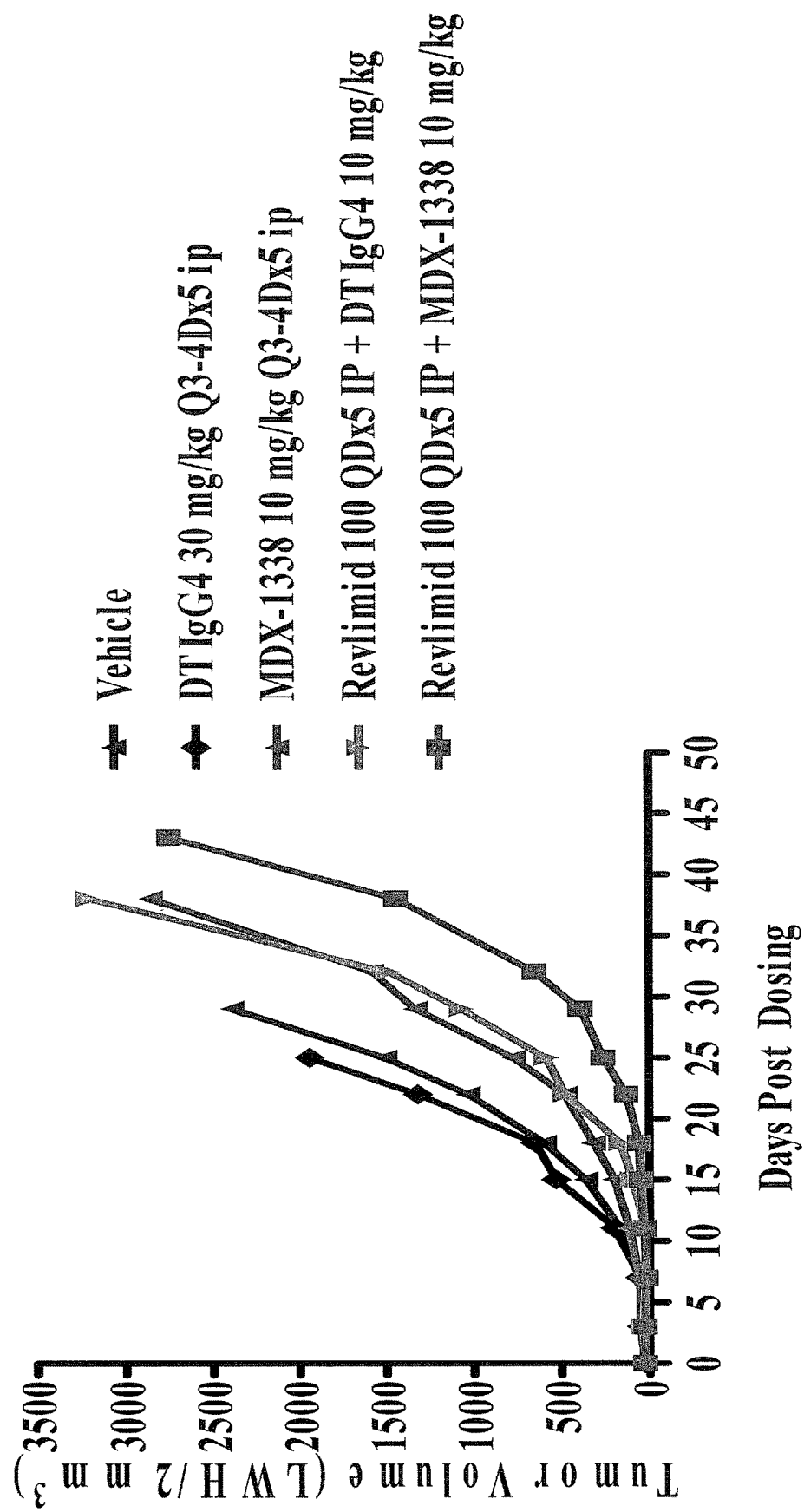

MM.1S cells (10 million) were implanted into SCID mice and randomized (n=8) when the tumor volume reached approximately 30 mm$^3$, dosed on Days 0, 4, 7, 11 and 14 with MDX-1338 (10 mg/kg/dose) alone or in combination with 100 mg/kg lenalidomide. MDX-1338 significantly delayed mean tumor growth by 60% when compared to isotype control on Day 25 (FIG. 21). Lenalidomide alone was even more efficacious, delaying mean tumor growth by 70% on Day 25, and the combination of MDX-1338 and lenalidomide inhibited mean tumor growth 86% at Day 25 (FIG. 18G).

TABLE 9

CXCR4 expression, Apoptosis and Tumor Growth Inhibition in Multiple Myeloma Cell Lines

| Cell Line | CXCR4 Expression | Apoptosis by MDX-1338 Alone | Apoptosis in Presence of Cross-Linking Ab | Tumor Growth Inhibition |
|---|---|---|---|---|
| MOLP8 | ++ | − | + | MDX-1338 = 56% REVLIMID ® alone = 35% Combination = 68% |
| JJN-3R | ++ | − | +++ | MDX-1338 = 100% |
| JJN-3 | ++ | − | +++ | |
| RPMI-8226 | ++ | − | ++ | MDX-1338 = 61% Comb w/ Lenalid. = 90% Comb w/ Bortez. = 82% |
| MM.1S | + | − | ++ | MDX-1338 = 60% REVLIMID ® = 70% Combination = 86% |
| OPM-2 | ++ | − | ++ | MDX-1338 = 46% Comb w/ Bortez. = 92% |

Figure 18H:
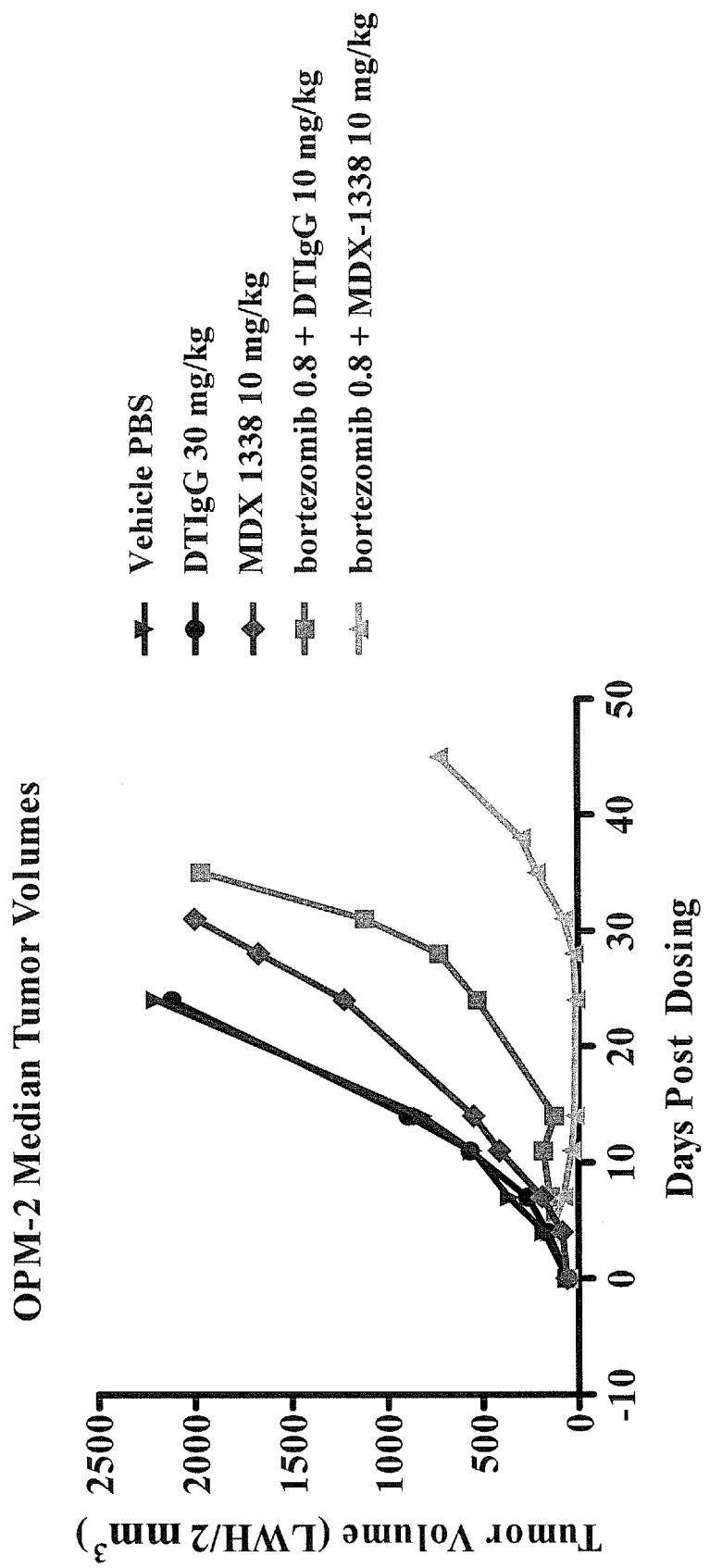
Figure 18I:
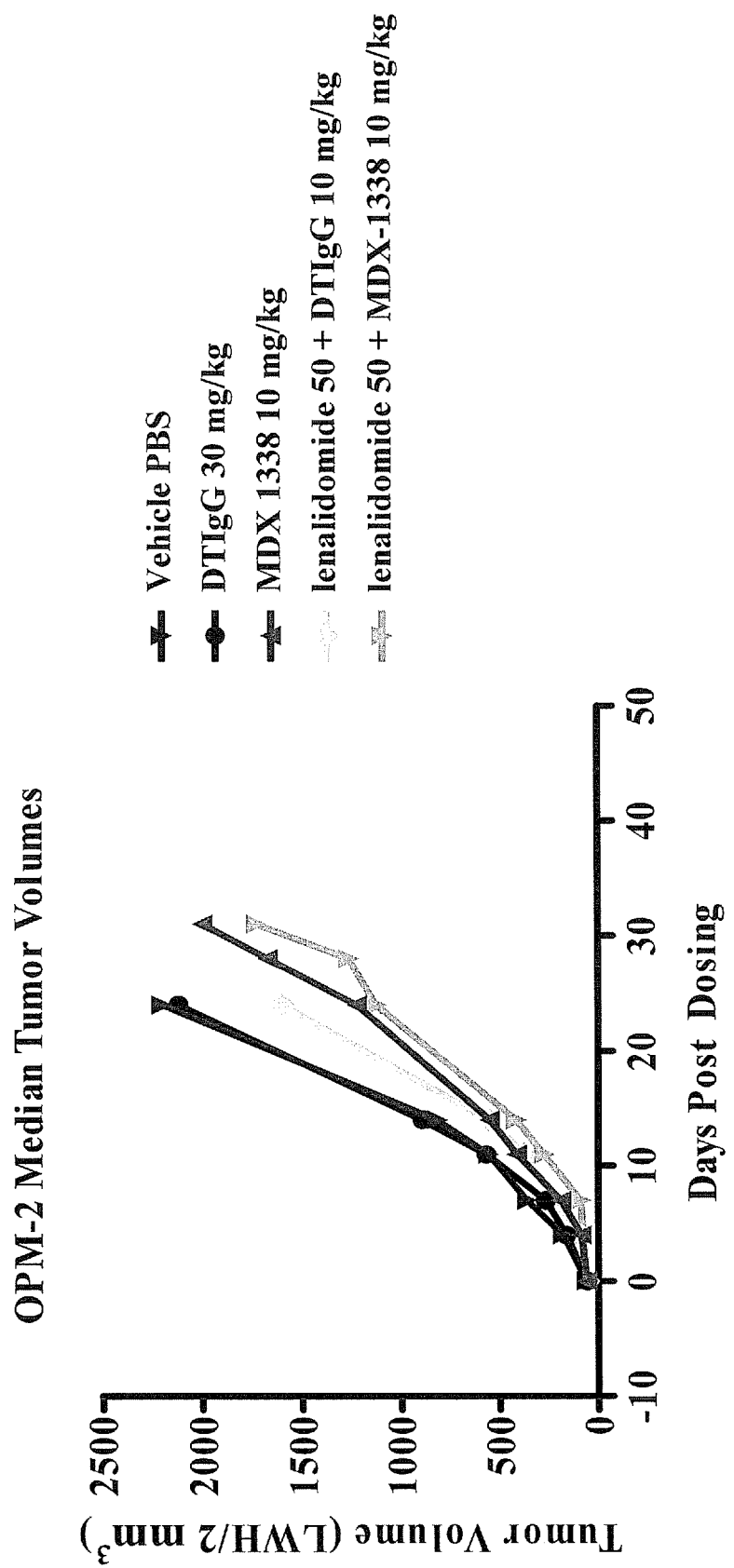

OPM-2 cells (10 million) were implanted into SCID mice as described. At a tumor volume of approximately 77 mm$^3$, the mice were randomized (n=8), dosed with MDX-1338 (10 mg/kg/dose IP) alone or in combination with bortezomib (0.8 mg/kg/dose IV) or lenalidomide (50 mg/kg/dose IP) on Days 0, 4, 7, 11 and 14. MDX-1338 inhibited median tumor growth by 45% at Day 24 compared to mice treated with the vehicle control (FIG. 18H). Bortezomib inhibited tumor growth by 75% at Day 24, and the combination of MDX-1338 and bortezomib was highly efficacious, inhibiting median tumor growth by 99% at Day 24 (FIG. 18H). Lenalidomide exhibited minimal efficacy in this OPM-2 model, and it did not significantly enhance the efficacy of MDX-1338 (FIG. 18I).

The tumor growth inhibition results obtained on these MM cell xenografts are summarized in Table 9, together with CXCR4 expression and susceptibility to apoptosis induced by MDX-1338.

Examples 14-16 demonstrate that when given as monotherapy on established tumors, BMS-936564 exhibits antitumor activity in multiple NHL, AML and MM xenograft models. Since BMS-936564 is an IgG4 antibody, it does not elicit complement-dependent cytotoxicity (CDC) or antibody-dependent cell-mediated cytotoxicity (ADCC). The data provided in Example 11 suggest that BMS-936564 induces apoptosis as one mechanism of tumor growth inhibition.

REFERENCES

Alsayed Y et al. (2007) *Blood* 109(7):2708-17.
Amadori S et al. (1991) *J Clin Oncol* 9(7):1210-4.

Angal S et al. (1993) *Mol Immunol* 30(1):105-8.
Azab A K et al. (2009) *Blood* 113(18):4341-51.
Beider K et al. (2011) *Exp Hematol* 39(3):282-92.
Berndt C et al. (1998) *Proc Nad Acad Sci USA* 95:12556-61.
Bertolini F et al. (2002) *Cancer Res* 62(11):3106-12.
Bleul C C et al. (1996) *Nature* 382(6594):829-33.
Breems D A et al. (2005) *J Clin Oncol* 23(9):1969-78.
Broxmeyer H E et al. (2005) *J Exp Med* 201:1307-18.
Burger J A et al. (1999) *Blood* 94:3658-67.
*Cancer Facts and FIGS.* 2008, American Cancer Society, Atlanta Ga. (2008).
Carnec X et al. (2005) *J Virol* 79:1930-8.
Chow K U et al. (2002) *Haematologica* 87:33-43.
Corcione A et al. (2000) *J Natl Cancer Inst* 92:628-35.
Corvata N et al. (2011) Poster presented at 102nd Annual Meeting of the American Association for Cancer Research, Apr. 2-6, 2011, Orlando, Fla.
Crazzolara R et. al. (2001) *Br J Haematol* 115:545-53.
Dar A et al. (2011) *Leukemia* 25(8):1286-96.
Devine S M et al. (2004) *J Clin Oncol* 22:1095-102.
Di Salvo J et al. (2000) *Eur J Pharmacol* 409:143-154.
Feng Y et al. (1996) *Science* 272:872-7.
Flomenberg N et al. (2005) *Blood* 106:1867-74.
Friedberg J W et al. (2008) *J Clin Oncol* 26(2):204-10.
Garg H et al. (2006) *J Leukocyte Biol* 79:351-62.
Gazitt Y (2001) *J Hematother Stem Cell Res* 10:229-36.
Geminder et al. (2001) *J Immunol* 167:4747-57.
Gisselbrecht C et al. (2011) Novel Agents for Diffuse Large B-cell Lymphoma, ASCO Education Book 2011, page 321.
Gisselbrecht C et al. (2010) *J Clin Oncol* 28:4184-90.
Gonzalo J A et al. (2000) *J Immunol* 165:499-508.
Guleng B et al. (2005) *Cancer Res* 65(13):5864-71.
Gupta S K et al. (1998) *J Biol Chem* 273(7):4282-7.
Hesselgesser J et al. (1997) *Curr Biol* 7(2):112-21.
Hiller D J et al. (2011) *Surgery* 150(3):459-65.
Hollinger et al. (2005) *Nature Biotech* 23(9):1126-36.
Hosokawa Y et al. (2005) *Clin Exp Immunol* 141:467-74.
Hou T et al. (1998) *J Immunol* 160:180-8.
Hwang J H et al. (2003) *J Clin Endocrinol Metab* 88:408-16.
Jemal A et al. (2005) *CA Cancer J Clin* 55:10-50.
Jemal A et al. (2008) *CA Cancer J Clin* 58:71-96.
Jemal A et al. (2009) *CA Cancer J Clin* 59:225-49.
Jiang Y P et al. (2006) *Gynecol Oncol* 103(1):226-33.
Jin D K et al. (2006) *Nat Med* 12:557-67.
Jin L et al. (2008) *Mol Cancer Ther* 7:48-58.
Kabat E A et al. (1991) *Sequences of Proteins of Immunological Interest*, Fifth Edition, U.S. Department of Health and Human Services, NIH Publication No. 91-3242.
Kashyap M K, Kumar D, Jones H, Melo-Cardenas J, Kuhne M R, Sabbatini P, Cohen L J, Cardarelli J M, Kipps T J and Castro J E (2012) Abstract for presentation at American Society of Hematology (ASH) 54$^{th}$ Annual Meeting, Dec. 8-11, 2012, Atlanta, Ga.
Kewalramani T et al. (2004) *Blood* 103(10):3684-8.
Koshiba T et al. (2000) *Clin Cancer Res* 6:3530-5.
Laverdiere C et al. (2005) *Clin Cancer Res* 11:2561-7.
Lee B et al. (1999) *Proc Natl Acad Sci USA* 96(9):5215-20.
Libura J et al. (2002) *Blood* 100:2597-606.
Loetscher M et al. (1994) *J Biol Chem* 269(1):232-7.
Lonberg N et al. (1994) *Nature* 368 (6474):856-859.
Liu Z et al. (2011) *Diabetologia* 54(8):2067-76.
Marechal R et al. (2009) *Brit J Cancer* 100(9):1444-51.
Matthys P et al. (2001) *J Immunol* 167:4686-92.
Mohle R et al. (1998) *Blood* 91(12):4523-30.
Mohle R et al. (1999) *Leukemia* 13:1954-9.
Muller A et al. (2001) *Nature* 410:50-6.
Murphy P M (2001) *New Engl J Med* 345(11):833-5.
Nervi B et al. (2009) *Blood* 113:6206-14.
Oberlin E et al. (1996) *Nature* 382:833-5.
Olafsen et al. (2010) *Semin Nucl Med* 40(3):167-81.
Ottaiano A et al. (2006) *Clin Cancer Res* 12(9):2795-803.
PCT Publication No. WO 02/43478, published Jun. 6, 2002 by Medarex, Inc. and Kirin Beer Kabushiki Kaisha.
PCT Publication No. WO 2008/060367, published May 22, 2008 by Medarex, Inc.
PCT Publication No. WO 2008/142303, published Nov. 27, 2008 by Pierre Fabre Medicament.
PCT Publication No. WO 2009/140124, published Nov. 19, 2009 by Eli Lilly and Co.
PCT Publication No. WO 2010/043650, published Apr. 22, 2010 by Ablynx N V.
Ping Y F et al. (2011) *J Pathol* 224(3):344-54.
Porvasnik S et al. (2009) *The Prostate* 69:1460-9.
Raab M S et al. (2009) *Lancet* 374 (9686):324-39.
Rempel S A et al. (2000) *Clin Cancer Res* 6:102-11.
Richert M et al. (2009) *Oncol Rep* 21:76-7.
Righi E et al. (2011) *Cancer Res* 71(16):5522-34.
Robinson J R (ed.) (1978) *Sustained and Controlled Release Drug Delivery Systems*, Marcel Dekker, Inc., New York.
Roccaro A M, Sacco A, Kuhne M, Azab A, Maiso P, Zhang Y, Liu Y, Michaela R, Ngo H T, Quang P, Cardarelli J A and Ghobrial I M (2012) Abstract for presentation at American Society of Hematology (ASH) 54$^{th}$ Annual Meeting, Dec. 8-11, 2012, Atlanta, Ga.
Rombouts E J C et al. (2004) *Blood* 104:550-7.
Rummel M J et al. (2002) *Semin Oncol* 29 (Suppl. 13):12-4.
Scala S et al. (2005) *Clin Cancer Res* 11:1835-41.
Scotton C et al. (2001) *Br. J. Cancer* 85:891-7.
Schrader A J et al. (2002) *Br J Cancer* 86:1250-6.
Siegel R et al. (2011) *CA Cancer J Clin* 61(4):212-36.
Singer C R and Goldstone A H (1986) *Clin Haematol* 15:105.
Spano J P et al. (2004) *Ann Oncol* 15:613-7.
Spoo A C et al. (2007) *Blood* 109(2):786-91.
Staller P et al. (2003) *Nature* 425:307-11.
Tachibana K et al. (1998) *Nature* 393(6685):591-4.
Taichman R S et al. (2002) *Cancer Res* 62:1832-7.
Tavor S et al. (2004) *Cancer Res* 64(8):2817-24.
Terada R et al. (2003) *Lab Invest* 83:665-72.
U.S. Pat. No. 5,399,163, issued Mar. 21, 1995 to Petersen S F et al.
U.S. Pat. No. 5,383,851, issued Jan. 24, 1995 to McKinnon, Jr. C N et al.
U.S. Pat. No. 4,941,880, issued Jul. 17, 1990 to Burns M.
U.S. Pat. No. 6,794,132, issued Sep. 21, 2004 to Buechler J et al.
U.S. Pat. No. 7,041,870, issued May 9, 2006 to Tomizuka K et al.
U.S. Pat. No. 7,674,618, issued Mar. 9, 2010 to Black A.
U.S. Publication 2012/0052097, published Mar. 1, 2012 by Fetzer O S et al.
Vicari A P et al. (2002) *Cytokine Growth Factor Rev* 13:143-154.
Wang N et al. (2005) *J Transl Med* 3:26-33.
Weng A P et al. (2003) *Am J Clin Pathol* 119:424-30.
Zeelenberg I S et al. (2003) *Cancer Res* 63:3833-9.
Zeng Z et al. (2009) *Blood* 113(24):6215-24.
Zhang et al. (2002) *J Biol Chem* 277(27):24515-21.
Zou Y et al. (1998) *Nature* 393(6685):595-9.

What is claimed is:

1. A method for inducing apoptosis of multiple myeloma cells in a subject afflicted with multiple myeloma, said method comprising administering to the subject a therapeutically effective amount of an antibody or an antigen-binding fragment thereof which specifically binds to a human CXCR4 receptor and comprises a heavy chain variable region comprising CDR1, CDR2 and CDR3 domains comprising consecutively linked amino acids having the sequences set forth in SEQ ID NO: 1, SEQ ID NO: 5 and SEQ ID NO: 9, respectively, and a light chain variable region comprising CDR1, CDR2 and CDR3 domains comprising consecutively linked amino acids having the sequences set forth in SEQ ID NO: 13, SEQ ID NO: 17 and SEQ ID NO: 21, respectively.

2. The method of claim 1, wherein the multiple myeloma is relapsed or refractory multiple myeloma.

3. The method of claim 1, wherein the antibody or fragment thereof is administered to the subject as monotherapy.

4. The method of claim 1, wherein the antibody or fragment thereof is administered to the subject in combination with surgery, radiation and/or one or more therapeutic agents.

5. The method of claim 1, wherein the antibody or fragment thereof inhibits the activity of the CXCR4 receptor and increases sensitivity of the multiple myeloma cell to a chemotherapeutic agent.

6. The method of claim 1, further comprising administering at least one chemotherapeutic agent in combination with the antibody or fragment thereof.

7. The method of claim 6, wherein the at least one chemotherapeutic agent is:
(a) lenalidomide and dexamethasone; or
(b) bortezomib and dexamethasone.

8. The method of claim 1, wherein the antibody or fragment thereof is a chimeric, humanized, or human antibody or a fragment thereof.

9. The method of claim 1, wherein the antibody or fragment thereof comprises a heavy chain variable region comprising consecutively linked amino acids having the sequence set forth in SEQ ID NO: 25, and a light chain variable region comprising consecutively linked amino acids having the sequence set forth in SEQ ID NO: 29.

10. The method of claim 1, wherein the antibody is ulocuplumab (BMS-936564).

11. The method of claim 1, wherein the antibody or fragment thereof is an IgG1 or IgG4 antibody or a fragment thereof.

12. The method of claim 3, wherein the antibody or fragment thereof is administered to the subject at a dose ranging from about 0.1 to 10 mg/kg body weight.

13. The method of claim 12, wherein the dose is 0.3, 1, 3 or 10 mg/kg body weight.

14. The method of claim 7, wherein ulocuplumab (BMS-936564) or a fragment thereof is administered to the subject in combination with lenalidomide and dexamethasone in a dosage regimen comprising:
(a) ulocuplumab (1, 3, or 10 mg/kg) administered as an intravenous infusion on Days 1, 8, 15, 22, 29 and 36 (Cycle 1) and on Days 1, 8, 15, and 22 (Cycle 2 and subsequent cycles);
(b) lenalidomide (25 mg) orally administered for 21 days (Days 15-35; Cycle 1) and Days 1-21 (Cycle 2 and subsequent cycles); and
(c) dexamethasone (40 mg) administered on Days 15, 22, 29, and 36 (Cycle 1) and on Days 1, 8, 15, and 22 (Cycle 2 and subsequent cycles).

15. The method of claim 7, wherein ulocuplumab (BMS-936564) or a fragment thereof is administered to the subject in combination with bortezomib and dexamethasone in a dosage regimen comprising:
(a) ulocuplumab (1, 3, or 10 mg/kg) administered as an intravenous infusion on Days 1, 8, 15, 22 and 29 (Cycle 1) and on Days 1, 8 and 15 (Cycle 2 and subsequent cycles);

(b) bortezomib (1.3 mg/m²) administered as an intravenous push on Days 15, 18, 22, and 25 (Cycle 1) and on Days 1, 4, 8, 11 (Cycle 2 and subsequent cycles); and (c) dexamethasone (20 mg) administered on Days 15, 16, 18, 19, 22, 23, 25 and 26 (Cycle 1) and on Days 1, 2, 4, 5, 8, 9, 11 and 12 (Cycle 2 and subsequent cycles).

16. The method of claim 1, wherein the antibody or fragment thereof is a monoclonal antibody or a fragment thereof.

17. A method for inhibiting tumor growth and/or inducing apoptosis of multiple myeloma cells in a subject afflicted with multiple myeloma, said method comprising administering to the subject a therapeutically effective amount of an antibody or an antigen-binding fragment thereof which specifically binds to a human CXCR4 receptor and comprises a heavy chain variable region comprising CDR1, CDR2 and CDR3 domains comprising consecutively linked amino acids having the sequences set forth in SEQ ID NO: 1, SEQ ID NO: 5 and SEQ ID NO: 9, respectively, and a light chain variable region comprising CDR1, CDR2 and CDR3 domains comprising consecutively linked amino acids having the sequences set forth in SEQ ID NO: 13, SEQ ID NO: 17 and SEQ ID NO: 21, respectively, wherein the antibody or fragment thereof is administered to the subject as monotherapy.

18. The method of claim 17, wherein the multiple myeloma is relapsed or refractory multiple myeloma.

19. The method of claim 17, wherein the antibody or fragment thereof is a monoclonal antibody or a fragment thereof.

20. The method of claim 17, wherein the antibody or fragment thereof is a chimeric, humanized, or human antibody or a fragment thereof.

21. The method of claim 17, wherein the antibody or fragment thereof is an IgG1 or IgG4 antibody or a fragment thereof.

22. The method of claim 17, wherein the antibody or fragment thereof comprises a heavy chain variable region comprising consecutively linked amino acids having the sequence set forth in SEQ ID NO: 25, and a light chain variable region comprising consecutively linked amino acids having the sequence set forth in SEQ ID NO: 29.

23. The method of claim 17, wherein the antibody is ulocuplumab (BMS-936564).

24. The method of claim 17, wherein the antibody or fragment thereof is administered to the subject at a dose ranging from about 0.1 to 10 mg/kg body weight.

25. The method of claim 24, wherein the dose is 0.3, 1, 3 or 10 mg/kg body weight.

* * * * *

SEQUENCE LISTING

<160> NUMBER OF SEQ ID NOS: 51

<210> SEQ ID NO 1
<211> LENGTH: 5
<212> TYPE: PRT
<213> ORGANISM: Homo sapiens

<400> SEQUENCE: 1

Ser Tyr Ser Met Asn
1               5

<210> SEQ ID NO 2
<211> LENGTH: 5
<212> TYPE: PRT
<213> ORGANISM: Homo sapiens

<400> SEQUENCE: 2

Ser Tyr Ser Met Asn
1               5

<210> SEQ ID NO 3
<211> LENGTH: 5
<212> TYPE: PRT
<213> ORGANISM: Homo sapiens

<400> SEQUENCE: 3

Ser Tyr Ser Met Asn
1               5

<210> SEQ ID NO 4
<211> LENGTH: 5
<212> TYPE: PRT
<213> ORGANISM: Homo sapiens

<400> SEQUENCE: 4

Ser Tyr Ser Met Asn
1               5

<210> SEQ ID NO 5
<211> LENGTH: 17
<212> TYPE: PRT
<213> ORGANISM: Homo sapiens

<400> SEQUENCE: 5

Tyr Ile Ser Ser Arg Ser Arg Thr Ile Tyr Tyr Ala Asp Ser Val Lys
1               5                   10                  15

Gly

<210> SEQ ID NO 6
<211> LENGTH: 17
<212> TYPE: PRT
<213> ORGANISM: Homo sapiens

<400> SEQUENCE: 6

Tyr Ile Ser Ser Arg Ser Arg Ser Ile Tyr Tyr Ala Asp Ser Val Lys
1               5                   10                  15

Gly

<210> SEQ ID NO 7
<211> LENGTH: 17
<212> TYPE: PRT
<213> ORGANISM: Homo sapiens

<400> SEQUENCE: 7

```
Tyr Ile Ser Ser Arg Ser Lys Thr Ile Tyr Tyr Ala Asp Ser Val Lys
1               5                   10                  15

Gly

<210> SEQ ID NO 8
<211> LENGTH: 17
<212> TYPE: PRT
<213> ORGANISM: Homo sapiens

<400> SEQUENCE: 8

Tyr Ile Ser Ser Arg Ser Arg Thr Ile Tyr Tyr Ala Asp Ser Val Lys
1               5                   10                  15

Gly

<210> SEQ ID NO 9
<211> LENGTH: 16
<212> TYPE: PRT
<213> ORGANISM: Homo sapiens

<400> SEQUENCE: 9

Asp Tyr Gly Gly Gln Pro Pro Tyr Tyr Tyr Tyr Gly Met Asp Val
1               5                   10                  15

<210> SEQ ID NO 10
<211> LENGTH: 16
<212> TYPE: PRT
<213> ORGANISM: Homo sapiens

<400> SEQUENCE: 10

Asp Tyr Gly Gly Gln Pro Pro Tyr Tyr Tyr Tyr Gly Met Asp Val
1               5                   10                  15

<210> SEQ ID NO 11
<211> LENGTH: 16
<212> TYPE: PRT
<213> ORGANISM: Homo sapiens

<400> SEQUENCE: 11

Asp Tyr Gly Gly Gln Pro Pro Tyr Tyr Tyr Tyr Gly Met Asp Val
1               5                   10                  15

<210> SEQ ID NO 12
<211> LENGTH: 16
<212> TYPE: PRT
<213> ORGANISM: Homo sapiens

<400> SEQUENCE: 12

Asp Tyr Gly Gly Gln Pro Pro Tyr His Tyr Tyr Gly Met Asp Val
1               5                   10                  15

<210> SEQ ID NO 13
<211> LENGTH: 11
<212> TYPE: PRT
<213> ORGANISM: Homo sapiens

<400> SEQUENCE: 13

Arg Ala Ser Gln Gly Ile Ser Ser Trp Leu Ala
1               5                   10

<210> SEQ ID NO 14
<211> LENGTH: 11
<212> TYPE: PRT
<213> ORGANISM: Homo sapiens
```

<400> SEQUENCE: 14

Arg Ala Ser Gln Gly Ile Ser Ser Trp Leu Ala
1               5                   10

<210> SEQ ID NO 15
<211> LENGTH: 11
<212> TYPE: PRT
<213> ORGANISM: Homo sapiens

<400> SEQUENCE: 15

Arg Thr Ser Gln Gly Ile Ser Ser Trp Leu Ala
1               5                   10

<210> SEQ ID NO 16
<211> LENGTH: 11
<212> TYPE: PRT
<213> ORGANISM: Homo sapiens

<400> SEQUENCE: 16

Arg Ala Ser Gln Gly Ile Ser Asn Trp Leu Ala
1               5                   10

<210> SEQ ID NO 17
<211> LENGTH: 7
<212> TYPE: PRT
<213> ORGANISM: Homo sapiens

<400> SEQUENCE: 17

Ala Ala Ser Ser Leu Gln Ser
1               5

<210> SEQ ID NO 18
<211> LENGTH: 7
<212> TYPE: PRT
<213> ORGANISM: Homo sapiens

<400> SEQUENCE: 18

Ala Ala Ser Ser Leu Gln Ser
1               5

<210> SEQ ID NO 19
<211> LENGTH: 7
<212> TYPE: PRT
<213> ORGANISM: Homo sapiens

<400> SEQUENCE: 19

Ala Ala Ser Ser Leu Gln Ser
1               5

<210> SEQ ID NO 20
<211> LENGTH: 7
<212> TYPE: PRT
<213> ORGANISM: Homo sapiens

<400> SEQUENCE: 20

Ala Ala Ser Ser Leu Gln Ser
1               5

<210> SEQ ID NO 21
<211> LENGTH: 9
<212> TYPE: PRT
<213> ORGANISM: Homo sapiens

<400> SEQUENCE: 21

```
Gln Gln Tyr Asn Ser Tyr Pro Arg Thr
1               5

<210> SEQ ID NO 22
<211> LENGTH: 9
<212> TYPE: PRT
<213> ORGANISM: Homo sapiens

<400> SEQUENCE: 22

Gln Gln Tyr Asn Ser Tyr Pro Arg Thr
1               5

<210> SEQ ID NO 23
<211> LENGTH: 9
<212> TYPE: PRT
<213> ORGANISM: Homo sapiens

<400> SEQUENCE: 23

Gln Gln Tyr Asn Ser Tyr Pro Arg Thr
1               5

<210> SEQ ID NO 24
<211> LENGTH: 9
<212> TYPE: PRT
<213> ORGANISM: Homo sapiens

<400> SEQUENCE: 24

Gln Gln Tyr Asn Ser Tyr Pro Arg Thr
1               5

<210> SEQ ID NO 25
<211> LENGTH: 125
<212> TYPE: PRT
<213> ORGANISM: Homo sapiens

<400> SEQUENCE: 25

Gln Val Gln Leu Val Gln Ser Gly Gly Gly Leu Val Gln Pro Gly Gly
1               5                   10                  15

Ser Leu Arg Leu Ser Cys Ala Ala Ala Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Arg Ser Arg Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Tyr Tyr Tyr Tyr Gly Met
            100                 105                 110

Asp Val Trp Gly Gln Gly Thr Thr Val Thr Val Ser Ser
            115                 120                 125

<210> SEQ ID NO 26
<211> LENGTH: 125
<212> TYPE: PRT
<213> ORGANISM: Homo sapiens

<400> SEQUENCE: 26

Gln Val Gln Leu Val Gln Ser Gly Gly Gly Leu Val Gln Pro Gly Gly
1               5                   10                  15
```

Ser Leu Arg Leu Ser Cys Ala Ala Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Arg Ser Arg Ser Ile Tyr Tyr Ala Asp Ser Val
50                      55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr Tyr Tyr Tyr Gly Met
                100                 105                 110

Asp Val Trp Gly Gln Gly Thr Thr Val Thr Val Ser Ser
            115                 120                 125

<210> SEQ ID NO 27
<211> LENGTH: 125
<212> TYPE: PRT
<213> ORGANISM: Homo sapiens

<400> SEQUENCE: 27

Glu Val Gln Leu Val Gln Ser Gly Gly Gly Leu Val Gln Pro Gly Gly
1               5                   10                  15

Ser Leu Arg Leu Ser Cys Ala Ala Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Arg Ser Lys Thr Ile Tyr Tyr Ala Asp Ser Val
50                      55                  60

Lys Gly Arg Phe Thr Ile Ser Arg Asp Asn Ala Arg Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr Tyr Tyr Tyr Gly Met
                100                 105                 110

Asp Val Trp Gly Gln Gly Thr Thr Val Thr Val Ser Ser
            115                 120                 125

<210> SEQ ID NO 28
<211> LENGTH: 125
<212> TYPE: PRT
<213> ORGANISM: Homo sapiens

<400> SEQUENCE: 28

Glu Val Gln Leu Val Gln Ser Gly Gly Gly Leu Val Gln Pro Gly Gly
1               5                   10                  15

Ser Leu Arg Leu Ser Cys Ala Ala Gly Phe Thr Phe Ser Ser Tyr
            20                  25                  30

Ser Met Asn Trp Val Arg Gln Ala Pro Gly Lys Gly Leu Glu Trp Val
            35                  40                  45

Ser Tyr Ile Ser Ser Arg Ser Arg Thr Ile Tyr Tyr Ala Asp Ser Val
50                      55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

```
Ala Arg Asp Tyr Gly Gly Gln Pro Pro Tyr His Tyr Tyr Gly Met
            100                 105                 110

Asp Val Trp Gly Gln Gly Thr Thr Val Thr Val Ser Ser
            115                 120                 125

<210> SEQ ID NO 29
<211> LENGTH: 107
<212> TYPE: PRT
<213> ORGANISM: Homo sapiens

<400> SEQUENCE: 29

Ala Ile Arg Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Val Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 30
<211> LENGTH: 107
<212> TYPE: PRT
<213> ORGANISM: Homo sapiens

<400> SEQUENCE: 30

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Pro Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 31
<211> LENGTH: 107
<212> TYPE: PRT
<213> ORGANISM: Homo sapiens

<400> SEQUENCE: 31

Val Ile Trp Val Thr Gln Ser Pro Ser Ser Leu Ser Ala Ser Val Gly
1               5                   10                  15

Asp Arg Val Thr Ile Thr Cys Thr Ser Gln Gly Ile Ser Ser Trp
            20                  25                  30
```

Leu Ala Trp Tyr Gln Gln Lys Pro Glu Lys Ala Pro Glu Leu Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 32
<211> LENGTH: 107
<212> TYPE: PRT
<213> ORGANISM: Homo sapiens

<400> SEQUENCE: 32

Glu Ile Val Leu Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
            35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 33
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 33 cag gtg cag ctg gtg cag tct ggg gga ggc ttg gta cag cct ggg ggg    48
Gln Val Gln Leu Val Gln Ser Gly Gly Gly Leu Val Gln Pro Gly Gly
1               5                   10                  15 tcc ctg aga ctc tcc tgt gca gcc gct gga ttc acc ttc agt agc tat    96
Ser Leu Arg Leu Ser Cys Ala Ala Ala Gly Phe Thr Phe Ser Ser Tyr
            20                  25                  30 agc atg aac tgg gtc cgc cag gct cca ggg aag ggg ctg gag tgg gtt   144
Ser Met Asn Trp Val Arg Gln Ala Pro Gly Lys Gly Leu Glu Trp Val
        35                  40                  45 tca tac att agt agt aga agt aga acc ata tac tac gca gac tct gtg   192
Ser Tyr Ile Ser Ser Arg Ser Arg Thr Ile Tyr Tyr Ala Asp Ser Val
    50                  55                  60 aag ggc cga ttc acc atc tcc aga gac aat gcc aag aac tca ctg tat   240
Lys Gly Arg Phe Thr Ile Ser Arg Asp Asn Ala Lys Asn Ser Leu Tyr
65                  70                  75                  80 ctg caa atg aac agc ctg aga gac gag gac acg gct gtg tat tac tgt   288
Leu Gln Met Asn Ser Leu Arg Asp Glu Asp Thr Ala Val Tyr Tyr Cys
                85                  90                  95

```
gcg aga gat tac ggt ggt caa ccc cct tac tac tac tac tac ggt atg      336
Ala Arg Asp Tyr Gly Gly Gln Pro Pro Tyr Tyr Tyr Tyr Tyr Gly Met
                100             105                 110 gac gtc tgg ggc caa ggg acc acg gtc acc gtc tcc tca                   375
Asp Val Trp Gly Gln Gly Thr Thr Val Thr Val Ser Ser
        115                 120                 125

<210> SEQ ID NO 34
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 34 cag gtg cag ctg gtg cag tct ggg gga ggc ttg gta cag cct ggg ggg        48
Gln Val Gln Leu Val Gln Ser Gly Gly Gly Leu Val Gln Pro Gly Gly
1               5                  10                  15 tcc ctg aga ctc tcc tgt gca gcc gct gga ttc acc ttc agt agc tat        96
Ser Leu Arg Leu Ser Cys Ala Ala Ala Gly Phe Thr Phe Ser Ser Tyr
            20                  25                  30 agc atg aac tgg gtc cgc cag gct cca ggg aag ggg ctg gag tgg gtt       144
Ser Met Asn Trp Val Arg Gln Ala Pro Gly Lys Gly Leu Glu Trp Val
        35                  40                  45 tca tac att agt agt aga agt aga agc ata tac tac gca gac tct gtg       192
Ser Tyr Ile Ser Ser Arg Ser Arg Ser Ile Tyr Tyr Ala Asp Ser Val
    50                  55                  60 aag ggc cga ttc acc atc tcc aga gac aat gcc aag aac tca ctg tac       240
Lys Gly Arg Phe Thr Ile Ser Arg Asp Asn Ala Lys Asn Ser Leu Tyr
65                  70                  75                  80 ctg caa atg aac agc ctg aga gac gag gac acg gct gtg tat tac tgt       288
Leu Gln Met Asn Ser Leu Arg Asp Glu Asp Thr Ala Val Tyr Tyr Cys
                85                  90                  95 gcg aga gat tac ggt ggt caa ccc cct tac tac tac tac tac ggt atg       336
Ala Arg Asp Tyr Gly Gly Gln Pro Pro Tyr Tyr Tyr Tyr Tyr Gly Met
                100             105                 110 gac gtc tgg ggc caa ggg acc acg gtc acc gtc tcc tca                   375
Asp Val Trp Gly Gln Gly Thr Thr Val Thr Val Ser Ser
        115                 120                 125

<210> SEQ ID NO 35
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 35 gag gtg cag ctg gtg cag tct ggg gga ggc ttg gta cag cct ggg ggg        48
Glu Val Gln Leu Val Gln Ser Gly Gly Gly Leu Val Gln Pro Gly Gly
1               5                  10                  15 tcc ctg aga ctc tcc tgt gca gcc gct gga ttc acc ttc agt agc tat        96
Ser Leu Arg Leu Ser Cys Ala Ala Ala Gly Phe Thr Phe Ser Ser Tyr
            20                  25                  30 agc atg aac tgg gtc cgc cag gct cca ggg aag ggg ctg gag tgg gtt       144
Ser Met Asn Trp Val Arg Gln Ala Pro Gly Lys Gly Leu Glu Trp Val
        35                  40                  45 tca tac att agt agt cgt agt aaa acc ata tac tac gca gac tct gtg       192
Ser Tyr Ile Ser Ser Arg Ser Lys Thr Ile Tyr Tyr Ala Asp Ser Val
    50                  55                  60 aag ggc cga ttc acc atc tcc aga gac aat gcc agg aac tca ctg tat       240
```

```
Lys Gly Arg Phe Thr Ile Ser Arg Asp Asn Ala Arg Asn Ser Leu Tyr
 65                  70                  75                  80 ctg caa atg aac agc ctg aga gac gag gac acg gct gtg tat tac tgt        288
Leu Gln Met Asn Ser Leu Arg Asp Glu Asp Thr Ala Val Tyr Tyr Cys
                 85                  90                  95 gcg aga gat tac ggt ggt caa ccc cct tac tac tac tac ggt atg            336
Ala Arg Asp Tyr Gly Gly Gln Pro Pro Tyr Tyr Tyr Tyr Gly Met
            100                 105                 110 gac gtc tgg ggc caa ggg acc acg gtc acc gtc tcc tca                    375
Asp Val Trp Gly Gln Gly Thr Thr Val Thr Val Ser Ser
        115                 120                 125

<210> SEQ ID NO 36
<211> LENGTH: 375
<212> TYPE: DNA
<213> ORGANISM: Homo sapiens
<220> FEATURE:
<221> NAME/KEY: CDS
<222> LOCATION: (1)..(375)

<400> SEQUENCE: 36 gag gtg cag ctg gtg cag tct ggg gga ggc ttg gta cag cct ggg ggg        48
Glu Val Gln Leu Val Gln Ser Gly Gly Gly Leu Val Gln Pro Gly Gly
 1               5                  10                  15 tcc ctg aga ctc tcc tgt gca gcc gct gga ttc acc ttc agt agc tat        96
Ser Leu Arg Leu Ser Cys Ala Ala Ala Gly Phe Thr Phe Ser Ser Tyr
             20                  25                  30 agc atg aac tgg gtc cgc cag gct cca ggg aag ggg ctg gag tgg gtt        144
Ser Met Asn Trp Val Arg Gln Ala Pro Gly Lys Gly Leu Glu Trp Val
         35                  40                  45 tca tac att agt agt aga agt aga acc ata tac tac gca gac tct gtg       192
Ser Tyr Ile Ser Ser Arg Ser Arg Thr Ile Tyr Tyr Ala Asp Ser Val
     50                  55                  60 aag ggc cga ttc acc atc tcc aga gac aat gcc aag aac tca ctg tat       240
Lys Gly Arg Phe Thr Ile Ser Arg Asp Asn Ala Lys Asn Ser Leu Tyr
 65                  70                  75                  80 ctg caa atg aac agc ctg aga gac gag gac acg gct gtg tat tac tgt       288
Leu Gln Met Asn Ser Leu Arg Asp Glu Asp Thr Ala Val Tyr Tyr Cys
                 85                  90                  95 gcg aga gat tac ggt ggt caa ccc cct tac cac tac tac ggt atg           336
Ala Arg Asp Tyr Gly Gly Gln Pro Pro Tyr His Tyr Tyr Gly Met
            100                 105                 110 gac gtc tgg ggc caa ggg acc acg gtc acc gtc tcc tca                   375
Asp Val Trp Gly Gln Gly Thr Thr Val Thr Val Ser Ser
        115                 120                 125

<210> SEQ ID NO 37
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 37 gcc atc cgg atg acc cag tct cca tcc tca ctg tct gca tct gta gga       48
Ala Ile Arg Met Thr Gln Ser Pro Ser Ser Leu Ser Ala Ser Val Gly
 1               5                  10                  15 gac aga gtc acc atc act tgt cgg gcg agt cag ggt att agc agc tgg       96
Asp Arg Val Thr Ile Thr Cys Arg Ala Ser Gln Gly Ile Ser Ser Trp
             20                  25                  30 tta gcc tgg tat cag cag aaa cca gag aaa gcc cct aag tcc ctg atc      144
Leu Ala Trp Tyr Gln Gln Lys Pro Glu Lys Ala Pro Lys Ser Leu Ile
```

```
                35                  40                  45
tat gct gca tcc agt ttg caa agt ggg gtc cca tca agg ttc agc ggc      192
Tyr Ala Ala Ser Ser Leu Gln Ser Gly Val Pro Ser Arg Phe Ser Gly
     50                  55                  60 agt gga tct ggg aca gat ttc act ctc acc atc agc agc ctg cag cct      240
Ser Gly Ser Gly Thr Asp Phe Thr Leu Thr Ile Ser Ser Leu Gln Pro
 65                  70                  75                  80 gaa gat ttt gta act tat tac tgc caa cag tat aat agt tac cct cgg      288
Glu Asp Phe Val Thr Tyr Tyr Cys Gln Gln Tyr Asn Ser Tyr Pro Arg
                 85                  90                  95 acg ttc ggc caa ggg acc aag gtg gaa atc aaa                          321
Thr Phe Gly Gln Gly Thr Lys Val Glu Ile Lys
            100                 105

<210> SEQ ID NO 38
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 38 gaa att gtg ctc acc cag tct cca tcc tca ctg tct gca tct gta gga       48
Glu Ile Val Leu Thr Gln Ser Pro Ser Ser Leu Ser Ala Ser Val Gly
 1               5                  10                  15 gac aga gtc acc atc act tgt cgg gcg agt cag ggt att agc agc tgg       96
Asp Arg Val Thr Ile Thr Cys Arg Ala Ser Gln Gly Ile Ser Ser Trp
             20                  25                  30 tta gcc tgg tat cag cag aaa cca gag aaa gcc cct aag tcc ctg atc      144
Leu Ala Trp Tyr Gln Gln Lys Pro Glu Lys Ala Pro Lys Ser Leu Ile
         35                  40                  45 tat gct gca tcc agt ttg caa agt ggg gtc cca cca agg ttc agc ggc      192
Tyr Ala Ala Ser Ser Leu Gln Ser Gly Val Pro Pro Arg Phe Ser Gly
     50                  55                  60 agt gga tct ggg aca gat ttc act ctc acc atc agc agc ctg cag cct      240
Ser Gly Ser Gly Thr Asp Phe Thr Leu Thr Ile Ser Ser Leu Gln Pro
 65                  70                  75                  80 gaa gat ttt gca act tat tac tgc caa cag tat aat agt tac cct cgg      288
Glu Asp Phe Ala Thr Tyr Tyr Cys Gln Gln Tyr Asn Ser Tyr Pro Arg
                 85                  90                  95 acg ttc ggc caa ggg acc aag gtg gaa atc aaa                          321
Thr Phe Gly Gln Gly Thr Lys Val Glu Ile Lys
            100                 105

<210> SEQ ID NO 39
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 39 gtc atc tgg gtg acc cag tct cca tcc tca ctg tct gca tct gta gga       48
Val Ile Trp Val Thr Gln Ser Pro Ser Ser Leu Ser Ala Ser Val Gly
 1               5                  10                  15 gac aga gtc acc atc act tgt cgg acg agt cag ggt att agc agc tgg       96
Asp Arg Val Thr Ile Thr Cys Arg Thr Ser Gln Gly Ile Ser Ser Trp
             20                  25                  30 tta gcc tgg tat cag cag aaa cca gag aaa gcc cct gag ctc ctg atc      144
Leu Ala Trp Tyr Gln Gln Lys Pro Glu Lys Ala Pro Glu Leu Leu Ile
         35                  40                  45
```

```
tat gct gca tcc agt ttg caa agt ggg gtc cca tca agg ttc agc ggc    192
Tyr Ala Ala Ser Ser Leu Gln Ser Gly Val Pro Ser Arg Phe Ser Gly
        50                  55                  60 agt gga tct ggg aca gat ttc act ctc acc atc agc agc ctg cag cct    240
Ser Gly Ser Gly Thr Asp Phe Thr Leu Thr Ile Ser Ser Leu Gln Pro
 65                  70                  75                  80 gaa gat ttt gca act tat tac tgc caa cag tat aat agt tac cct cgg    288
Glu Asp Phe Ala Thr Tyr Tyr Cys Gln Gln Tyr Asn Ser Tyr Pro Arg
                85                  90                  95 acg ttc ggc caa ggg acc aag gtg gaa atc aaa                        321
Thr Phe Gly Gln Gly Thr Lys Val Glu Ile Lys
            100                 105

<210> SEQ ID NO 40
<211> LENGTH: 321
<212> TYPE: DNA
<213> ORGANISM: Homo sapiens
<220> FEATURE:
<221> NAME/KEY: CDS
<222> LOCATION: (1)..(321)

<400> SEQUENCE: 40 gaa att gtg ctc acc cag tct cca tcc tca ctg tct gca tct gta ggg    48
Glu Ile Val Leu Thr Gln Ser Pro Ser Ser Leu Ser Ala Ser Val Gly
 1               5                  10                  15 gac aga gtc acc atc act tgt cgg gcg agt cag ggt att agc aac tgg    96
Asp Arg Val Thr Ile Thr Cys Arg Ala Ser Gln Gly Ile Ser Asn Trp
                20                  25                  30 tta gcc tgg tat cag cag aaa cca gag aaa gcc cct aag tcc ctg atc    144
Leu Ala Trp Tyr Gln Gln Lys Pro Glu Lys Ala Pro Lys Ser Leu Ile
            35                  40                  45 tat gct gca tcc agt ttg caa agt ggg gtc cca tca agg ttc agc ggc    192
Tyr Ala Ala Ser Ser Leu Gln Ser Gly Val Pro Ser Arg Phe Ser Gly
        50                  55                  60 agt gga tct ggg aca gat ttc act ctc acc atc agc agc ctg cag cct    240
Ser Gly Ser Gly Thr Asp Phe Thr Leu Thr Ile Ser Ser Leu Gln Pro
 65                  70                  75                  80 gaa gat ttt gcg act tat tac tgc caa cag tat aat agt tac cct cgg    288
Glu Asp Phe Ala Thr Tyr Tyr Cys Gln Gln Tyr Asn Ser Tyr Pro Arg
                85                  90                  95 acg ttc ggc caa ggg acc aag gtg gaa atc aaa                        321
Thr Phe Gly Gln Gly Thr Lys Val Glu Ile Lys
            100                 105

<210> SEQ ID NO 41
<211> LENGTH: 125
<212> TYPE: PRT
<213> ORGANISM: Homo sapiens

<400> SEQUENCE: 41

Glu Val Gln Leu Val Glu Ser Gly Gly Gly Leu Val Gln Pro Gly Gly
 1               5                  10                  15

Ser Leu Arg Leu Ser Cys Ala Ala Ala Gly Phe Thr Phe Ser Ser Tyr
                20                  25                  30

Ser Met Asn Trp Val Arg Gln Ala Pro Gly Lys Gly Leu Glu Trp Val
            35                  40                  45

Ser Tyr Ile Ser Ser Arg Ser Arg Thr Ile Tyr Tyr Ala Asp Ser Val
        50                  55                  60

Lys Gly Arg Phe Thr Ile Ser Arg Asp Asn Ala Lys Asn Ser Leu Tyr
 65                  70                  75                  80
```

-continued

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr Tyr Tyr Tyr Gly Met
            100                 105                 110

Asp Val Trp Gly Gln Gly Thr Thr Val Thr Val Ser Ser
        115                 120                 125

<210> SEQ ID NO 42
<211> LENGTH: 125
<212> TYPE: PRT
<213> ORGANISM: Homo sapiens

<400> SEQUENCE: 42

Glu Val Gln Leu Val Glu Ser Gly Gly Gly Leu Val Gln Pro Gly Gly
1               5                   10                  15

Ser Leu Arg Leu Ser Cys Ala Ala Ala Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Arg Ser Arg Ser Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr Tyr Tyr Tyr Gly Met
            100                 105                 110

Asp Val Trp Gly Gln Gly Thr Thr Val Thr Val Ser Ser
        115                 120                 125

<210> SEQ ID NO 43
<211> LENGTH: 125
<212> TYPE: PRT
<213> ORGANISM: Homo sapiens

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ala Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Arg Ser Lys Thr Ile Tyr Tyr Ala Asp Ser Val
    50                  55                  60

Lys Gly Arg Phe Thr Ile Ser Arg Asp Asn Ala Arg Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr Tyr Tyr Tyr Gly Met
            100                 105                 110

Asp Val Trp Gly Gln Gly Thr Thr Val Thr Val Ser Ser
        115                 120                 125

<210> SEQ ID NO 44
<211> LENGTH: 125
<212> TYPE: PRT
<213> ORGANISM: Homo sapiens

<400> SEQUENCE: 44

Glu Val Gln Leu Val Gln Ser Gly Gly Leu Val Gln Pro Gly Gly
1               5                   10                  15

Ser Leu Arg Leu Ser Cys Ala Ala Gly Phe Thr Phe Ser Ser Tyr
            20                  25                  30

Ser Met Asn Trp Val Arg Gln Ala Pro Gly Lys Gly Leu Glu Trp Val
        35                  40                  45

Ser Tyr Ile Ser Ser Arg Ser Arg Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Asp Glu Asp Thr Ala Val Tyr Tyr Cys
                85                  90                  95

Ala Arg Asp Tyr Gly Gly Gln Pro Pro Tyr His Tyr Tyr Tyr Gly Met
            100                 105                 110

Asp Val Trp Gly Gln Gly Thr Thr Val Thr Val Ser Ser
        115                 120                 125

<210> SEQ ID NO 45
<211> LENGTH: 107
<212> TYPE: PRT
<213> ORGANISM: Homo sapiens

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Val Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 46
<211> LENGTH: 107
<212> TYPE: PRT
<213> ORGANISM: Homo sapiens

<400> SEQUENCE: 46

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Pro Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg

Thr Phe Gly Gln Gly Thr Lys Val Glu Ile Lys
            100                 105

<210> SEQ ID NO 47
<211> LENGTH: 107
<212> TYPE: PRT
<213> ORGANISM: Homo sapiens

<400> SEQUENCE: 47

Asp Ile Gln Met Thr Gln Ser Pro Ser Ser Leu Ser Ala Ser Val Gly
1               5                   10                  15

Asp Arg Val Thr Ile Thr Cys Arg Thr Ser Gln Gly Ile Ser Ser Trp
            20                  25                  30

Leu Ala Trp Tyr Gln Gln Lys Pro Glu Lys Ala Pro Glu Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 48
<211> LENGTH: 107
<212> TYPE: PRT
<213> ORGANISM: Homo sapiens

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Ser Asn Trp
            20                  25                  30

Leu Ala Trp Tyr Gln Gln Lys Pro Glu Lys Ala Pro Lys Ser Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Ser Tyr Pro Arg
                85                  90                  95

Thr Phe Gly Gln Gly Thr Lys Val Glu Ile Lys
            100                 105

<210> SEQ ID NO 49
<211> LENGTH: 98
<212> TYPE: PRT
<213> ORGANISM: Homo sapiens

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ser Met Asn Trp Val Arg Gln Ala Pro Gly Lys Gly Leu Glu Trp Val
        35                  40                  45

```
Ser Tyr Ile Ser Ser Ser Ser Thr Ile Tyr Tyr Ala Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Asp Glu Asp Thr Ala Val Tyr Tyr Cys
                 85                  90                  95

Ala Arg

<210> SEQ ID NO 50
<211> LENGTH: 95
<212> TYPE: PRT
<213> ORGANISM: Homo sapiens

<400> SEQUENCE: 50

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Gly Ile Ser Ser Trp
                 20                  25                  30

Leu Ala Trp Tyr Gln Gln Lys Pro Glu Lys Ala Pro Lys Ser Leu Ile
             35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Asn Ser Tyr Pro
                 85                  90                  95

<210> SEQ ID NO 51
<211> LENGTH: 352
<212> TYPE: PRT
<213> ORGANISM: Homo sapiens

<400> SEQUENCE: 51

Met Glu Gly Ile Ser Ile Tyr Thr Ser Asp Asn Tyr Thr Glu Glu Met
 1               5                  10                  15

Gly Ser Gly Asp Tyr Asp Ser Met Lys Glu Pro Cys Phe Arg Glu Glu
                 20                  25                  30

Asn Ala Asn Phe Asn Lys Ile Phe Leu Pro Thr Ile Tyr Ser Ile Ile
             35                  40                  45

Phe Leu Thr Gly Ile Val Gly Asn Gly Leu Val Ile Leu Val Met Gly
 50                  55                  60

Tyr Gln Lys Lys Leu Arg Ser Met Thr Asp Lys Tyr Arg Leu His Leu
 65                  70                  75                  80

Ser Val Ala Asp Leu Leu Phe Val Ile Thr Leu Pro Phe Trp Ala Val
                 85                  90                  95

Asp Ala Val Ala Asn Trp Tyr Phe Gly Asn Phe Leu Cys Lys Ala Val
                100                 105                 110

His Val Ile Tyr Thr Val Asn Leu Tyr Ser Ser Val Leu Ile Leu Ala
                115                 120                 125

Phe Ile Ser Leu Asp Arg Tyr Leu Ala Ile Val His Ala Thr Asn Ser
            130                 135                 140

Gln Arg Pro Arg Lys Leu Leu Ala Glu Lys Val Val Tyr Val Gly Val
145                 150                 155                 160

Trp Ile Pro Ala Leu Leu Leu Thr Ile Pro Asp Phe Ile Phe Ala Asn
                165                 170                 175
```

```
Val Ser Glu Ala Asp Asp Arg Tyr Ile Cys Asp Arg Phe Tyr Pro Asn
            180                 185                 190

Asp Leu Trp Val Val Val Phe Gln Phe Gln His Ile Met Val Gly Leu
        195                 200             205

Ile Leu Pro Gly Ile Val Ile Leu Ser Cys Tyr Cys Ile Ile Ile Ser
        210             215                 220

Lys Leu Ser His Ser Lys Gly His Gln Lys Arg Lys Ala Leu Lys Thr
225                 230                 235                 240

Thr Val Ile Leu Ile Leu Ala Phe Phe Ala Cys Trp Leu Pro Tyr Tyr
                245                 250                 255

Ile Gly Ile Ser Ile Asp Ser Phe Ile Leu Leu Glu Ile Ile Lys Gln
            260                 265                 270

Gly Cys Glu Phe Glu Asn Thr Val His Lys Trp Ile Ser Ile Thr Glu
        275                 280                 285

Ala Leu Ala Phe Phe His Cys Cys Leu Asn Pro Ile Leu Tyr Ala Phe
        290             295                 300

Leu Gly Ala Lys Phe Lys Thr Ser Ala Gln His Ala Leu Thr Ser Val
305                 310                 315                 320

Ser Arg Gly Ser Ser Leu Lys Ile Leu Ser Lys Gly Lys Arg Gly Gly
            325                 330                 335

His Ser Ser Val Ser Thr Glu Ser Glu Ser Ser Ser Phe His Ser Ser
            340                 345                 350
```